US009745305B2

(12) United States Patent
Albrecht et al.

(10) Patent No.: US 9,745,305 B2
(45) Date of Patent: *Aug. 29, 2017

(54) MODULATORS OF METHYL MODIFYING ENZYMES, COMPOSITIONS AND USES THEREOF

(71) Applicant: Constellation Pharmaceuticals, Inc., Cambridge, MA (US)

(72) Inventors: Brian K. Albrecht, Cambridge, MA (US); James Edmund Audia, Cambridge, MA (US); Andrew Cook, Stow, MA (US); Alexandre Côté, Cambridge, MA (US); Les A. Dakin, Natick, MA (US); Victor S. Gehling, Somerville, MA (US); Jean-Christophe Harmange, Andover, MA (US); Christopher G. Nasveschuk, Stoneham, MA (US); Rishi G. Vaswani, Lexington, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/769,471

(22) PCT Filed: Mar. 12, 2014

(86) PCT No.: PCT/US2014/025081
§ 371 (c)(1),
(2) Date: Aug. 21, 2015

(87) PCT Pub. No.: WO2014/151142
PCT Pub. Date: Sep. 25, 2014

(65) Prior Publication Data
US 2016/0009718 A1    Jan. 14, 2016

Related U.S. Application Data

(60) Provisional application No. 61/790,566, filed on Mar. 15, 2013.

(51) Int. Cl.
C07D 487/04    (2006.01)

(52) U.S. Cl.
CPC .................. *C07D 487/04* (2013.01)

(58) Field of Classification Search
None
See application file for complete search history.

(56) References Cited

U.S. PATENT DOCUMENTS

| 4,738,971 A | 4/1988 | Eriksoo et al. |
| 5,308,854 A | 5/1994 | Hoffman, Jr. et al. |
| 7,838,520 B2 | 11/2010 | Delorme et al. |
| 8,410,088 B2 | 4/2013 | Kuntz et al. |
| 8,536,179 B2 | 9/2013 | Miller et al. |
| 8,846,935 B2 | 9/2014 | Duquenne et al. |
| 9,051,269 B2 | 6/2015 | Albrecht et al. |
| 9,085,583 B2 | 7/2015 | Albrecht et al. |
| 9,206,128 B2 | 12/2015 | Albrecht et al. |
| 9,374,093 B2 | 6/2016 | Pelley et al. |
| 2003/0207875 A1 | 11/2003 | Gymer et al. |
| 2003/0229081 A1 | 12/2003 | Maduskuie |
| 2004/0186138 A1 | 9/2004 | Annoura et al. |
| 2005/0266473 A1 | 12/2005 | Zhang et al. |
| 2006/0035938 A1 | 2/2006 | Bladh et al. |
| 2007/0155744 A1 | 7/2007 | Jones et al. |
| 2008/0027050 A1 | 1/2008 | Terauchi et al. |
| 2008/0227826 A1 | 9/2008 | Frechette et al. |
| 2008/0280917 A1 | 11/2008 | Albrecht et al. |
| 2009/0029991 A1 | 1/2009 | Stokes et al. |
| 2009/0075833 A1 | 3/2009 | Chinnaiyan et al. |
| 2009/0270361 A1 | 10/2009 | Ito et al. |
| 2010/0069630 A1 | 3/2010 | Lee et al. |
| 2010/0222420 A1 | 9/2010 | Chinnaiyan et al. |
| 2010/0261743 A1 | 10/2010 | Londregan et al. |
| 2010/0298270 A1 | 11/2010 | Keana et al. |
| 2011/0105509 A1 | 5/2011 | Kaila et al. |
| 2011/0212946 A1 | 9/2011 | Barrow et al. |
| 2012/0071418 A1 | 3/2012 | Copeland et al. |
| 2013/0040906 A1 | 2/2013 | Kuntz et al. |
| 2013/0230511 A1 | 9/2013 | Heymach et al. |
| 2014/0107122 A1 | 4/2014 | Kuntz et al. |
| 2014/0142083 A1 | 5/2014 | Kuntz et al. |
| 2015/0259351 A1 | 9/2015 | Albrecht et al. |

FOREIGN PATENT DOCUMENTS

| WO | 03/020722 A1 | 3/2003 |
| WO | 03/079986 A2 | 10/2003 |
| WO | 2007/011626 A2 | 1/2007 |
| WO | 2007/014838 A1 | 2/2007 |
| WO | 2007/067968 A2 | 6/2007 |
| WO | 2009/006577 A2 | 1/2009 |
| WO | 2009/087285 A1 | 7/2009 |

(Continued)

OTHER PUBLICATIONS

Alexei Vazquez, "Optimization of Personalized Therapies for Anticancer Treatment," BMC Systems Biology, 2013, 7:31, 11 pages, http://www.biomedcentral.com/1752-0509/7/31.
Amatangelo et al., "Three-Dimensional Culture Sensitizes Epithelial Ovarian Cancer Cells to EZH2 Methyltransferase Inhibition," Cell Cycle, 12(13), 2013, 2113-2119.
CAS Registry No. 1061629-12-6.
CAS Registry No. 1100242-53-2.
CAS Registry No. 1118826-71-3.
CAS Registry No. 1269034-31-2.
CAS Registry No. 1269036-62-4.
CAS Registry No. 1278089-62-5.
CAS Registry No. 1290560-58-5.

(Continued)

*Primary Examiner* — David K O'Dell
(74) *Attorney, Agent, or Firm* — McCarter & English, LLP; Steven G. Davis; Michael J. DeGrazia

(57) ABSTRACT

Agents for modulating methyl modifying enzymes, compositions and uses thereof are provided herein.

17 Claims, No Drawings

(56) References Cited

FOREIGN PATENT DOCUMENTS

| | | |
|---|---|---|
| WO | 2009/153721 A1 | 12/2009 |
| WO | 2011/131741 A1 | 10/2011 |
| WO | 2011/140324 A1 | 11/2011 |
| WO | 2011/140325 A1 | 11/2011 |
| WO | 2012/005805 A1 | 1/2012 |
| WO | 2012/024543 A1 | 2/2012 |
| WO | 2012/051492 A2 | 4/2012 |
| WO | 2012/068589 A2 | 5/2012 |
| WO | 2012/075080 A1 | 6/2012 |
| WO | 2012/115885 A1 | 8/2012 |
| WO | 2012/118812 A2 | 9/2012 |
| WO | 2013/039988 A1 | 3/2013 |
| WO | 2013/049770 A2 | 4/2013 |
| WO | 2013/067296 A1 | 5/2013 |
| WO | 2013/067300 A1 | 5/2013 |
| WO | 2013/067302 A1 | 5/2013 |
| WO | 2013/075083 A1 | 5/2013 |
| WO | 2013/075084 A1 | 5/2013 |
| WO | 2013/078320 A1 | 5/2013 |
| WO | 2013/120104 A2 | 8/2013 |
| WO | 2013/138361 A1 | 9/2013 |
| WO | 2013/155317 A1 | 10/2013 |
| WO | 2013/155464 A1 | 10/2013 |
| WO | 2013/173441 A2 | 11/2013 |
| WO | 2014/049488 A1 | 4/2014 |
| WO | 2014/062720 A2 | 4/2014 |
| WO | 2014/062733 A2 | 4/2014 |
| WO | 2014/071109 A1 | 5/2014 |
| WO | 2014/077784 A1 | 5/2014 |
| WO | 2014/085666 A1 | 6/2014 |
| WO | 2014/092905 A1 | 6/2014 |
| WO | 2014/097041 A1 | 6/2014 |
| WO | 2014/100080 A1 | 6/2014 |
| WO | 2015/200650 A1 | 12/2015 |

OTHER PUBLICATIONS

Extended European Search Report issued in European Application No. 13746186.9, dated Aug. 5, 2015. 6 pages.

Fiskus, et al., "Combined Epigenetic Therapy with the Histone Methyltransferase EZH2 Inhibitor 3-Deazaneplanocin A and the Histone Deacetylase Inhibitor Panobinostat Against Human AML Cells," Blood, Sep. 24, 2009, 114:13, pp. 2733-2743.

Fiskus, et al., "Histone Deacetylase Inhibitors Deplete Enhancer of Zeste 2 and Associated Polycomb Repressive complex 2 Proteins in Human Acute Leukemia Cells," Molecular Cancer Therapeutics, 2006;5:3096-3104.

International Search Report, International Application No. PCT/US2013/025639, International Filing Date Feb. 11, 2013, Mailed May 8, 2013, 9 pages.

Ito et al., "A Medium-term Rat Liver Bioassay for Rapid in Vivo Detection of Carcinogenic Potential of Chemicals" Cancer Science 94(1), 3-8 (2003).

Knutson et al., "Selective Inhibition of EZH2 by EPZ-6438 Leads to Potent Antitumor Activity in EZH2-Mutant Non-Hodgkin Lymphoma," Molecular Cancer Therapeutics, 13(4), 2014, 842-854.

Knutson, et al., "A Selective Inhibitor of EZH2 Blocks H3K27 Methylation and Kills Mutant Lymphoma Cells," Nature Chemical Biology, 8(11), 2012, 890-896.

Knutson, et al., "Durable Tumor Regression in Genetically Altered Malignant Rhabdoid Tumors by Inhibition of Methyltransferase EZH2," Proceedings of the National Academy of Sciences of the United States of America, 110(19), 2013, 7922-7927.

Konze, et al., "An Orally Bioavailable Chemical Probe of the Lysine Methyltransferases EZH2 and EZH1," ACS Chemical Biology, (2013), 8(6), 1324-1334, CAPLUS, DOI: 10.1021/cb400133j.

McCabe, et al., "EZH2 Inhibition as a Therapeutic Strategy for Lymphoma with EZH2-Activating Mutations," Nature, 492(7427), 2012, 108-112.

PubChem Compound Summary for CID 40170690, May 30, 2009, 2 pages.

PubChem Compound Summary for CID 50961558, Mar. 29, 2011, 2 pages.

PubChem Compound Summary for CID 6918837, Jul. 28, 2006, 2 pages.

PubChem Compound Summary for CID 73087, Aug. 1, 2005, 2 pages.

Qi, et al., "Selective Inhibition of Ezh2 by a Small Molecule Inhibitor Blocks Tumor Cells Proliferation," Proceedings of the National Academy of Sciences of the United States of America, 109(52), 2012, 21360-21365.

Registry, May 25, 2011, RN: 1300453-83-1.
Registry, Sep. 1, 2011, RN: 1326727-17-6.
Registry, Sep. 2, 2011, RN: 1327055-57-1.
Registry, Sep. 4, 2011, RN: 1328132-30-4.
Registry, Sep. 5, 2011, RN: 1328462-28-7.
Registry, Sep. 29, 2011, RN: 1333889-30-7.
Registry, Sep. 6, 2011, RN 1328976-87-9.
Registry, Sep. 7, 2011, RN 1329352-49-9.
Registry, Sep. 7, 2011, RN: 1329234-68-5.

Spannhoff, et al., "The Emerging Therapeutic Potential of Histone Methyltransferase and Demethylase Inhibitors," Chem Med Chem, 2009, 4:1568-1582.

STN registry database compound 1002886-67-0 from the ZINC (Soichet Laboratory) (entered STN on Feb. 12, 2008).

STN registry database compound 950111-40-7 from Chemical Library Supplier Enamine (entered STN on Oct. 10, 2007).

Van Aller, et al., "Long Residence Time Inhibition of EZH2 in Activated Polycomb Repressive Complex 2," ACS Chem. Biol., 9(3), 2014, 622-629.

Venkatesh et al., "Role of the Development Scientist in Compound Lead Selection and Optimization" J. Pharm. Sci. vol. 89, No. 2, 145-154 (2000).

Woo, et al., "Biological Evaluation of Tanshindiols as EZH2 Histone Methyltransferase Inhibitors," Bioorganic & Medicinal Chemistry Letters, 24(11), 2014, 2486-2492.

Yap, et al., "Somatic mutations at EZH2 Y641 act dominantly through a mechanism of selectively altered PRC2 catalytic activity, to increase H3K27 trimethylation," Blood, vol. 117, No. 8, Feb. 24, 2011, pp. 2451-2459.

Verma, et al., "Identification of Potent, Selective, Cell-Active Inhibitors of the Histone Lysine Methyltransferase EZH2," ACS Medicinal Chemistry Letters, vol. 3, No. 12, Dec. 13, 2012, pp. 1091-1096, XP55106955.

MODULATORS OF METHYL MODIFYING ENZYMES, COMPOSITIONS AND USES THEREOF

CROSS-REFERENCE TO RELATED APPLICATIONS

This application is a 35 U.S.C. §371 national stage filing of International Application No. PCT/US2014/025081, filed Mar. 12, 2014, which claims priority to U.S. Provisional Application No. 61/790,566, filed Mar. 15, 2013. The entire contents of each of the foregoing applications are hereby incorporated by reference.

BACKGROUND OF THE INVENTION

Epigenetics is the study of heritable changes in gene expression caused by mechanisms other than changes in the underlying DNA sequence. Molecular mechanisms that play a role in epigenetic regulation include DNA methylation and chromatin/histone modifications. Histone methylation, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) Curr. Opin. Genet. Dev. 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) Nature 389:251-260).

Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation, sumoylation, ubiquitination, citrullination, deimination, and biotinylation. The core of histones H2A and H3 can also be modified. Histone modifications are integral to diverse biological processes such as gene regulation, DNA repair, and chromosome condensation.

One class of histone methylases is characterized by the presence of a SET domain, comprising about 130 amino acids. EZH2 is an example of a human SET-domain containing methylase. EZH2 associates with EED (Embryonic Ectoderm Development) and SUZ12 (suppressor of zeste 12 homolog) to form a complex known as PRC2 (Polycomb Group Repressive Complex 2) having the ability to trimethylate histone H3 at lysine 27 (Cao and Zhang, Mol. Cell 15:57-67, 2004). PRC2 complexes can also include RBAP46 and RBAP48 subunits. Another example is the related methylase EZH1.

The oncogenic activities of EZH2 have been shown by a number of studies. In cell line experiments, over-expression of EZH2 induces cell invasion, growth in soft agar, and motility while knockdown of EZH2 inhibits cell proliferation and cell invasion (Kleer et al., 2003, Proc. Nat. Acad. Sci. USA 100:11606-11611; Varambally et al., (2002), "The polycomb group protein EZH2 is involved in progression of prostate cancer," Nature 419, 624-629). It has been shown that EZH2 represses the expression of several tumor suppressors, including E-cadherin, DAB2IP and RUNX3 among others. In xenograft models, EZH2 knockdown inhibits tumor growth and metastasis. Recently, it has been shown that down modulation of EZH2 in murine models blocks prostate cancer metastasis (Min et al., "An oncogene-tumor suppressor cascade drives metastatic prostate cancer by coordinately activating Ras and nuclear factor-kappaB," Nat Med. 2010 March; 16(3):286-94). EZH2 overexpression is associated with aggressiveness of certain cancers such as breast cancer (Kleer et al., Proc. Nat. Acad. Sci. USA 100:11606-11611, 2003). Recent studies also suggest that prostate cancer specific oncogenic fusion gene TMPRSS2-ERG induces repressive epigenetic programs via direct activation of EZH2 (Yu et al., "An Integrated Network of Androgen Receptor, Polycomb, and TMPRSS2-ERG Gene Fusions in Prostate Cancer Progression," Cancer Cell. 2010 May 18; 17(5):443-454).

SUMMARY OF THE INVENTION

The present disclosure encompasses the recognition that methyl modifying enzymes, in particular EZH2 and mutant forms thereof, are an attractive target for modulation, given their role in the regulation of diverse biological processes. It has now been found that compounds of this invention, and pharmaceutically acceptable compositions thereof, are effective as agents that modulate the activity of EZH2 and, in some cases, EZH1. Such compounds have the general formula I:

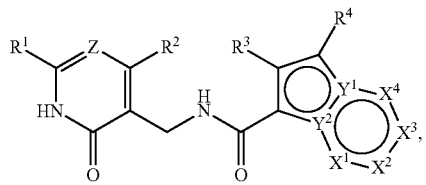

or a pharmaceutically acceptable salt or tautomer thereof, wherein each variable is as defined herein.

Compounds of the present invention, and pharmaceutically acceptable compositions thereof, are useful for treating a variety of diseases, disorders or conditions, associated with a methyl modifying enzyme. Such diseases, disorders, or conditions include those described herein.

Compounds provided by this invention are also useful for the study of methyl modifying enzymes in biological and pathological phenomena; the study of intracellular signal transduction pathways mediated by methyl modifying enzymes and the comparative evaluation of new methyl modifying enzyme modulators.

DETAILED DESCRIPTION OF CERTAIN EMBODIMENTS

1. General Description of Compounds of the Invention

1. In certain embodiments, the present invention provides a compound of the formula I:

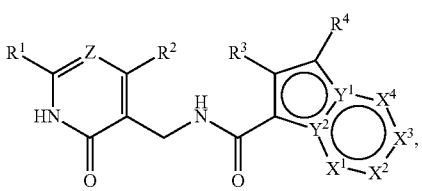

(I)

or a pharmaceutically acceptable salt or tautomer thereof, wherein:

Z is $C(R^9)$ or N;

one of $Y^1$ or $Y^2$ is N and the other is C;

one of $X^1$, $X^2$, $X^3$, or $X^4$ is N and each of the others is independently $C(R^5)$;

each of $R^1$, $R^2$ and $R^9$ is independently selected from hydrogen, halo, —OH, —CN, $C_1$-$C_4$ alkyl, —O—($C_1$-$C_4$ alkyl), —N($R^7$)$_2$, —($C_0$-$C_4$ alkylene)-aryl, —($C_0$-$C_4$ alkylene)-heteroaryl, —($C_0$-$C_4$ alkylene)-heterocyclyl, and —($C_0$-$C_4$ alkylene)-carbocyclyl; or $R^1$ and $R^9$ are taken together with atoms to which they are bound to form an aryl, heteroaryl, heterocyclyl, or carbocyclyl ring; or $R^2$ and $R^9$ are taken together with atoms to which they are bound to form an aryl, heteroaryl, heterocyclyl, or carbocyclyl ring;

each of $R^3$, $R^4$ and $R^5$ is independently selected from hydrogen, halo, —CN, —($C_0$-$C_4$ alkylene)-$R^8$, —($C_2$-$C_6$ alkenyl or alkynyl)-$R^6$, —($C_1$-$C_4$ alkylene)-O—$R^6$, —($C_1$-$C_4$ alkylene)-O—($C_1$-$C_4$ alkylene)-$R^8$, —O—($C_0$-$C_4$ alkylene)-$R^6$, —O—($C_2$-$C_4$ alkylene)-O—$R^8$, —O—($C_1$-$C_4$ alkylene)-$R^6$, —($C_0$-$C_4$ alkylene)-N($R^7$)$_2$, —($C_0$-$C_4$ alkylene)-C(O)—O—$R^6$, —($C_0$-$C_4$ alkylene)-O—C(O)—$R^6$, —($C_0$-$C_4$ alkylene)-C(O)—N($R^7$)$_2$, —($C_0$-$C_4$ alkylene)-N($R^7$)—C(O)—$R^6$, —O—($C_1$-$C_4$ alkylene)-C(O)—N($R^7$)$_2$, —O—($C_2$-$C_4$ alkylene)-N($R^7$)—C(O)—($R^7$), —($C_0$-$C_4$ alkylene)-S(O)—$R^8$, —($C_0$-$C_4$ alkylene)-S(O)$_2$—$R^8$, —($C_0$-$C_4$ alkylene)-S(O)$_2$—N($R^7$)$_2$, —($C_0$-$C_4$ alkylene)-N($R^7$)—S(O)$_2$—$R^8$, and —($C_0$-$C_4$ alkylene)-C(O)—$R^8$ each $R^6$ is independently selected from hydrogen or $R^8$;

each $R^7$ is independently selected from —($C_0$-$C_4$ alkylene)-$R^6$, —($C_0$-$C_4$ alkylene)-O—$R^6$, —S(O)$_2$—$R^8$, —C(=O)—$R^8$, —C(=O)—N($R^6$)$_2$, —($C_1$-$C_4$ alkylene)-O—C(=O)—$R^8$ and —($C_0$-$C_4$ alkylene)-C(=O)—O—$R^6$; or two $R^7$ are taken together with the nitrogen atom to which they are commonly bound to form an optionally substituted heterocyclyl or heteroaryl;

$R^8$ is selected from $C_1$-$C_4$ alkyl, aryl, heteroaryl, carbocyclyl and heterocyclyl; wherein unless otherwise designated any alkyl, alkylene, alkenyl, alkynyl, aryl, heteroaryl, heterocyclyl or carbocyclyl portion of the compound is optionally substituted.

2. Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E.L. Eliel, Ed., Univ. of Notre Dame Press, Notre Dame, Ind. 1972).

A wavy bond ( ～ ) at a chiral center in a chemical structure is used to denote compounds of the invention that are optically pure, but whose optical rotation has not been determined. A straight bond at a chiral center indicates a racemic mixture although, as stated above, the invention also includes all possible isomeric forms of the racemate.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl) alkyl, (cycloalkenyl)alkyl or (cycloalkyl)alkenyl.

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group.

The term "$C_0$ alkylene" as used herein means a bond. Thus, a moiety defined herein as "—($C_0$-$C_6$ alkylene)-aryl" includes both -aryl (i.e., $C_0$ alkylene-aryl) and —($C_1$-$C_6$ alkylene)-aryl.

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "carbocyclyl" (also referred to herein as "carbocycle" "cycloaliphatic" or "cycloalkyl"), as used herein, means a monocyclic hydrocarbon or bicyclic hydrocarbon that is completely saturated or that contains one or more units of unsaturation, but where there is no ring is aromatic.

The term "aryl" used alone or as part of a larger moiety as in "aralkyl", "aralkoxy", or "aryloxyalkyl", refers to monocyclic and bicyclic carbon ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more carbocyclyl rings regardless of whether the aromatic carbon ring or the carbocyclic ring is the pendant ring, or a group in which an aromatic carbon ring is fused to one or more heteroaryl or heterocyclyl, rings, such as indanyl, phthalimidyl, naphthimidyl, phenanthridinyl, or tetrahydronaphthyl, and the like, wherein the pendant ring of the fused ring system is the aromatic carbon ring.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, wherein the pendant ring of the fused ring system is heteroaromatic. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, 5,6,7,8-tetrahydroquinolinyl, 5,6,7,8-tetrahydroisoquinolinyl, and pyrido[2,3-b]-1,4-oxazin-3(4H)-one. A hetero aryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. The term "heteroarylene" refers to a bivalent mono- or bicyclic heteroaryl ring.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. In certain embodiments, a "heterocycle" group is a 1,1'-heterocyclylene group (i.e., a spiro-fused ring). When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any hetero atom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, 1,2,3,4-tetrahydroquinolinyl, 1,2,3,4-tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, wherein the pendant ring of the fused ring system is heterocyclyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —OC(O)$(CH_2)_{0-4}SR$; —$SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —SC(S)$SR^\circ$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; —$SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)O$R^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^\bullet$, -(halo$R^\bullet$), —OH, —OR$^\bullet$, —O(halo$R^\bullet$), —CN, —C(O)OH, —C(O)OR$^\bullet$, —$NH_2$, —NHR$^\bullet$, —NR$^\bullet_2$, or —$NO_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR$^∀$), —OH, —OR$^∀$, —O(haloR$^∀$), —CN, —C(O)OH, —C(O)OR$^∀$, —NH$_2$, —NHR$^∀$, —NR$^∀$$_2$, or —NO$_2$, wherein each R$^∀$ is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "inhibitor" is defined as a compound that binds to and/or inhibits a target S-adenosylmethionine (SAM) utilizing enzyme with measurable affinity. In certain embodiments, an inhibitor has an IC$_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in activity of at least one SAM utilizing enzyme between a sample comprising a provided compound, or composition thereof, and at least one SAM dependent enzyme, and an equivalent sample comprising at least one SAM dependent enzyme, in the absence of said compound, or composition thereof.

3. Description of Exemplary Compounds

In certain embodiments, the present invention provides a compound of formula I:

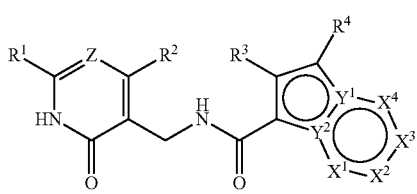

I or a pharmaceutically acceptable salt or tautomer thereof, wherein each variable is as defined above and described herein.

As defined generally above and herein, Z is =C(R$^9$)— or =N—, wherein R$^9$ is as defined above and described herein. In some embodiments, Z is =C(R$^9$)— wherein R$^9$ is as defined above and described herein. In some embodiments, Z is =CH—. In some embodiments, Z is =N—.

As defined generally above and herein, one of Y$^1$ or Y$^2$ is N and the other is C. In some embodiments, Y$^1$ is N and Y$^2$ is C. In some embodiments Y$^2$ is C and Y$^2$ is N.

As defined generally above and herein, one of X$^1$, X$^2$, X$^3$, or X$^4$ is N and each of the others is independently C(R$^5$). In some embodiments, X$^1$ is N and each of X$^2$, X$^3$, and X$^4$ is C(R$^5$). In some embodiments, X$^2$ is N and each of X$^1$, X$^3$, and X$^4$ is C(R$^5$). In some embodiments, X$^3$ is N and each of X$^1$, X$^2$, and X$^4$ is C(R$^5$). In some embodiments, X$^4$ is N and each of X$^1$, X$^2$, and X$^3$ is C(R$^5$). In one aspect of these embodiments, Y$^1$ is N, X$^4$ is N, and each of X$^1$, X$^2$, and X$^3$ is C(R$^5$). In another aspect of these embodiments, Y$^1$ is N, X$^2$ is N, and each of X$^1$, X$^3$, and X$^4$ is C(R$^5$). In an alternate aspect of these embodiments, Y$^2$ is N, X$^3$ is N, and X$^1$, X$^2$, and X$^4$ is C(R$^5$). In a more specific aspect of these embodiments, Y$^1$ is N, X$^4$ is N, and X$^5$ is selected from C(H), C(OCH$_3$) and C(CH$_3$).

As defined generally above and herein, each R$^1$ and R$^2$ is independently selected from hydrogen, halo, —OH, —CN, C$_1$-C$_4$ alkyl, —O—(C$_1$-C$_4$ alkyl), —N(R$^7$)$_2$, —(C$_0$-C$_4$ alkylene)-aryl, —(C$_0$-C$_4$ alkylene)-heteroaryl, —(C$_0$-C$_4$ alkylene)-heterocyclyl, and —(C$_0$-C$_4$ alkylene)-carbocyclyl; or one of R$^1$ or R$^2$ is taken together with R$^9$ and the atoms to which they are bound to form an aryl, heteroaryl, heterocyclyl, or carbocyclyl ring, wherein each R$^7$ and R$^9$ are as defined herein. In some embodiments, R$^1$ is —CH$_3$. In some embodiments, R$^2$ is selected from —CH$_3$, —CH$_2$CH$_3$, —CH$_2$CH$_2$CH$_3$, —OCH$_3$, and —OCHF$_2$. In some embodiments, R$^1$ is —CH$_3$; and R$^2$ is selected from —CH$_3$, —CH$_2$CH$_3$, —CH$_2$CH$_2$CH$_3$, —OCH$_3$, and —OCHF$_2$.

As defined generally above and herein, R$^3$, R$^4$ and each R$^5$ are independently selected from hydrogen, halo, —CN, —(C$_0$-C$_4$ alkylene)-R$^8$, —(C$_2$-C$_6$ alkenyl or alkynyl)-R$^6$, —(C$_1$-C$_4$ alkylene)-O—R$^6$, —(C$_1$-C$_4$ alkylene)-O—(C$_1$-C$_4$ alkylene)-R$^8$, —O—(C$_0$-C$_4$ alkylene)-R$^6$, —O—(C$_2$-C$_4$ alkylene)-O—R$^8$, —O—(C$_1$-C$_4$ alkylene)-R$^6$, —(C$_0$-C$_4$ alkylene)-N(R$^7$)$_2$, —(C$_0$-C$_4$ alkylene)-C(O)—O—R$^6$, —(C$_0$-C$_4$ alkylene)-O—C(O)—R$^6$, —(C$_0$-C$_4$ alkylene)-C(O)—N(R$^7$)$_2$, —(C$_0$-C$_4$ alkylene)-N(R$^7$)—C(O)—R$^6$, —O—(C$_1$-C$_4$ alkylene)-C(O)—N(R$^7$)$_2$, —O—(C$_2$-C$_4$ alkylene)-N(R$^7$)—C(O)—(R$^7$), —(C$_0$-C$_4$ alkylene)-S(O)—R$^8$, —(C$_0$-C$_4$ alkylene)-S(O)$_2$—R$^8$, —(C$_0$-C$_4$ alkylene)-S(O)$_2$—N(R$^7$)$_2$, —(C$_0$-C$_4$ alkylene)-N(R$^7$)—S(O)$_2$—R$^8$, and —(C$_0$-C$_4$ alkylene)-C(O)—R$^8$, wherein each R$^6$, each R$^7$, and R$^8$ are defined herein. In some embodiments, R$^3$ is —CH$_3$. In some embodiments, R$^3$ is chloro.

In some embodiments, R$^4$ is selected from -heteroaryl, —CH(CH$_3$)-heterocyclyl, —CH(CH$_3$)-heteroaryl, —CH(CH$_3$)-aryl, —CH(CH$_3$)-carbocyclyl, —CH(CH$_3$)—N(R$^{10}$)—S(O)$_2$—(C$_1$-C$_4$ alkyl), and —CH(CH$_3$)—N(R$^{10}$)—C(O)—(C$_1$-C$_4$ alkyl), wherein R$^{10}$ is selected from hydrogen and C$_1$-C$_4$ alkyl. In some embodiments, R$^4$ is additionally selected from —CH(CH$_3$)N(R$^{10}$)$_2$. In a specific aspect of these embodiments, any heteroaryl, heterocyclyl, aryl or carbocyclyl portion of R$^4$ is optionally substituted. In a more specific aspect of these embodiments, any heteroaryl, heterocyclyl, aryl or carbocyclyl portion of R$^4$ is optionally substituted with oxo, methyl, methylsulfonyl, propyl, ethyl, ethylcarbonyl, ethylsulfonyl, or methylcarbonyl, wherein the methyl, ethyl or propyl portion of the substituent is further optionally substituted with up to four substituents independently selected from fluoro, methyl and hydroxy. In a more specific aspect of these embodiments, R$^4$ is selected from 1-(1-methylpiperidin-4-yl)ethyl, 5-methyl-isoxazol-4- yl, 3,5-dimethyl-isoxazol-4-yl, 1,5-dimethyl-1H-pyrazol-3-yl, 1-(1-ethylsulfonylpiperidin-4-yl)ethyl, 1,4-dimethyl-1H-pyrazol-5-yl, 1-methyl-1H-pyrazol-5-yl, 1-(tetrahydropyran-4-yl)ethyl, 1-(pyridin-3-yl)ethyl, 1-(methylsulfonylamino)ethyl, 1-(1-methyl-2-oxopiperidin-4-yl)ethyl, 1-(methylsulfonyl(N-ethyl)amino)ethyl, 1-(methylsulfonyl(N-methyl)amino)ethyl, 1-phenylethyl, 1-(methylcarbonyl(N-methyl)amino)ethyl, and 1-cyclopropylethyl.

In some embodiments, $R^4$ is selected from 1-(1-(2,2-difluoropropanoyl)piperidin-4-yl)ethyl, 1-(1-(2,2-difluoroethanoyl)piperidin-4-yl)ethyl, 1-(1-(2,2,2-trifluoroethyl)piperidin-4-yl)ethyl, 1-(1-(2-hydroxy-2-methylpropyl)piperidin-4-yl)ethyl, 1-(1-(2,2,2-trifluoroethanoyl)piperidin-4-yl)ethyl, 1-(1-(2-fluoro-2-methylpropyl)piperidin-4-yl)ethyl, 1-(1-(2,2-difluoropropyl)piperidin-4-yl)ethyl, 1-(1-(3,3,3-trifluoropropanoyl)piperidin-4-yl)ethyl, 1-(1-(3,3,3-trifluoropropyl)piperidin-4-yl)ethyl, 1-(1-(2,2-difluoroethyl)piperidin-4-yl)ethyl, 1-(dimethylamino)ethyl, morpholine-4-carbonyl, 4-methylsulfonylpiperazin-1-ylcarbonyl, 1-(tetrahydro-2H-pyran-4-yl)ethyl, 1-(1-(2-fluoro-2-methylpropanoyl)piperidin-4-yl)ethyl, and 1-(ethyl(methyl)amino)ethyl.

In some embodiments, $R^5$ is hydrogen. In a more specific aspect of these embodiment, $R^3$ is —$CH_3$, $R^5$ is hydrogen; and $R^4$ is selected from 1-(1-methylpiperidin-4-yl)ethyl, 5-methyl-isoxazol-4-yl, 3,5-dimethyl-isoxazol-4-yl, 1,5-dimethyl-1H-pyrazol-3-yl, 1-(1-ethylsulfonylpiperidin-4-yl)ethyl, 1,4-dimethyl-1H-pyrazol-5-yl, 1-methyl-1H-pyrazol-5-yl, 1-(tetrahydropyran-4-yl)ethyl, 1-(pyridin-3-yl)ethyl, 1-(methylsulfonylamino)ethyl, 1-(1-methyl-2-oxopiperidin-4-yl)ethyl, 1-(methylsulfonyl(N-ethyl)amino)ethyl, 1-(methylsulfonyl(N-methyl)amino)ethyl, 1-phenylethyl, 1-(methylcarbonyl(N-methyl)amino)ethyl, and 1-cyclopropylethyl As defined generally above and herein, each $R^7$ is independently selected from —($C_0$-$C_4$ alkylene)-$R^6$, —($C_0$-$C_4$ alkylene)-O—$R^6$, —S(O)$_2$—$R^8$, —C(=O)—$R^8$, —C(=O)—N($R^6$)$_2$, —($C_1$-$C_4$ alkylene)-O—C(=O)—$R^8$ and —($C_0$-$C_4$ alkylene)-C(=O)—O—$R^6$; or two $R^7$ are taken together with the nitrogen atom to which they are commonly bound to form an optionally substituted heterocyclyl or heteroaryl, wherein $R^6$ and $R^8$ are as defined herein. In some embodiments, each $R^7$ is independently selected from —($C_0$-$C_4$ alkylene)-$R^6$, —S(O)$_2$—$R^8$, and —C(=O)—$R^8$. In a more specific aspect, each $R^7$ is independently selected from hydrogen, —$CH_3$, —$CH_2CH_3$, —S(O)$_2$—$CH_3$, and —C(O)$CH_3$.

As defined generally above and herein, $R^8$ is selected from $C_1$-$C_4$ alkyl, aryl, heteroaryl, carbocyclyl and heterocyclyl. In some embodiments, $R^8$ is $C_1$-$C_4$ alkyl. In some embodiments, $R^8$ is methyl. In some embodiments, $R^8$ is aryl. In some embodiments, $R^8$ is optionally substituted phenyl. In some embodiments, $R^8$ is unsubstituted phenyl. In some embodiments, $R^8$ is substituted phenyl. In some embodiments, $R^8$ is optionally substituted heteroaryl. In some embodiments, $R^8$ is carbocyclyl. In some embodiments, $R^8$ is optionally substituted heterocyclyl.

Unless otherwise designated, any alkyl, alkylene, alkenyl, alkenylene, alkynyl, alkynylene, aryl, heteroaryl, heterocyclyl or carbocyclyl portion of the compound is optionally substituted.

In some embodiments, the compound of formula I is represented by structural formula II:

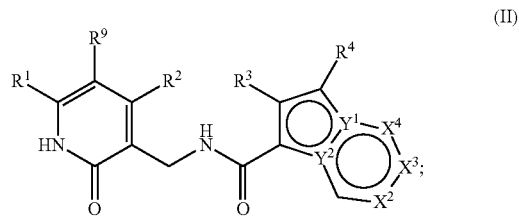

(II)

or a pharmaceutically acceptable salt or tautomer thereof, wherein:

each of $R^1$, $R^2$ and $R^9$ is independently selected from hydrogen, $C_1$-$C_4$ alkyl, and —O—($C_1$-$C_4$ alkyl);

one of $Y^1$ or $Y^2$ is N and the other is C;

one of $X^2$, $X^3$, or $X^4$ is N and each of the others is independently CH or —O—($C_1$-$C_4$ alkyl);

$R^3$ is selected from hydrogen, halo, and $C_1$-$C_4$ alkyl;

$R^4$ is selected from —C(O)—$R^8$, —($C_0$-$C_4$ alkylene)-$R^8$, and —($C_0$-$C_4$ alkylene)-N($R^7$)$_2$;

$R^7$ is selected from hydrogen, $C_1$-$C_4$ alkyl, —S(O)$_2$—$C_1$-$C_4$ alkyl, and —C(=O)—$C_1$-$C_4$ alkyl; or two $R^7$ are taken together with the nitrogen atom to which they are commonly bound to form an optionally substituted heterocyclyl; and $R^8$ is selected from $C_1$-$C_4$ alkyl, aryl, heteroaryl, carbocyclyl and heterocyclyl, wherein each of the aryl, heteroaryl, carbocyclyl and heterocyclyl are optionally substituted.

In some embodiments, in the compound of formula II, $R^7$ is selected from hydrogen, $C_1$-$C_4$ alkyl, —S(O)$_2$—$C_1$-$C_4$ alkyl, and —C(=O)—$C_1$-$C_4$ alkyl; or two $R^7$ are taken together with the nitrogen atom to which they are commonly bound to form an optionally substituted morpholinyl or piperizinyl; and $R^8$ is selected from $C_1$-$C_4$ alkyl, optionally substituted phenyl, optionally substituted cyclopropyl, optionally substituted pyrazolyl, optionally substituted pyridinyl, optionally substituted pyridinyl-2(1H)-one, optionally substituted tetrahydropyranyl, optionally substituted isoxazolyl, and optionally substituted piperidinyl.

In some embodiments, in the compound of formula II, $R^1$ is $C_1$-$C_4$ alkyl; $R^9$ is hydrogen; $R^2$ is $C_1$-$C_4$ alkyl or —O—($C_1$-$C_4$ alkyl); the optional substituents present on the optionally substituted groups for $R^8$ are selected independently from one or two groups selected from $C_1$-$C_4$ alkyl, $R^†$, $C_1$-$C_4$ alkyl-OH, —SO$_2$—$C_1$-$C_4$ alkyl, and —C(O)$R^†$; and $R^†$ is $C_1$-$C_4$ alkyl substituted by one or more fluoro.

It will be understood by those of skill in the art that the compounds of the invention are limited to compounds that are stable.

Unless otherwise stated, all tautomeric forms of the compounds of the invention are within the scope of the invention.

Exemplary compounds of formula I are set forth below in Table 1. In some cases two (or more) of the compounds in Table 1 having one (or more) wavy bonds will have the exact same structure. Because the wavy bond represents a chiral center of undetermined optical rotation, such compounds will be understood to be separate and distinct optical isomers of one another. Table 1 is annotated to indicate those sets of two or more compounds that have the same depicted structure, but are of different stereochemistry.

US 9,745,305 B2
TABLE 1
Exemplary Compounds of Formula I.
| Compound No. | Structure |
|---|---|
| 100 | 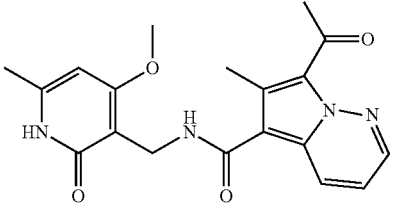 [SMILES: COc1cc(C)[nH]c(=O)c1CNC(=O)c1c(C)c(C(C)=O)n2ncccc12] |
| 101 | 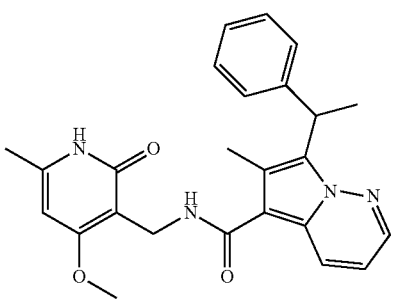 [SMILES: COc1cc(C)[nH]c(=O)c1CNC(=O)c1c(C)c(C(C)c2ccccc2)n2ncccc12] |
| 102 | 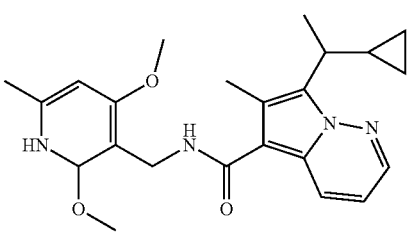 [SMILES: COC1=C(CNC(=O)c2c(C)c(C(C)C3CC3)n3ncccc23)C(OC)NC(C)=C1] |
| 103 | 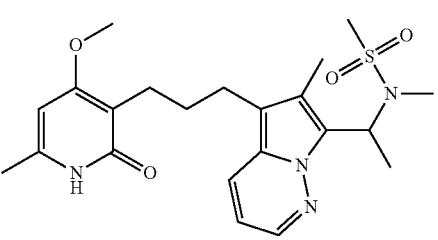 |
| 104 | 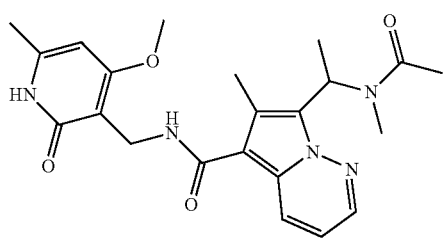 [SMILES: COc1cc(C)[nH]c(=O)c1CNC(=O)c1c(C)c(C(C)N(C)C(C)=O)n2ncccc12] |
| 105* | 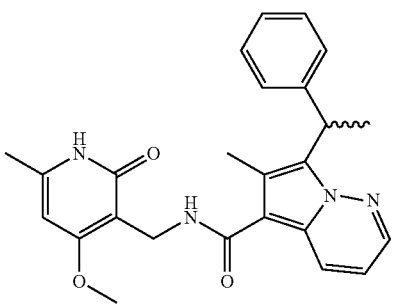 [SMILES: COc1cc(C)[nH]c(=O)c1CNC(=O)c1c(C)c(C(C)c2ccccc2)n2ncccc12] |

15
TABLE 1-continued
Exemplary Compounds of Formula I.
| Compound No. | Structure |
| --- | --- |
| 106* | 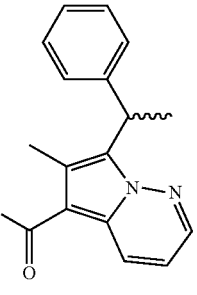 |
| 107** | 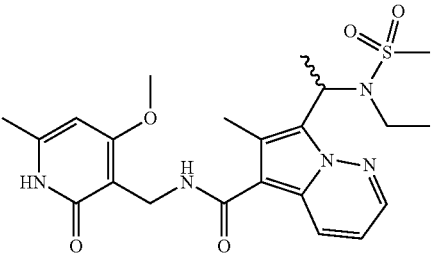 |
| 108** | 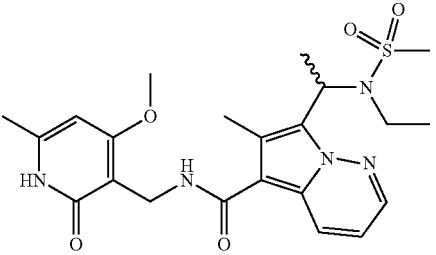 |
| 109 | 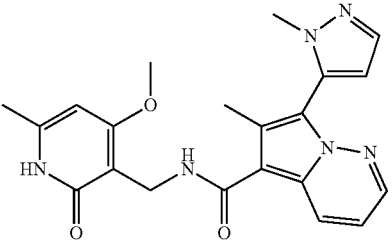 [SMILES: COc1cc(C)[nH]c(=O)c1CNC(=O)c1c(C)c(-c2ccnn2C)n2ncccc12] |
| 110 | 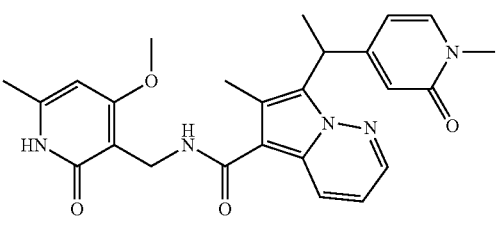 |
| 111 | 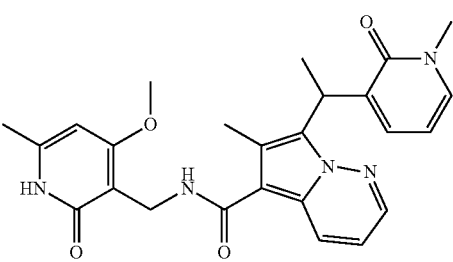 |

TABLE 1-continued

Exemplary Compounds of Formula I.

| Compound No. | Structure |
| --- | --- |
| 112 | 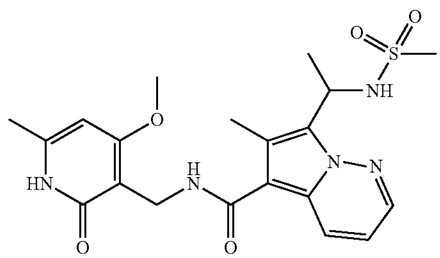 |
| 113 | 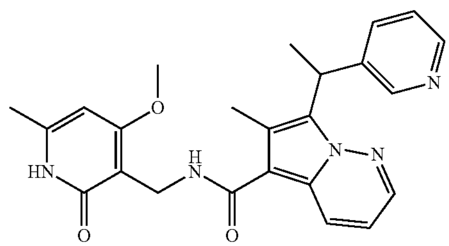 [SMILES: COc1cc(C)[nH]c(=O)c1CNC(=O)c1c(C)c(C(C)c2cccnc2)n2ncccc12] |
| 114 | 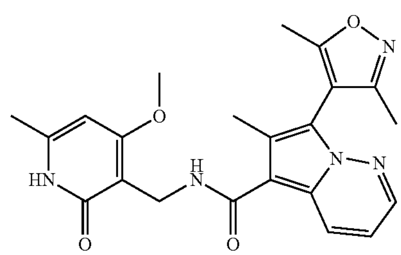 |
| 115 | 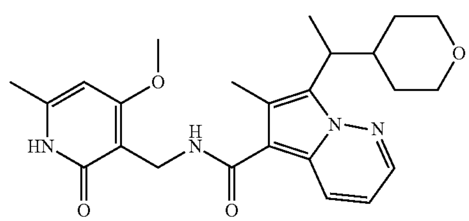 [SMILES: COc1cc(C)[nH]c(=O)c1CNC(=O)c1c(C)c(C(C)C2CCOCC2)n2ncccc12] |
| 116 | 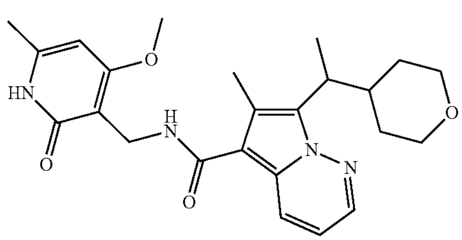 [SMILES: COc1cc(C)[nH]c(=O)c1CNC(=O)c1c(C)c(C(C)C2CCOCC2)n2ncccc12] |
| 117 | 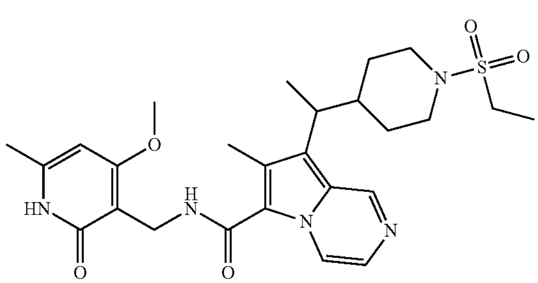 [SMILES: CCS(=O)(=O)N1CCC(C(C)c2c(C)c(C(=O)NCc3c(OC)cc(C)[nH]c3=O)n3ccncc23)CC1] |

TABLE 1-continued
Exemplary Compounds of Formula I.
| Compound No. | Structure |
|---|---|
| 118 | 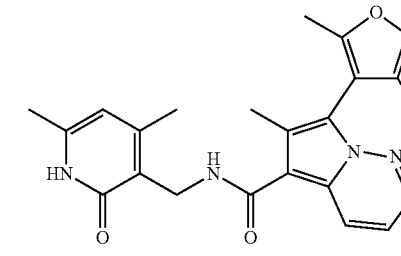 |
| 119 | 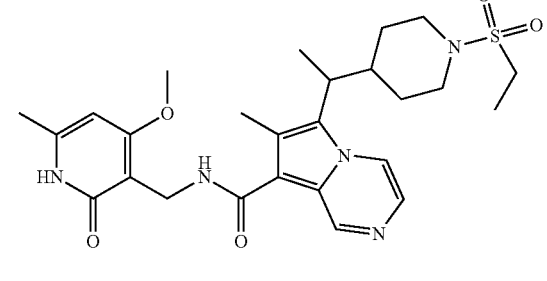 |
| 120 | 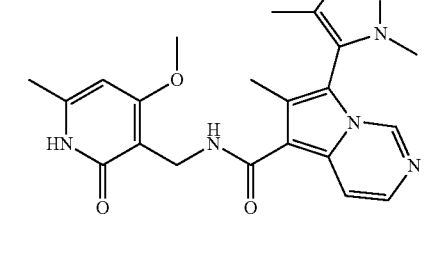 |
| 121 | 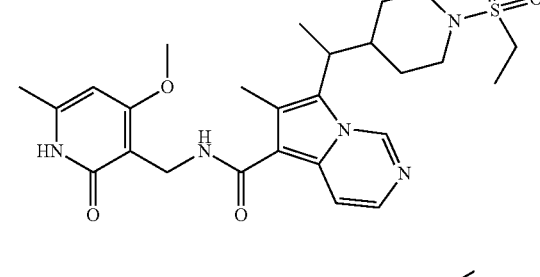 |
| 122 | 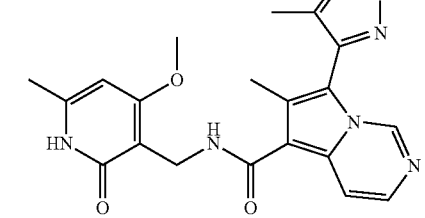 |

TABLE 1-continued

Exemplary Compounds of Formula I.

| Compound No. | Structure |
|---|---|
| 123 | 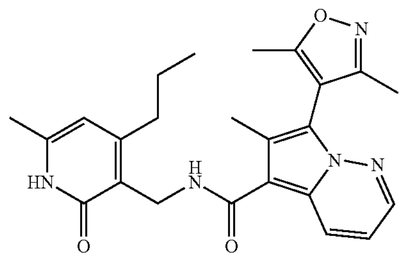 |
| 124 | 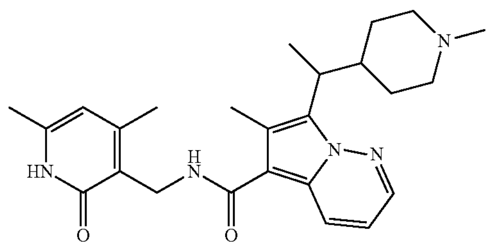 |
| 125 | 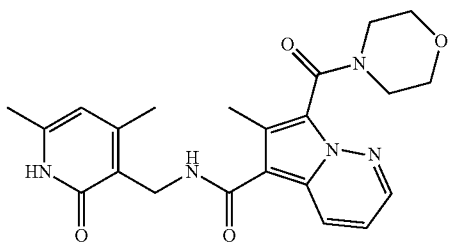 [SMILES: Cc1cc(C)c(CNC(=O)c2c(C)c(C(=O)N3CCOCC3)n3ncccc23)c(=O)[nH]1] |
| 126 | 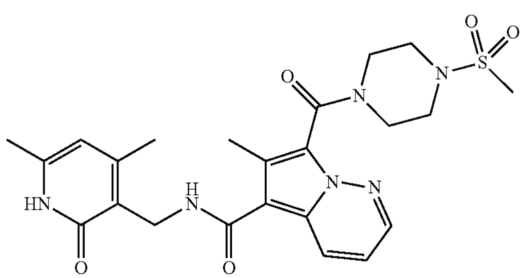 [SMILES: Cc1cc(C)c(CNC(=O)c2c(C)c(C(=O)N3CCN(S(C)(=O)=O)CC3)n3ncccc23)c(=O)[nH]1] |
| 127 | 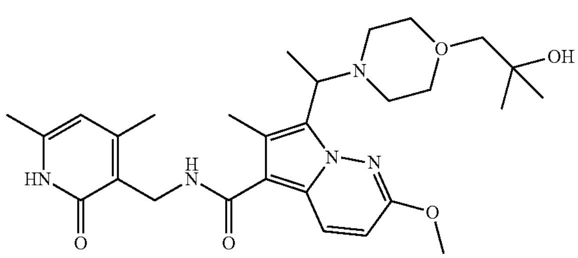 |
| 128 | 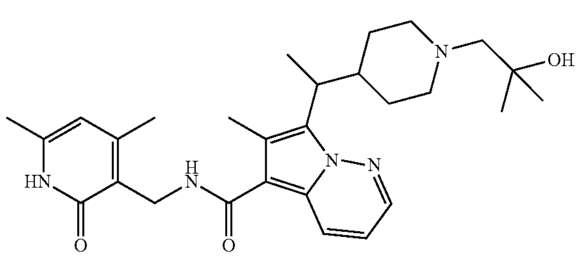 [SMILES: Cc1cc(C)c(CNC(=O)c2c(C)c(C(C)C3CCN(CC(C)(C)O)CC3)n3ncccc23)c(=O)[nH]1] |

US 9,745,305 B2
23
TABLE 1-continued
Exemplary Compounds of Formula I.
| Compound No. | Structure |
|---|---|
| 129 | 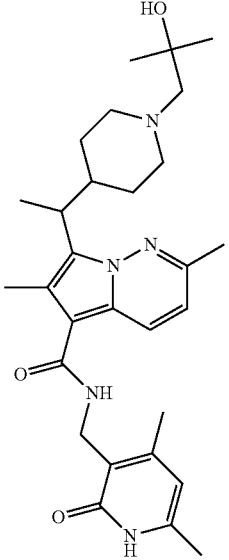 |
| 130 | 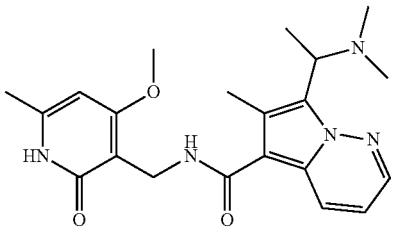 [SMILES: COc1cc(C)[nH]c(=O)c1CNC(=O)c1c(C)c(C(C)N(C)C)n2ncccc12] |
| 131 | 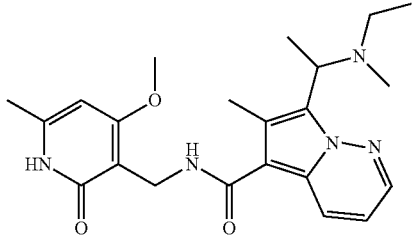 [SMILES: CCN(C)C(C)c1c(C)c(C(=O)NCc2c(OC)cc(C)[nH]c2=O)c2cccnn12] |
| 132 | 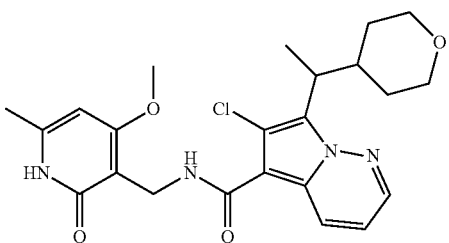 [SMILES: COc1cc(C)[nH]c(=O)c1CNC(=O)c1c(Cl)c(C(C)C2CCOCC2)n2ncccc12] |

TABLE 1-continued
Exemplary Compounds of Formula I.
| Compound No. | Structure |
|---|---|
| 133 | 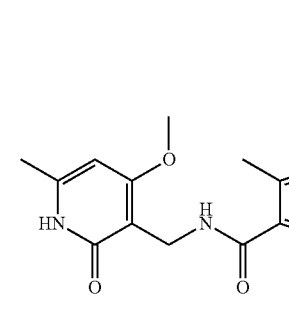 |
| 134 | 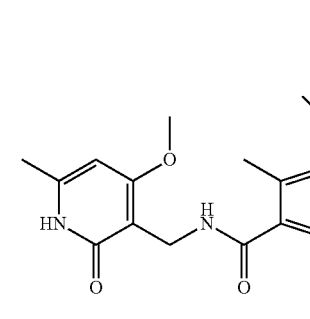 |
| 135 | 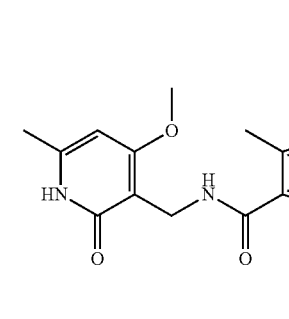 |
| 136 | 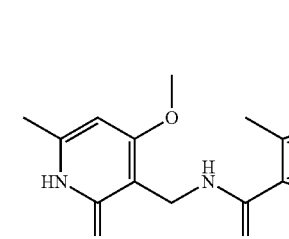 |

TABLE 1-continued

Exemplary Compounds of Formula I.

| Compound No. | Structure |
|---|---|
| 137 | 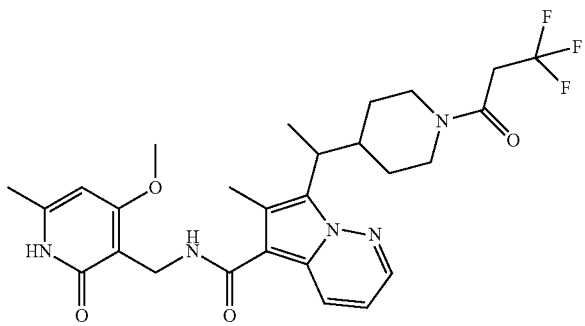 [SMILES: COc1cc(C)[nH]c(=O)c1CNC(=O)c1c(C)c(C(C)C2CCN(C(=O)CC(F)(F)F)CC2)n2ncccc12] |
| 138 | 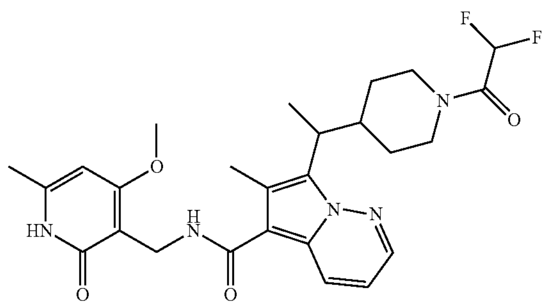 [SMILES: COc1cc(C)[nH]c(=O)c1CNC(=O)c1c(C)c(C(C)C2CCN(C(=O)C(F)F)CC2)n2ncccc12] |
| 139 | 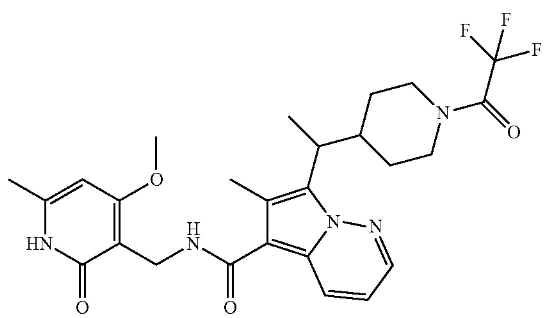 [SMILES: COc1cc(C)[nH]c(=O)c1CNC(=O)c1c(C)c(C(C)C2CCN(C(=O)C(F)(F)F)CC2)n2ncccc12] |
| 140 | 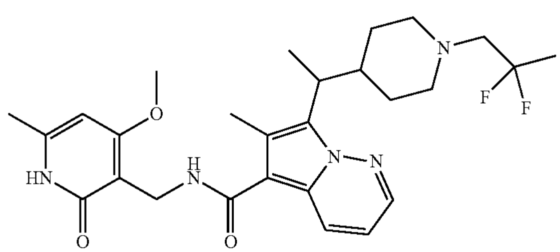 [SMILES: COc1cc(C)[nH]c(=O)c1CNC(=O)c1c(C)c(C(C)C2CCN(CC(C)(F)F)CC2)n2ncccc12] |
| 141 | 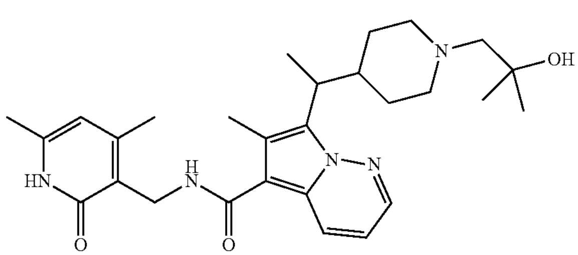 [SMILES: Cc1cc(C)c(CNC(=O)c2c(C)c(C(C)C3CCN(CC(C)(C)O)CC3)n3ncccc23)c(=O)[nH]1] |

TABLE 1-continued

Exemplary Compounds of Formula I.

| Compound No. | Structure |
|---|---|
| 142 | [structure] |
| 143 | [structure] |
| 144 | [structure] |
| 145 | [structure] |

*Compounds 105 and 106 are isolated enantiomers of one another whose optical rotation has not been determined.
**Compounds 107 and 108 are isolated enantiomers of one another whose optical rotation has not been determined.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate a histone methyl modifying enzyme, or a mutant thereof, in a biological sample or in a patient. In certain embodiments, the amount of compound in compositions of this invention is such that is effective to measurably modulate a histone methyl modifying enzyme, or a mutant thereof, in a biological sample or in a patient.

In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the modulating of activity of one or more enzymes involved in epigenetic regulation and in particular EZH1 and EZH2 and, even more specifically EZH2 and mutant forms thereof. In some embodiments, compounds of the present invention down-regulate or suppress the activity of EZH2. In some embodiments, compounds of the present invention are antagonists of EZH2 activity. In some embodiments, compounds of the present invention down-regulate or suppress the activity of EZH1. In some embodiments, compounds of the present invention are antagonists of EZH1 activity.

In some embodiments, compounds and compositions of the present invention are useful in treating diseases and/or disorders associated with overexpression of EZH1 or EZH2 and/or expression of a mutant form of EZH2, particularly those mutant forms that alter EZH2 substrate activity. The study of EZH2 deletions, missense and frameshift mutations suggest that EZH2 functions as a tumor suppressor in blood disorders such as myelodysplastic syndromes (MDS) and myeloid malignancies (Ernst et al., Nat Genet. 2010 August; 42(8):722-6; Nikoloski et al., Nat Genet. 2010 August; 42(8):665-7). In some embodiments, compounds and compositions of the present invention are useful in treating diseases and/or disorders associated with the presence of EZH2 having a Y641N, Y641C, Y641F, Y641H, Y641S, A677G, or A687 mutation. In a particular aspect of this embodiment, the EZH2 has a VY641N mutation.

In some embodiments, the present invention provides a method of treating a subject suffering from a disease and/or disorder associated with overexpression of EZH1 or EZH2 and/or expression of a mutant form of EZH2 comprising the step of administering a compound or composition of formula I. In some embodiments, the above method additionally comprises the preliminary step of determining if the subject is overexpressing EZH2 or expressing a mutant form of EZH2.

In some embodiment, the present invention the disease or disorder associated with the presence of a mutant form of EZH2 is a human B cell lymphoma. In some embodiments, the disease and/or disorder associated with the presence of Y641N EZH2 is follicular lymphoma or diffuse large-B-cell lymphoma. In some embodiments, compounds or compositions of the present invention are useful in treating blood disorders, such as myelodysplastic syndromes, leukemia, anemia and cytopenia. Sneeringer et al., "Coordinated activities of wild-type plus mutant EZH2 drive tumor-associated hypertrimethylation of lysine 27 on histone H3 (H3K27) in human B-cell lymphomas," Proceedings of the National Academy of Sciences, PNAS Early Edition published ahead of print on Nov. 15, 2010.

In some embodiments, compounds and compositions of the present invention are useful in treating diseases and/or disorders associated with cellular proliferation. In some embodiments, compounds and compositions of the present invention are useful in treating diseases and/or disorders associated with misregulation of cell cycle or DNA repair. In some embodiments, compounds and compositions of the present invention are useful in treating cancer. Exemplary types of cancer include breast cancer, prostate cancer, colon cancer, renal cell carcinoma, glioblastoma multiforme cancer, bladder cancer, melanoma, bronchial cancer, lymphoma and liver cancer.

In some embodiments, the present invention provides a method of reducing the activity of EZH2 in a subject comprising the step of administering a compound or composition of formula I. In some embodiments, the present invention provides a method of reducing the activity of wide-type EZH2 in a subject comprising the step of administering a compound or composition of formula I. In some embodiments, the present invention provides a method of reducing the activity of wild-type EZH1 in a subject comprising the step of administering a compound or composition of formula I. In some embodiments, the present invention provides a method of reducing the activity of a mutant form of EZH2 in a subject comprising the step of administering a compound or composition of formula I. In some embodiments, the present invention provides a method of reducing the activity of a mutant form of EZH2 in a subject comprising the step of administering a compound or composition of formula I, wherein the mutant form of EZH2 is selected from Y641N, Y641C, Y641F, Y641H, Y641S, A677G, or A687V EZH2. Each of these mutations alter the EZH2 substrate activity, and thus facilitate the conversion from a di- to a tri-methylated K27 state. In a more specific aspect, the present invention provides a method of reducing the activity of a mutant form of EZH2 in a subject comprising the step of administering a compound or composition of formula I, wherein the mutant form of EZH2 is Y641N EZH2.

In some embodiments, the present invention provides a method of treating a subject suffering from a disease and/or disorder associated with EZH2, wherein the method additionally comprises the preliminary step of determining if the subject is expressing a mutant form of EZH2, such as Y641N, Y641C, Y641F, Y641H, Y641S, A677G, or A687V EZH2. In some embodiments, the present invention provides a method of reducing the activity of a mutant form of EZH2, such as Y641N, Y641C, Y641F, Y641H, Y641S, A677G, or A687V EZH2, in a subject in need thereof comprising the step of administering a compound or composition of formula I. In some embodiments, the present invention provides a method of treating a subject suffering from a disease and/or disorder associated with EZH2, wherein the method additionally comprises the preliminary step of determining if the subject has increased levels of histone H3 Lys-27-specific trimethylation (H3K27me3), as compared to a subject known not to express a mutant form of EZH2.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples that follow and the references to the scientific and patent literature cited herein. It should further be appreciated that the contents of those cited references are incorporated herein by reference to help illustrate the state of the art.

It will be appreciated that for compound preparations described herein, when reverse phase HPLC is used to purify a compound, a compound may exist as an acid addition salt. In some embodiments, a compound may exist as a formic acid or mono-, di-, or tri-fluoroacetic acid salt.

It will further be appreciated that the present invention contemplates individual compounds described herein. Where individual compounds exemplified are isolated and/or characterized as a salt, for example, as a trifluoroacetic acid salt, the present invention contemplates a free base of the salt, as well as other pharmaceutically acceptable salts of the free base.

The following examples contain important additional information, exemplification and guidance that can be adapted to the practice of this invention in its various embodiments and the equivalents thereof

EXAMPLES

As depicted in the Examples below, in certain exemplary embodiments, compounds are prepared according to the following general procedures. It will be appreciated that, although the synthetic methods and Schemes depict the synthesis of certain compounds of the present invention, the following methods and other methods known to one of ordinary skill in the art can be applied to all compounds and subclasses and species of each of these compounds, as described herein.

Unless otherwise noted, all solvents, chemicals, and reagents were obtained commercially and used without purification. The $^1$H NMR spectra were obtained in $CDCl_3$, $d_6$-DMSO, $CD_3OD$, or $d_6$-acetone at 25° C. at 300 MHz on an OXFORD (Varian) with chemical shift (δ, ppm) reported relative to TMS as an internal standard. HPLC-MS chromatograms and spectra were obtained with Shimadzu LC-MS-2020 system. Chiral analysis and purification were obtained with Yilite P270.

Example 1

Synthesis of 5-(bromomethyl)-1-methyl-1H-pyrazole (Intermediate 1A)

Step 1: methyl 1-methyl-1H-pyrazole-5-carboxylate

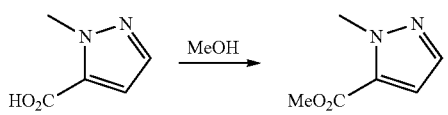

To a stirred solution of 1-methyl-1H-pyrazole-5-carboxylic acid (5 g, 39.7 mmol) in methanol (100 mL) was added thionyl chloride (103.2 mmol) under argon atmosphere at 0° C. The reaction mixture was stirred to room temperature over 12 h. The reaction mixture was conc. in vacuo, then diluted with water (100 mL), carefully quenched with sat'd aqueous $NaHCO_3$, and extracted with ethyl acetate (100 mL×3). The combined organic phase was dried with anhydrous sodium sulphate, filtered and the filtrate was concentrated to give afford the title compound as a white solid which was used without further purification (5 g, 90%) m/z 240.

Step 2: (1-methyl-1H-pyrazol-5-yl)methanol

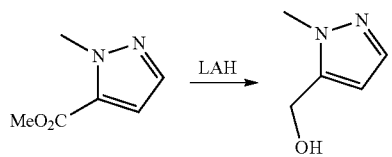

To a stirred solution of methyl 1-methyl-1H-pyrazole-5-carboxylate (3 g, 21.4 mmol) in tetrahydrofuran (50 mL) at 0° C. was added lithium aluminum hydride (977 mg, 25.7 mmol). The mixture was stirred at room temperature for 12 h. The reaction was quenched by adding water, extracted with ethyl acetate (100 mL), dried, concentrated and the residue was purified by column chromatography on silica gel (petroleum ether/acetic ester=10:1), to afford the title compound as an off-white oil (2 g, 83.3%).

The examples shown in the following table were prepared according to the procedure described in Steps 1 and 2 of this Example using the appropriate starting materials and modifications.

| Structure | Name | LCMS |
|---|---|---|
| 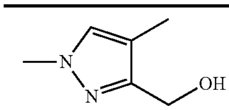 | (1,4-dimethyl-1H-pyrazol-3-yl)methanol | 126 |
| 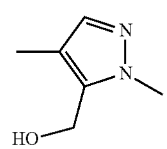 | (1,4-dimethyl-1H-pyrazol-5-yl)methanol | 126 |

Step 3: 5-(bromomethyl)-1-methyl-1H-pyrazole

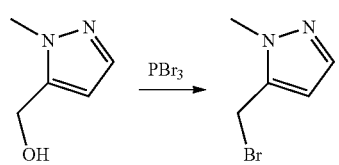

To a solution of (1-methyl-1H-pyrazol-5-yl)methanol (500 mg, 4.46 mmol) in anhydrous dichloromethane (20 mL) was added $PBr_3$ (1.21 g, 4.46 mmol) at 0° C. The mixture was purged with nitrogen and stirred at room temperature for 12 h. The reaction mixture was adjusted to pH ~8.5 with saturated aqueous sodium bicarbonate, and then was extracted with dichloromethane (10 mL×3). The combined organic phase was dried by anhydrous sodium sulphate, filtered and concentrated. The residue was purified by preparative TLC (petroleum ether/acetic ester=5:1) to afford the title compound an off-white oil (500 mg, 64%) m/z 174.

The intermediates shown in the following table were prepared according to the procedure described in Step 3 of this Example using the appropriate starting materials and modifications.

| Intermediate | Structure | Name | LCMS |
|---|---|---|---|
| 1B | 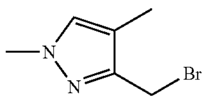 | 3-(bromomethyl)-1,4-dimethyl-1H-pyrazole | 190 |
| 1C | 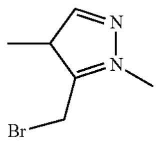 | 5-(bromomethyl)-1,4-dimethyl-1H-pyrazole | 190 |

The bromoalkyl products made using the procedures set forth in this example are employed as starting materials for the syntheses set forth in Example 4.

Example 2

Synthesis of 3-(2-bromoacetyl)pyridin-2(1H)-one (Intermediate 1D)

Step 1: N,2-dimethoxy-N-methylnicotinamide

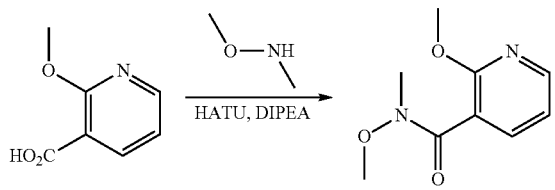

A mixture of 2-methoxynicotinic acid (3.5 g, 22.86 mmol), N,O-dimethylhydroxylamine (2.09 g, 34.28 mmol), HATU (13.04 g, 34.28 mmol) and Hunig's Base (8.86 g, 68.57 mmol) in dichloromethane (50 mL) was stirred at room temperature for overnight. The reaction was then conc. in vacuo and the residue was partitioned between water (20 mL) and ethyl acetate (20 mL), the organic layer was dried and concentrated to afford the crude title compound as a yellow solid which was used directly without further purification (3 g, 67% yield).

Step 2: 1-(2-methoxypyridin-3-yl)ethanone

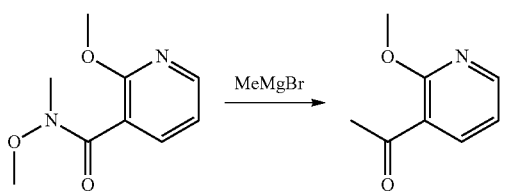

To a solution of N,2-dimethoxy-N-methylnicotinamide (3 g, 0.19 mmol) in tetrahydrofuran (30 mL) was added methylmagnesium bromide (1M solution in tetrahydrofuran, 30.58 mL, 30.58 mmol) at 0° C. The mixture was stirred at 0° C. to room temperature overnight. The reaction was then quenched with water and extracted with ethyl acetate. The organic layer was dried with MgSO$_4$, filtered and concentrated to afford the crude title compound which was used directly in the next step (1.2 g yellow oil, 52% yield).

The intermediates shown in the following table were prepared according to the procedure described in Steps 1 and 2 of this Example using the appropriate starting materials and modifications.

| Structure | Name | LCMS |
|---|---|---|
| 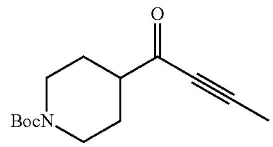 [SMILES: CC#CC(=O)C1CCN(C(=O)OC(C)(C)C)CC1] | tert-butyl 4-(but-2-ynoyl)piperidine-1-carboxylate | 252 |

Step 3: 3-(2-bromoacetyl)pyridin-2(1H)-one

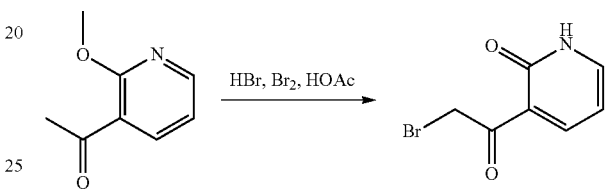

To a solution of 1-(2-methoxypyridin-3-yl)ethanone (1 g, 6.62 mmol) in HBr/HOAc (30%, 20 mL) was added bromine (1.06 g, 6.62 mmol) at room temperature. The mixture was stirred at 60° C. for 4 h. It was then cooled to room temperature and methyl tert-butyl ether (20 mL) was added to the mixture. A precipitate formed which was collected via vacuum filtration, collected and dried in vacuo to afford the title compound as a yellow solid. (1 g, 70% yield).

The bromoalkyl products made using the procedures set forth in this example are employed as starting materials for the syntheses set forth in Example 4.

Example 3

Synthesis of 2-bromo-1-(tetrahydro-2H-pyran-4-yl)ethanone (Intermediate 1E)

Step 1: 2-diazo-1-(tetrahydro-2H-pyran-4-yl)ethanone

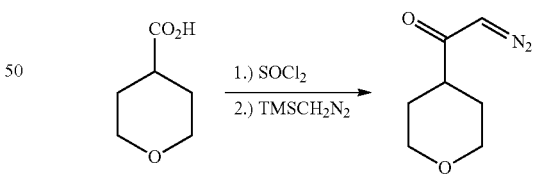

Tetrahydro-2H-pyran-4-carboxylic acid (10 g, 76.84 mmol) was added into a flask and thionyl chloride (20 mL, 275.7 mmol) was added drop wise at 0° C. The mixture was stir at this temp for 2 h and then the volatiles were removed under vacuum to afford the acid chloride which was directly dissolved in dichloromethane (5 mL) and (trimethylsilyl) diazomethane (22.8 g, 0.2 mol) was added drop wise at ° C. The mixture was stirred for 2 h affording the solution was used directly in the next step.

The intermediates shown in the following table were prepared according to the procedure described in Step 1 of this Example using the appropriate starting materials and modifications.

| Structure | Name | LCMS |
|---|---|---|
| (structure shown) | benzyl 4-(2-diazoacetyl)piperidine-1-carboxylate | 288 |

Step 2: 2-bromo-1-(tetrahydro-2H-pyran-4-yl)ethanone (reaction scheme: diazo compound → bromoketone using HBr/HOAc)

To a solution of 2-diazo-1-(tetrahydro-2H-pyran-4-yl) ethanone was added hydrogen bromide-acetic acid (5.6 g, 40 mmol) drop wise at −10° C. The mixture was allowed to warm to rt with stirring for 24 h. The reaction was then quenched with saturated aqueous sodium hydrogen carbonate and the mixture was extracted with dichloromethane (80 mL×3). The combined organic phase was dried over anhydrous sodium sulfate and then filtered. The filtrate was concentrated and the residue was purified by column chromatography on silica gel (eluent: petroleum ether/ethyl acetate=20/1) to afford the title compound as a brown crystalline solid (10.6 g, 66.6%).

The intermediates shown in the following table were prepared according to the procedure described in Step 2 of this Example using the appropriate starting materials and modifications.

| Intermediate | Structure | Name | LCMS |
|---|---|---|---|
| 1F | (structure shown) | benzyl 4-(2-bromoacetyl)piperidine-1-carboxylate | 341 |

The bromoalkyl products made using the procedures set forth in this example are employed as starting materials for the syntheses set forth in Example 4.

Example 4

Synthesis of methyl 7-(cyclopropanecarbonyl)-6-methylpyrrolo[1,2-b]pyridazine-5-carboxylate (Intermediate 4)

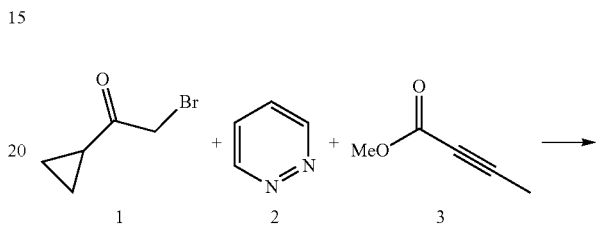

Methyl but-2-ynoate 3; (300 mg) was added to a solution of 2-bromo-1-cyclopropylethanone (1; 500 mg, 3.06 mmol) in 2-butyloxirane (5 mL) at room temperature. Pyridazine (2; 250 mg, 3.061 mmol) was then added slowly. The reaction mixture was refluxed at 60° C. overnight. The solvent was removed in vacuo to afford the crude product. The crude product was purified by silica gel chromatography (petroleum ether/ethyl acetate=1:1) to afford the title compound (120 mg, 9.6%).

The intermediates shown in the following table were prepared according to the procedure described in this example using the appropriate starting materials and modifications.

| Intermediate | Structure | Name | LCMS |
|---|---|---|---|
| 4A | (structure shown) | ethyl 6-methyl-7-(1-methyl-1H-pyrazol-5-yl)pyrrolo[1,2-b]pyridazine-5-carboxylate | 284 |

-continued

| Intermediate | Name | LCMS |
|---|---|---|
| 4B | ethyl 7-(1,4-dimethyl-1H-pyrazol-3-yl)-6-methylpyrrolo[1,2-b]pyridazine-5-carboxylate | 299 |
| 4C | ethyl 7-(1,4-dimethyl-1H-pyrazol-5-yl)-6-methylpyrrolo[1,2-b]pyridazine-5-carboxylate | 298 |
| 4D | ethyl 6-methyl-7-(2-oxo-1,2-dihydropyridine-3-carbonyl)pyrrolo[1,2-b]pyridazine-5-carboxylate | 326 |
| 4E | ethyl 6-methyl-7-(tetrahydro-2H-pyran-4-carbonyl)pyrrolo[1,2-b]pyridazine-5-carboxylate | 317 |
| 4F | ethyl 7-(1-((benzyloxy)carbonyl)piperidine-4-carbonyl)-6-methylpyrrolo[1,2-b]pyridazine-5-carboxylate | 450 |

-continued

| Intermediate | Structure | Name | LCMS |
|---|---|---|---|
| 4G | 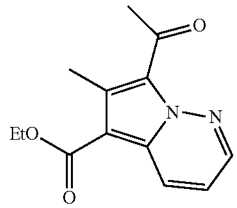 [SMILES: CCOC(=O)c1c(C)c(C(C)=O)n2ncccc12] | ethyl 7-acetyl-6-methylpyrrolo[1,2-b]pyridazine-5-carboxylate | 246 |
| 4H | 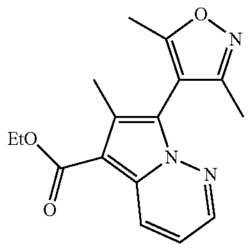 [SMILES: CCOC(=O)c1c(C)c(-c2c(C)noc2C)n2ncccc12] | ethyl 7-(3,5-dimethylisoxazol-4-yl)-6-methylpyrrolo[1,2-b]pyridazine-5-carboxylate | 299 |
| 4I | 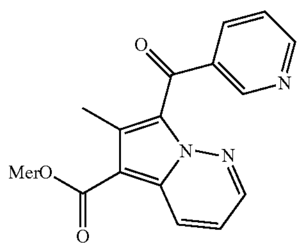 | methyl 6-methyl-7-nicotinoylpyrrolo[1,2-b]pyridazine-5-carboxylate | 296 |

Example 5

Synthesis of ethyl 6-methyl-7-(1-methyl-2-oxo-1,2-dihydropyridine-4-carbonyl)pyrrolo[1,2-b]pyridazine-5-carboxylate (Intermediate 4J)

Step 1: 4-acetyl-1-methylpyridin-2(1H)-one

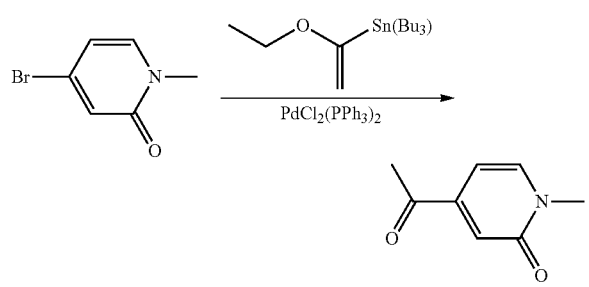

A mixture of tributyl(1-ethoxyvinyl)tin (11.41 g, 31.59 mmol), 4-bromo-1-methylpyridin-2(1H)-one (5.4 g, 28.72 mmol), bis(triphenylphosphine)palladium(II) chloride (201.59 mg, 287.20 µmol), and toluene (50 mL) was heated under nitrogen at 100° C. for 20 hours. After hydrolysis of the reaction mixture with 5% hydrochloric acid, the organic layer was extracted with acetic ether (30 mL×3), and dried over sodium sulfate. After evaporation of the solvent, column chromatography of the residue (silica gel; 100% Ethyl acetate) provided the title compound (3.5 g, yield: 80.62%).

Step 2: 4-(2-bromoacetyl)-1-methylpyridin-2(1H)-one

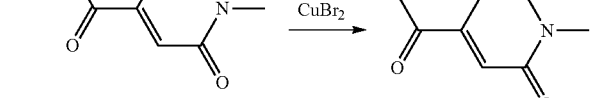

To a solution of 4-acetyl-1-methylpyridin-2(1H)-one (3.5 g, 23.15 mmol) in ethyl acetate (20 mL) and chloroform (20 mL) was added copper(II) bromide (10.34 g, 46.31 mmol). The mixture was stirred at 70° C. for 12 hours. The mixture was filtered, the filtrate was evaporated and purified via silica gel chromatography (80% PE/EA) to afford the title compound (1.5 g, yield, 28%).

Step 3: ethyl 6-methyl-7-(1-methyl-2-oxo-1,2-dihydropyridine-4-carbonyl)pyrrolo[1,2-b]pyridazine-5-carboxylate

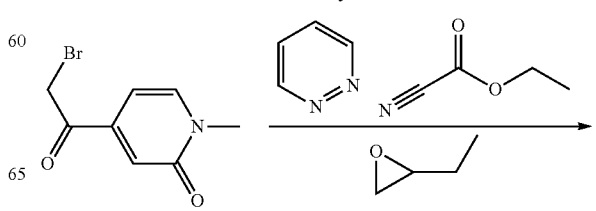

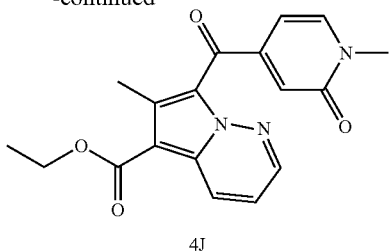

4J

A mixture of 4-(2-bromoacetyl)-1-methylpyridin-2(1H)-one (1.5 g, 6.52 mmol), ethyl but-2-ynoate (804 mg, 7.17 mmol), pyridazine (522 mg, 6.52 mmol), and 2-ethyloxirane (20 mL) was heated under nitrogen at 60° C. for 12 h. The mixture was evaporated and purified via silica gel chromatography (5% MeOH/DCM) to afford the title compound (500 mg, yield, 22.6%).

Example 6

Synthesis of ethyl 6-(1-((benzyloxy)carbonyl)piperidine-4-carbonyl)-7-methylpyrrolo[1,2-a]pyrazine-8-carboxylate (Intermediate 4K)

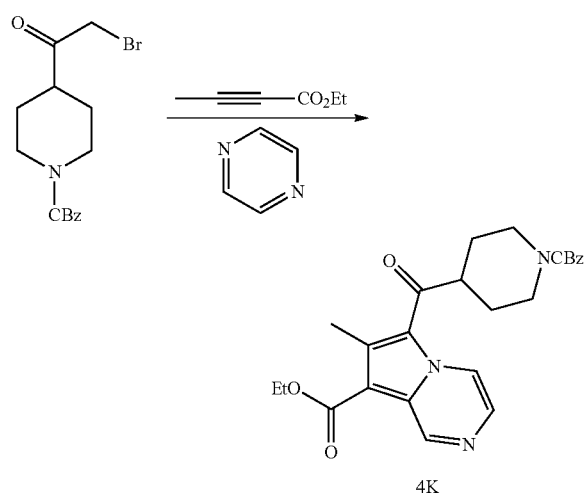

4K

To a solution of benzyl 4-(2-bromoacetyl)piperidine-1-carboxylate (8 g, 23.5 mmol) in (methylsulfinyl)methane (40 mL) were added ethyl but-2-ynoate (3.1 g, 28.2 mmol), pyrazine (2.2 g, 28.2 mmol) and potassium carbonate (9.7 g, 70.5 mmol). The reaction mixture was stirred at room temperature overnight. The reaction was then quenched by adding water (100 mL). The mixture was extracted with ethyl acetate. The organic layer was dried over sodium sulfate and concentrated to give the crude product and purified by column chromatography on silica gel (eluted: petrol ether/acetic ester 20:1→2:1) to afford the title compound (770 mg, 7.3%) as a yellow oil. m/z: calc'd 449.2; found 449.9.

The intermediates shown in the following table were prepared according to the procedure described in this Example using the appropriate starting materials and modifications.

| Method | Structure | Name | LCMS |
| --- | --- | --- | --- |
| Method 4L | 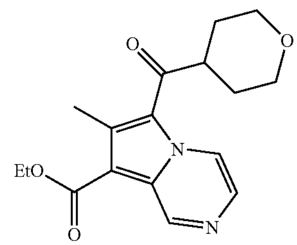 [SMILES: CCOC(=O)c1c(C)c(C(=O)C2CCOCC2)n2ccncc12] | ethyl 7-methyl-6-(tetrahydro-2H-pyran-4-carbonyl)-pyrrolo[1,2-a]pyrazine-8-carboxylate | 316 |

Example 7 ethyl 8-(1-(tert-butoxycarbonyl)piperidine-4-carbonyl)-7-methylpyrrolo[1,2-a]pyrazine-6-carboxylate (Intermediate 4M)

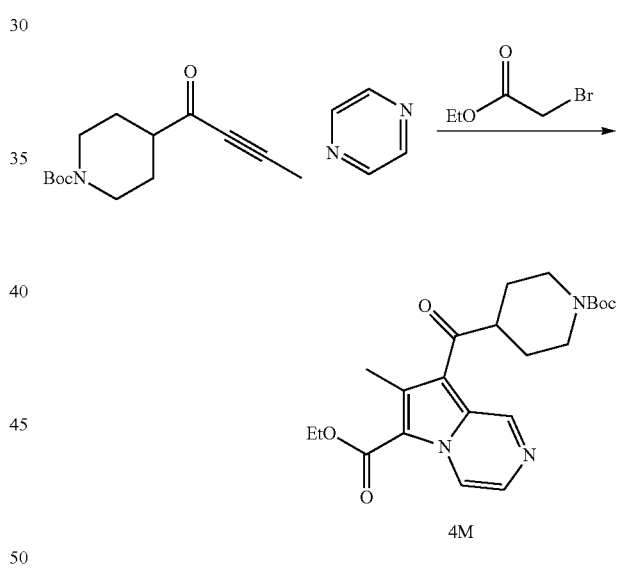

4M

To a solution of 1-(2-ethoxy-2-oxoethyl)pyrazin-1-ium bromide (11.9 g, 48 mmol) in (methylsulfinyl)methane (20 mL) was added tert-butyl 4-(but-2-ynoyl)piperidine-1-carboxylate (6 g, 23.9 mmol), and potassium carbonate (6.6 g, 48 mmol) followed. The resulting reaction mixture was allowed to stir for 2 hours at room temperature. The reaction mixture was washed with water and brine, extracted with acetic ester (100 mL×3). The combined organic phase was dried by anhydrous sodium sulphate, and then filtered. The filtrate was concentrated and purified by column chromatograph on silica gel (eluted: petrol ether/acetic ester 10:1→3:1→1:1) to afford the title compound (3 g, 31%) as an orange oil. LCMS (M+H+) m/z: calc'd. 415.21, found 415.9.

Example 8

Synthesis of methyl 7-(1-cyclopropyl-1-hydroxy-ethyl)-6-methylpyrrolo[1,2-b]pyridazine-5-carboxylate (Intermediate 6)

Step 1: methyl 7-(1-cyclopropyl-1-hydroxyethyl)-6-methylpyrrolo[1,2-b]pyridazine-5-carboxylate (Intermediate 5)

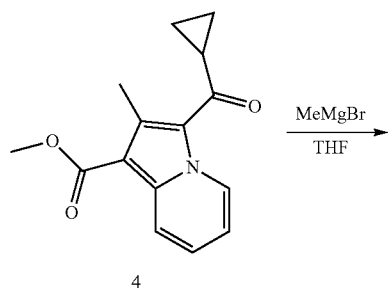

4

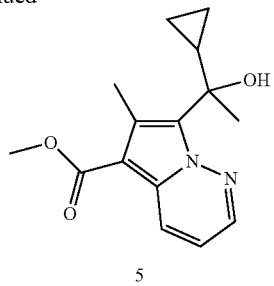

5

To a solution of 7-(cyclopropylmethyl)-6-methylpyrrolo[1,2-b]pyridazine-5-carboxylate (4; 110 mg, 0.43 mmol) in THF (1.5 mL) was added slowly a solution of methylmagnesium bromide (1.5 mL, 3 M in THF). The reaction mixture was stirred at −78° C. for 2 h. The mixture was then treated with sat'd aqueous $NH_4Cl$ (8 mL), and extracted with EtOAc (3×10 mL). The combined organic extract was dried ($Na_2SO_4$), filtered, and conc. in vacuo to afford the title compound 5 which was used without further purification (43 mg, 36%).

The intermediates shown in the following table were prepared according to the procedure described in Step 1 of this Example using the appropriate starting materials and modifications.

| Intermediate | Structure | Name | LCMS |
|---|---|---|---|
| 5A | 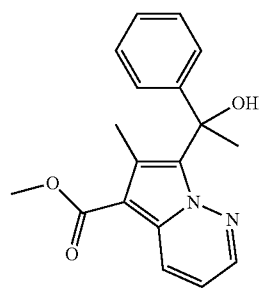 [SMILES: COC(=O)c1c(C)c(C(C)(O)c2ccccc2)n2ncccc12] | methyl 7-(1-hydroxy-1-phenylethyl)-6-methylpyrrolo[1,2-b]pyridazine-5-carboxylate | 310 |
| 5B | 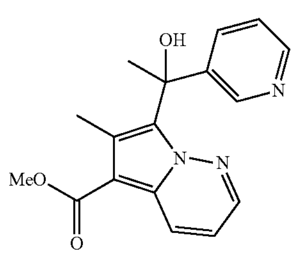 [SMILES: COC(=O)c1c(C)c(C(C)(O)c2cccnc2)n2ncccc12] | methyl 7-(1-hydroxy-1-(pyridine-3-yl)ethyl)-6-methylpyrrolo[1,2-b]pyridazine-5-carboxylate | 312 |
| 5C | 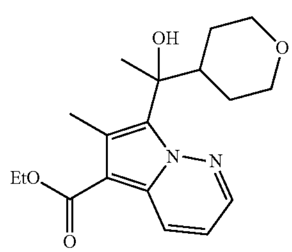 [SMILES: CCOC(=O)c1c(C)c(C(C)(O)C2CCOCC2)n2ncccc12] | ethyl 7-(1-hydroxy-1-(tetrahydro-2H-pyran-4-yl)ethyl)-6-methylpyrrolo[1,2-b]pyridazine-5-carboxylate | 333 |

-continued

| Intermediate | Structure | Name | LCMS |
|---|---|---|---|
| 5D | 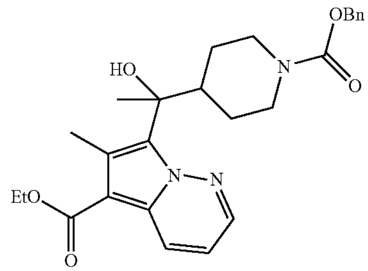 [SMILES: CCOC(=O)c1c(C)c(C(C)(O)C2CCN(C(=O)OCc3ccccc3)CC2)n2ncccc12] | ethyl 7-(1-(1-((benzyloxy)carbonyl)piperidin-4-yl)-1-hydroxyethyl)-6-methylpyrrolo[1,2-b]pyridazine-5-carboxylate | 466 |
| 5E | 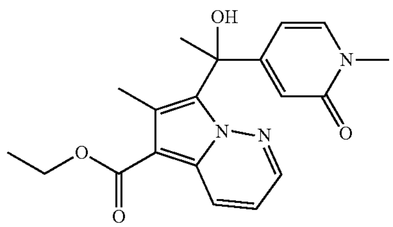 [SMILES: CCOC(=O)c1c(C)c(C(C)(O)c2ccn(C)c(=O)c2)n2ncccc12] | ethyl 7-(1-hydroxy-1-(1-methyl-2-oxo-1,2-methylpyrrolo[1,2-b]pyridazine-5-carboxylate | 356 |
| 5F | 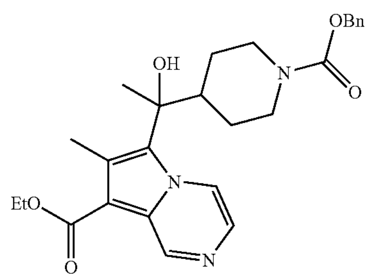 [SMILES: CCOC(=O)c1c(C)c(C(C)(O)C2CCN(C(=O)OCc3ccccc3)CC2)n2ccncc12] | ethyl 6-(1-(1-((benzyloxy)carbonyl)piperidin-4-yl)-1-hydroxyethyl)-7-methylpyrrolo[1,2-a]pyrazine-8-carboxylate | 465 |
| 5G | 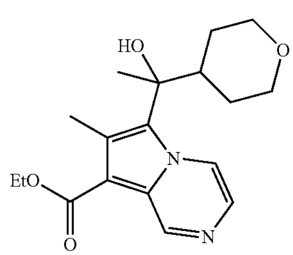 [SMILES: CCOC(=O)c1c(C)c(C(C)(O)C2CCOCC2)n2ccncc12] | ethyl 6-(1-hydroxy-1-(tetrahydro-2H-pyran-4-yl)ethyl)-7-methylpyrrolo[1,2-a]pyrazine-8-carboxylate | 333 |
| 5H | 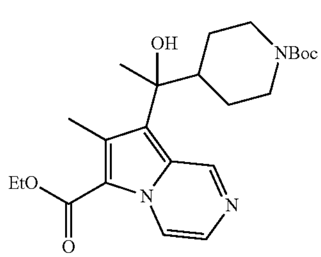 [SMILES: CCOC(=O)c1c(C)c(C(C)(O)C2CCN(C(=O)OC(C)(C)C)CC2)c2cnccn12] | ethyl 8-(1-(1-(tert-butoxycarbonyl)piperidin-4-yl)-1-hydroxyethyl)-7-methylpyrrolo[1,2-a]pyrazine-6-carboxylate | 431 |

Step 2: methyl 7-(1-cyclopropyl-1-hydroxyethyl)-6-methylpyrrolo[1,2-b]pyridazine-5-carboxylate (Intermediate 6)

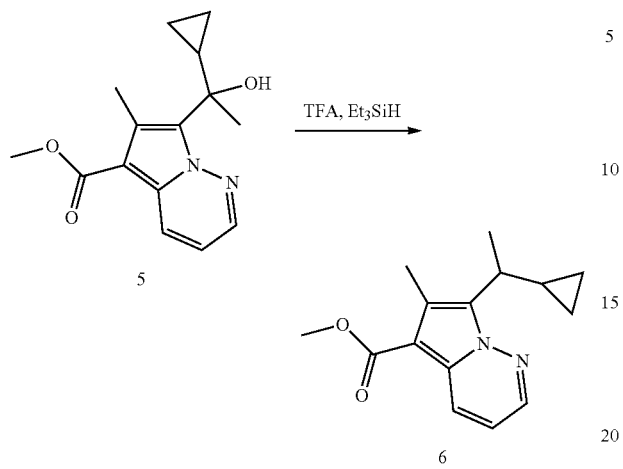

7-(Cyclopropylmethyl)-6-methylpyrrolo[1,2-b]pyridazine-5-carboxylate (5; 40 mg, 20 mg, 0.155 mmol) and Et₃SiH (0.171 mmol) were dissolved in THF (1.5 mL). Trifluoroacetic acid (1.55 mL) was then added to the reaction and the resulting mixture was stirred at room temperature overnight. The solvent was then removed in vacuo to afford the crude product which was purified via column chromatography on silica gel (petroleum ether/ethyl acetate=5:1) to afford the title compound 6 (18 mg, 45%).

The examples shown in the following table were prepared according to the procedure described in Step 2 of this Example using the appropriate starting materials and modifications.

| Intermediate | Structure | Name | LCMS |
|---|---|---|---|
| 6A | 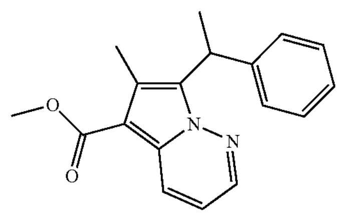 [SMILES: COC(=O)c1c(C)c(C(C)c2ccccc2)n2ncccc12] | methyl 6-methyl-7-(1-phenylethyl)pyrrolo[1,2-b]pyridazine-5-carboxylate | 294 |
| 6B | 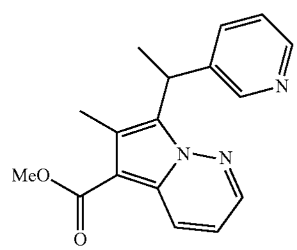 [SMILES: COC(=O)c1c(C)c(C(C)c2cccnc2)n2ncccc12] | methyl 6-methyl-7-(1-(42yridine-3-yl)ethyl)pyrrolo[1,2-b]pyridazine-5-carboxylate | 296 |
| 6C | 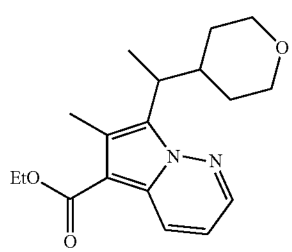 [SMILES: CCOC(=O)c1c(C)c(C(C)C2CCOCC2)n2ncccc12] | ethyl 6-methyl-7-(1-(tetrahydro-2H-pyran-4-yl)ethyl)pyrrolo[1,2-b]pyridazine-5-carboxylate | 317 |
| 6D | 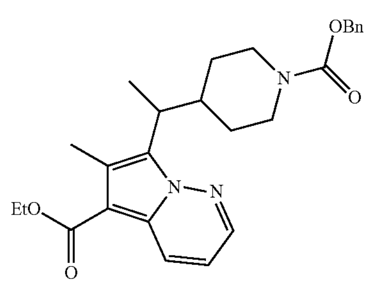 [SMILES: CCOC(=O)c1c(C)c(C(C)C2CCN(C(=O)OCc3ccccc3)CC2)n2ncccc12] | ethyl 7-(1-(1-((benzyloxy)carbonyl)piperidin-4-yl)ethyl)-6-methylpyrrolo[1,2-b]pyridazine-5-carboxylate | 450 |

| Intermediate | Structure | Name | LCMS |
|---|---|---|---|
| 6E | 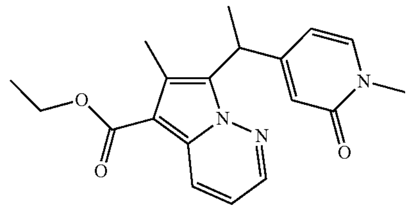 [SMILES: CCOC(=O)c1c(C)c(C(C)c2ccn(C)c(=O)c2)n2ncccc12] | ethyl 6-methyl-7-(1-(1-methyl-2-oxo-1,2-dihydropyridin-4-yl)ethyl)pyrrolo[1,2-b]pyridazine-5-carboxylate | 340 |
| 6F | 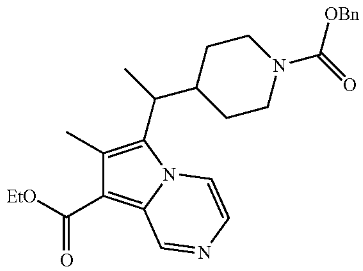 [SMILES: CCOC(=O)c1c(C)c(C(C)C2CCN(C(=O)OCc3ccccc3)CC2)n2ccncc12] | ethyl 6-(1-(1-((benzyloxy)carbonyl)piperidin-4-yl)ethyl)-7-methylpyrrolo[1,2-a]pyrazine-8-carboxylate | 450 |
| 6G | 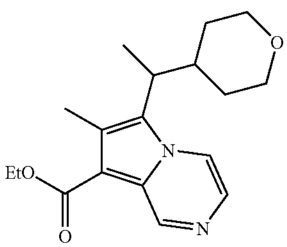 | ethyl 7-methyl-6-(1-(tetrahydro-2H-pyran-4-yl)ethyl)pyrrolo[1,2-a]pyrazine-8-carboxylate | 317 |
| 6H | 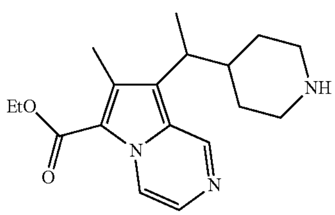 [SMILES: CCOC(=O)c1c(C)c(C(C)C2CCNCC2)c2cnccn12] | ethyl 7-methyl-8-(1-(piperidin-4-yl)ethyl)pyrrolo[1,2-a]pyrazine-6-carboxylate | 316 |

Example 9

Synthesis of ethyl 6-methyl-7-(1-(N-methylmethyl-sulfonamido)ethyl)pyrrolo[1,2-b]pyridazine-5-carboxylate (Intermediate 8)

Step 1: ethyl 6-methyl-7-(1-(methylamino)ethyl)pyrrolo[1,2-b]pyridazine-5-carboxylate

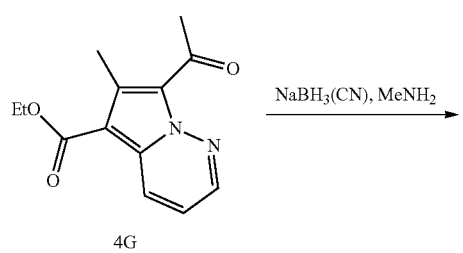

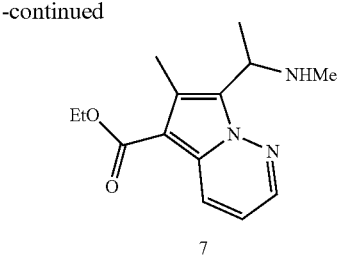

To a solution of ethyl 7-acetyl-6-methylpyrrolo[1,2-b]pyridazine-5-carboxylate (4G; 0.33 g, 1.34 mmol) in MeOH (50 mL) was added methylamine (30% in methanol, 0.42 g, 4.02 mmol) at room temperature. The mixture was stirred for one hour at room temperature before the addition of NaBH$_3$(CN) (0.18 g, 2.68 mmol). The reaction was then allowed to stir at ambient temperature for 12 h before the addition of 1 N HCl to adjust the pH ~3. The reaction was then extracted with MTBE. The remaining aqueous layer was then basified with 2N NaOH to pH ~11 and that was extracted with EtOAc. The organic extract was dried over Na$_2$SO$_4$ and concentrated in vacuo to afford the title compound as a pale yellow oil which was used without further purification (0.23 g, yield, 66%) m/z 261.

The intermediates shown in the following table were prepared according to the procedure described in Step 1 of this Example using the appropriate starting materials and modifications.

| Intermediate | Structure | Name | LCMS |
|---|---|---|---|
| 7A | 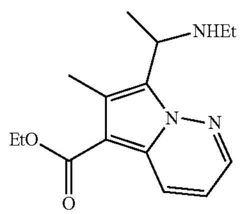 | ethyl 7-(1-(ethylamino)ethyl)-6-methylpyrrolo[1,2-b]pyridazine-5-carboxylate | 276 |
| 7B | 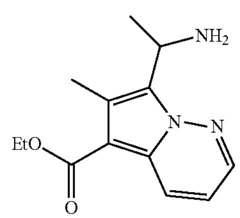 [SMILES: CCOC(=O)c1c(C)c(C(C)N)n2ncccc12] | ethyl 7-(1-aminoethyl)-6-methylpyrrolo[1,2-b]pyridazine-5-carboxylate | 248 |

Step 2: ethyl 6-methyl-7-(1-(N-methylmethylsulfonamido)ethyl)pyrrolo[1,2-b]pyridazine-5-carboxylate

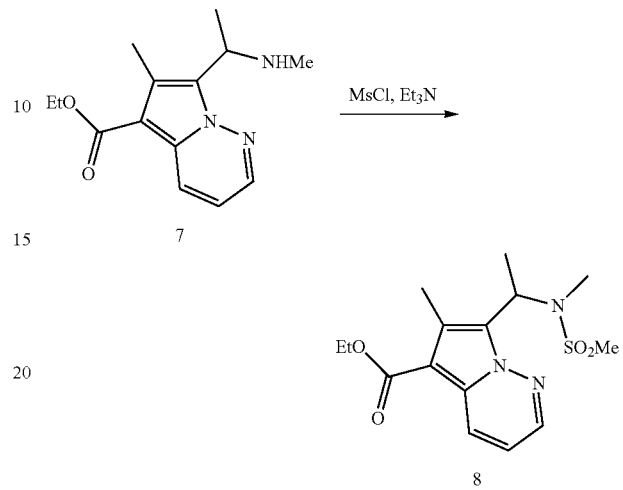

To a cooled (0° C.) and stirred solution of ethyl 6-methyl-7-(1-(methylamino)ethyl)-4a,7-dihydropyrrolo[1,2-b]pyridazine-5-carboxylate (0.22 g, 0.84 mmol) and triethylamine (0.42 g, 4.18 mmol) in DCM (5 mL) was added Ms-Cl (0.28 g, 2.51 mmol). The mixture was then allowed to stir overnight to room temperature. The reaction mixture was then conc. in vacuo and the resulting residue was purified via silica gel chromatography (eluent: PE/EtOAc=10:1) to the title compound as a yellow oil (0.27 g, yield 93%).

The intermediates shown in the following table were prepared according to the procedure described in Step 2 of this Example using the appropriate starting materials and modifications.

| Intermediate | Structure | Name | LCMS |
|---|---|---|---|
| 8A | 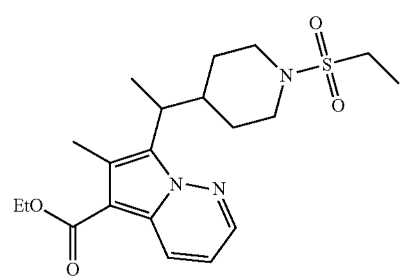 [SMILES: CCOC(=O)c1c(C)c(C(C)C2CCN(S(=O)(=O)CC)CC2)n2ncccc12] | ethyl 7-(1-(1-(ethylsulfonyl)piperidin-4-yl)ethyl)-6-methylpyrrolo[1,2-b]pyridazine-5-carboxylate | 408 |
| 8B | 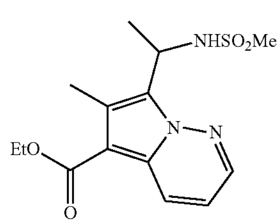 | ethyl 6-methyl-7-(1-(methylsulfonamido)ethyl)pyrrolo[1,2-b]pyridazine-5-carboxylate | 326 |

| Intermediate | Structure | Name | LCMS |
|---|---|---|---|
| 8C | 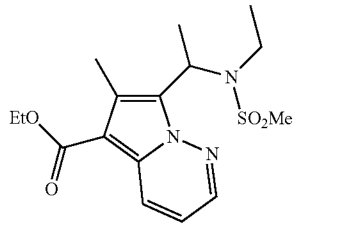 [SMILES: CCOC(=O)c1c(C)c(C(C)N(CC)S(C)(=O)=O)n2ncccc12] | ethyl 7-(1-(N-ethylmethylsulfonamido)ethyl)-6-methylpyrrolo[1,2-b]pyridazine-5-carboxylate | 354 |
| 8D | 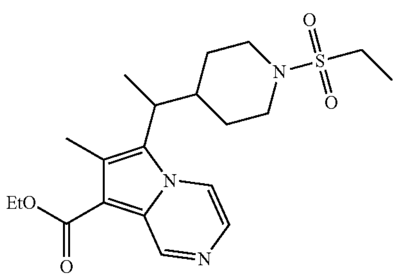 [SMILES: CCOC(=O)c1c(C)c(C(C)C2CCN(S(=O)(=O)CC)CC2)n2ccncc12] | ethyl 6-(1-(1-(ethylsulfonyl)piperidin-4-yl)ethyl)-7-methylpyrrolo[1,2-a]pyrazine-8-carboxylate | 408 |
| 8E | 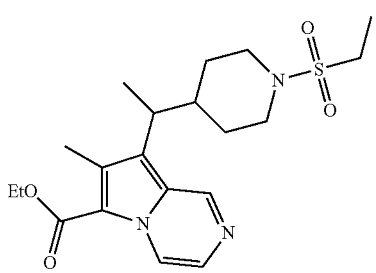 [SMILES: CCOC(=O)c1c(C)c(C(C)C2CCN(S(=O)(=O)CC)CC2)c2cnccn12] | ethyl 8-(1-(1-(ethylsulfonyl)piperidin-4-yl)ethyl)-7-methylpyrrolo[1,2-a]pyrazine-8-carboxylate | 408 |

Example 10

Synthesis of ethyl 6-methyl-7-(1-(1-methyl-2-oxo-1,2-dihydropyridin-3-yl)ethyl)pyrrolo[1,2-b]pyridazine-5-carboxylate (Intermediate 11)

Step 1: ethyl 6-methyl-7-(1-methyl-2-oxo-1,2-dihydropyridine-3-carbonyl)pyrrolo[1,2-b]pyridazine-5-carboxylate (9)

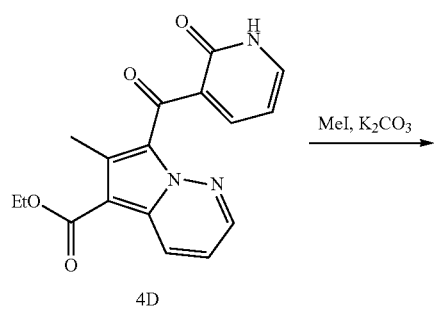

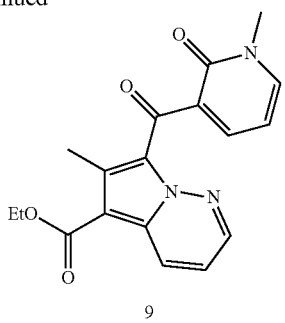

To a solution of ethyl 6-methyl-7-(2-oxo-1,2-dihydropyridine-3-carbonyl)pyrrolo[1,2-b]pyridazine-5-carboxylate ethyl (4D; 75 mg, 0.23 mmol) and potassium carbonate (63 mg, 0.46 mmol) in anhydrous MeCN (2 mL) was added methyl iodide (49 mg, 0.35 mmol). The reaction was warmed to 50° C. with stirring for 2 h before being allowed to cool to rt. The reaction mixture was then filtered and the filtrate was conc. in vacuo to afford the title compound which was used directly in the next step without purification.

The intermediate shown in the following table were prepared according to the procedure described in Step 1 of this Example using the appropriate starting materials and modifications.

| Structure | Name | LCMS |
|---|---|---|
| BocN–[piperidine]–C(O)–N(Me)OMe | tert-butyl 4-(methoxy(methyl)carbamoyl)piperidine-1-carboxylate | 273 |

Step 2: ethyl 6-methyl-7-(1-(1-methyl-2-oxo-1,2-dihydropyridin-3-yl)vinyl)pyrrolo[1,2-b]pyridazine-5-carboxylate (10)

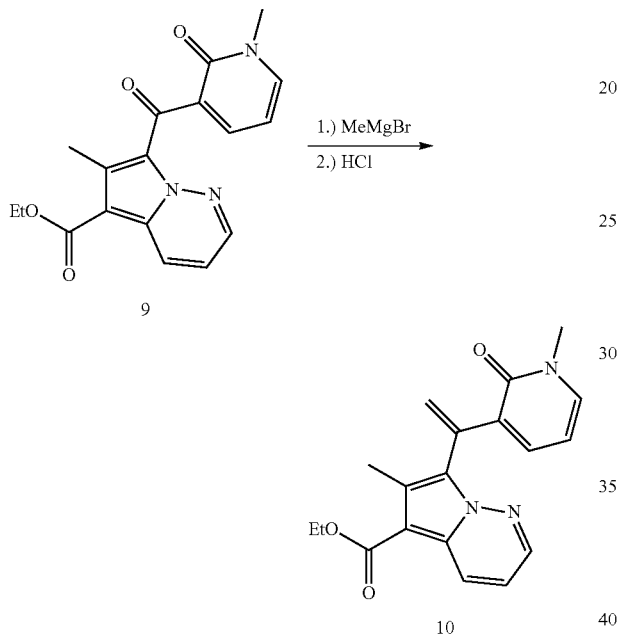

To a solution of ethyl 6-methyl-7-(1-methyl-2-oxo-1,2-dihydropyridine-3-carbonyl)pyrrolo[1,2-b]pyridazine-5-carboxylate (250 mg, 0.74 mmol) in anhydrous tetrahydrofuran (10 mL) was added methylmagnesium bromide (1.48 mL, 1.48 mmol) at 0° C. The reaction mixture was stirred at 0° C. to room temperature overnight before being quenched with 1 M HCl and partitioned with water and ethyl acetate. The organic layer was dried and concentrated to afford the crude title compound as a yellow oil, which was used directly in the next step. (200 mg, 80% yield)

Step 3: ethyl 6-methyl-7-(1-(1-methyl-2-oxo-1,2-dihydropyridin-3-yl)ethyl)pyrrolo[1,2-b]pyridazine-5-carboxylate (11)

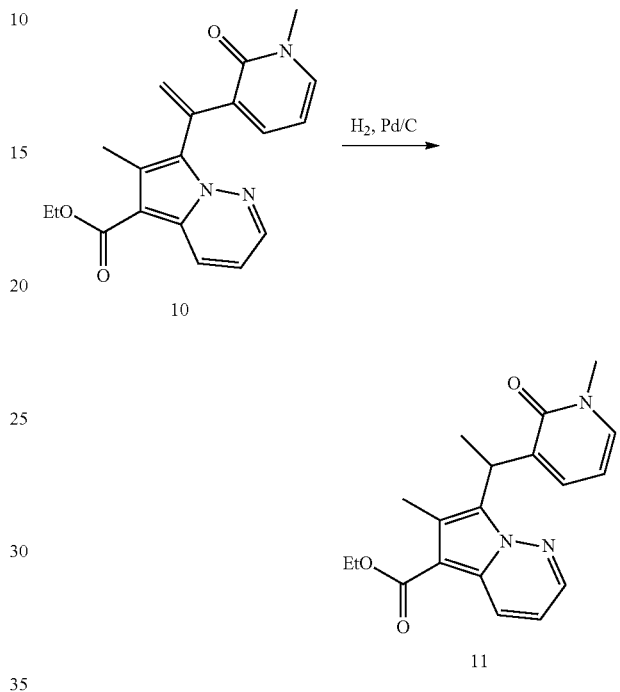

A mixture of ethyl 6-methyl-7-(1-(1-methyl-2-oxo-1,2-dihydropyridin-3-yl)vinyl)pyrrolo[1,2-b]pyridazine-5-carboxylate (200 mg, 0.74 mmol) and Pd/C (50 mg, 10%) in methanol (10 mL) was placed under an atmosphere of hydrogen and the reaction was stirred at room temperature overnight. The reaction was then purged, placed under nitrogen and was filtered and concentrated to afford the title compound which was used without further purification. (140 mg, 70%)

The intermediates shown in the following table were prepared according to the procedure described in this example using the appropriate starting materials and modifications.

| Method | Structure | Name | LCMS |
|---|---|---|---|
| 11A | 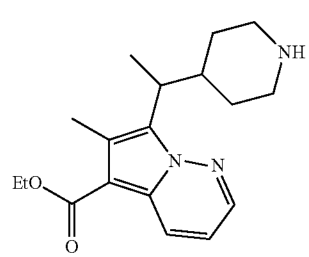 [SMILES: CCOC(=O)c1c(C)c(C(C)C2CCNCC2)n2ncccc12] | ethyl 6-methyl-7-(1-(piperidin-4-yl)ethyl)pyrrolo[1,2-b]pyridazine-5-carboxylate | 316 |

-continued

| Method | Structure | Name | LCMS |
|---|---|---|---|
| 11B | 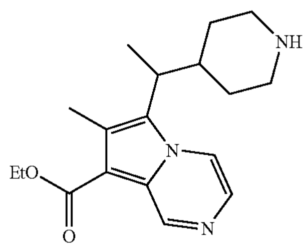 [SMILES: CCOC(=O)c1c(C)c(C(C)C2CCNCC2)n2ccncc12] | ethyl 7-methyl-6-(1-(piperidin-4-yl)ethyl)pyrrolo[1,2-a]pyrazine-8-carboxylate | 316 |

Example 11

Synthesis of ethyl 6-methyl-7-(1-(1-methylpiperidin-4-yl)ethyl)pyrrolo[1,2-b]pyridazine-5-carboxylate (Intermediate 12)

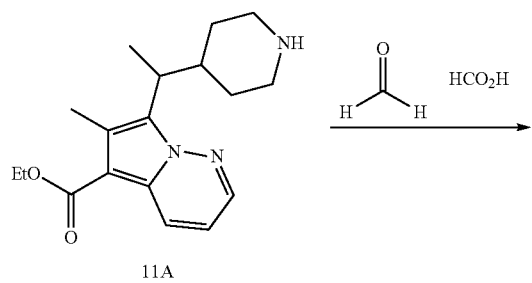

Example 12

Synthesis of (±)-6-methyl-7-(1-phenylethyl)pyrrolo[1,2-b]pyridazine-5-carboxylic acid (Intermediate 13)

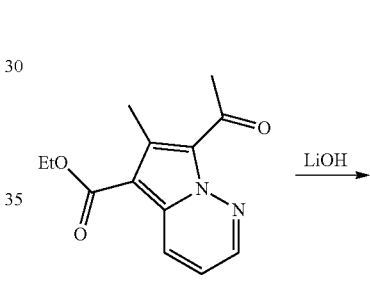

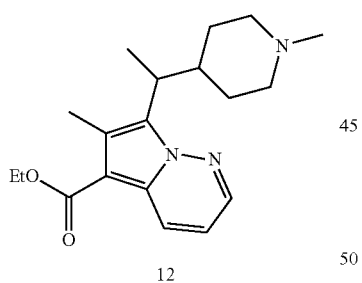

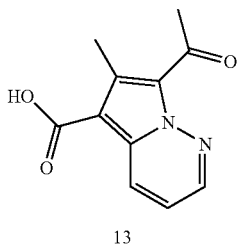

A mixture of compound ethyl 6-methyl-7-(1-(piperidin-4-yl)ethyl)pyrrolo[1,2-b]pyridazine-5-carboxylate (360 mg, 1.14 mmol) in tetrahydrofuran (10 mL), were added formaldehyde (37%) aqueous solution (278 mg, 3.42 mmol) and sodium triacetoxyhydroborate (567 mg, 3.42 mmol). The reaction mixture was stirred at 50° C. for 1 hour. The reaction mixture was quenched by the addition of saturated aqueous potassium carbonate. The aqueous layer was extracted with ethyl acetate (30 mL×3). The combined organic layers were dried over sodium sulfate and concentrated to afford the title compound (376 mg, 100%) as a yellow oil. LCMS (M+H$^+$) m/z: calc'd 329.21; found 329.9.

Lithium hydroxide monohydrate (41 mg, 0.97 mmol) was added to ethyl 7-acetyl-6-methylpyrrolo[1,2-b]pyridazine-5-carboxylate (40 mg, 0.16 mmol) in THF/H$_2$O (10 mL, 1:1) and the resulting mixture was heated to reflux with stirring overnight. The mixture was then allowed to cool to rt and was conc. in vacuo, diluted with water (5 mL), and acidified with 1N HCl to a pH ~2. A precipitate formed which was collected via vacuum filtration to afford the title compound as a white solid (30 mg, yield 85%).

The intermediates shown in the following table were prepared according to the procedure described above using the appropriate starting materials and modifications.

| Intermediate No. | Structure | Name | LCMS |
|---|---|---|---|
| 13 | 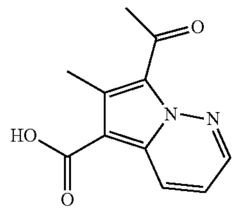 [SMILES: CC(=O)c1c(C)c(C(=O)O)c2cccnn12] | 7-acetyl-6-methylpyrrolo[1,2-b]pyridazine-5-carboxylic acid | 218 |
| 13A | 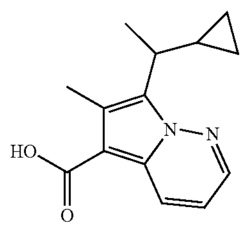 [SMILES: Cc1c(C(=O)O)c2cccnn2c1C(C)C1CC1] | 7-(1-cyclopropylethyl)-6-methylpyrrolo[1,2-b]pyridazine-5-carboxylic acid | 244 |
| 13C | 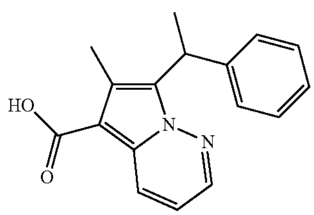 [SMILES: Cc1c(C(=O)O)c2cccnn2c1C(C)c1ccccc1] | 6-methyl-7-(1-phenylethyl)pyrrolo[1,2-b]pyridazine-5-carboxylic acid | 280 |
| 13D | 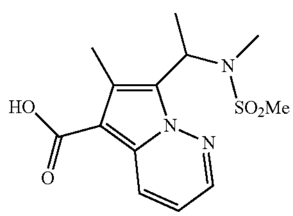 [SMILES: Cc1c(C(=O)O)c2cccnn2c1C(C)N(C)S(C)(=O)=O] | 6-methyl-7-(1-(N-methylmethylsulfonamido)ethyl)pyrrolo[1,2-b]pyridazine-5-carboxylic acid | 311 |
| 13E | 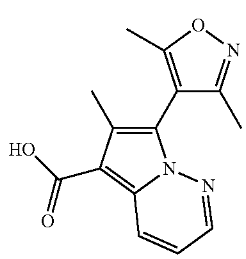 [SMILES: Cc1noc(C)c1-c1c(C)c(C(=O)O)c2cccnn12] | 7-(3,5-dimethylisoxazol-4-yl)-6-methylpyrrolo[1,2-b]pyridazine-5-carboxylic acid | 271 |
| 13F | 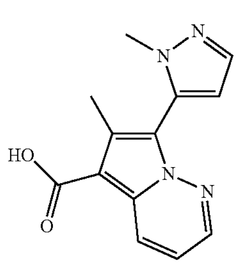 [SMILES: Cc1c(C(=O)O)c2cccnn2c1-c1ccnn1C] | 6-methyl-7-(1-methyl-1H-pyrazol-5-yl)pyrrolo[1,2-b]pyridazine-5-carboxylic acid | 256 |

-continued

| Intermediate No. | Structure | Name | LCMS |
|---|---|---|---|
| 13G | 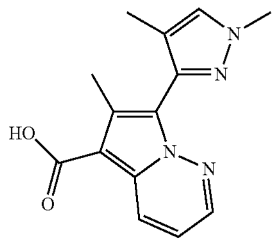 [SMILES: Cc1cn(C)nc1-c1c(C)c(C(=O)O)c2cccnn12] | 7-(1,4-dimethyl-1H-pyrazol-3-yl)-6-methylpyrrolo[1,2-b]pyridazine-5-carboxylic acid | 270 |
| 13H | 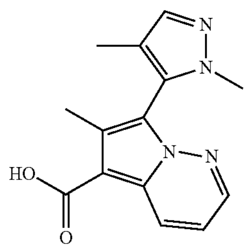 [SMILES: Cc1cnn(C)c1-c1c(C)c(C(=O)O)c2cccnn12] | 7-(1,4-dimethyl-1H-pyrazol-5-yl)-6-methylpyrrolo[1,2-b]pyridazine-5-carboxylic acid | 270 |
| 13I | 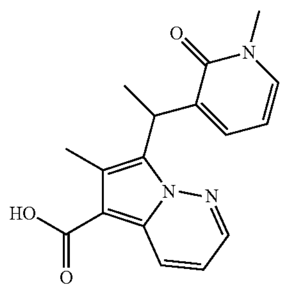 [SMILES: Cc1c(C(=O)O)c2cccnn2c1C(C)c1cccn(C)c1=O] | 6-methyl-7-(1-(1-methyl-2-oxo-1,2-dihydropyridin-3-yl)ethyl)pyrrolo[1,2-b]pyridazine-5-carboxylic acid | 311 |
| 13J | 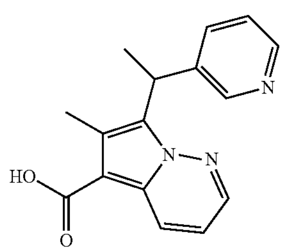 [SMILES: Cc1c(C(=O)O)c2cccnn2c1C(C)c1cccnc1] | 6-methyl-7-(1-(pyridin-3-yl)ethyl)pyrrolo[1,2-b]pyridazine-5-carboxylic acid | 282 |
| 13K | 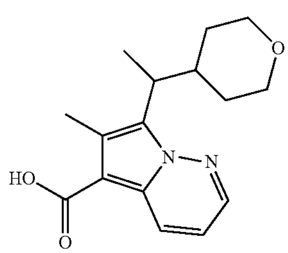 [SMILES: Cc1c(C(=O)O)c2cccnn2c1C(C)C1CCOCC1] | 6-methyl-7-(1-(tetrahydro-2H-pyran-4-yl)ethyl)pyrrolo[1,2-b]pyridazine-5-carboxylic acid | 289 |
| 13L | 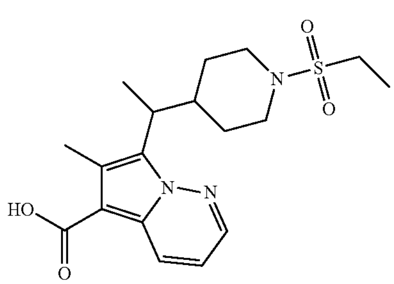 [SMILES: CCS(=O)(=O)N1CCC(C(C)c2c(C)c(C(=O)O)c3cccnn23)CC1] | 7-(1-(1-(ethylsulfonyl)piperidin-4-yl)ethyl)-6-methylpyrrolo[1,2-b]pyridazine-5-carboxylic acid | 380 |

-continued

| Intermediate No. | Structure | Name | LCMS |
|---|---|---|---|
| 13M | 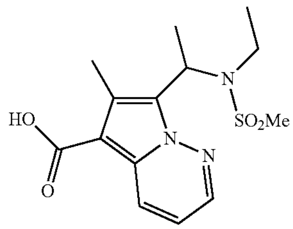 [SMILES: CCN(C(C)c1c(C)c(C(=O)O)c2cccnn12)S(C)(=O)=O] | 7-(1-(N-ethylmethylsulfonamido)ethyl)-6-methylpyrrolo[1,2-b]pyridazine-5-carboxylic acid | 326 |
| 13N | 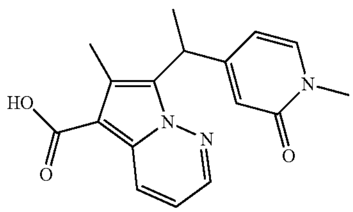 [SMILES: Cc1c(C(=O)O)c2cccnn2c1C(C)c1ccn(C)c(=O)c1] | 6-methyl-7-(1-(1-methyl-2-oxo-1,2-dihydropyridin-4-yl)ethyl)pyrrolo[1,2-b]pyridazine-5-carboxylic acid | 312 |
| 13O | 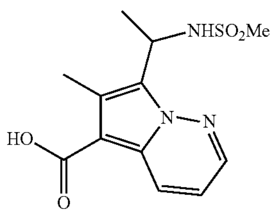 | 6-methyl-7-(1-(methylsulfonamido)ethyl)pyrrolo[1,2-b]pyridazine-5-carboxylic acid | 298 |
| 13P | 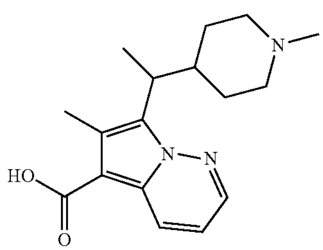 [SMILES: Cc1c(C(=O)O)c2cccnn2c1C(C)C1CCN(C)CC1] | 6-methyl-7-(1-(1-methylpiperidin-4-yl)ethyl)pyrrolo[1,2-b]pyridazine-5-carboxylic acid | 302 |
| 13Q | 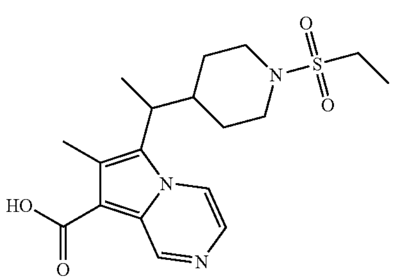 [SMILES: CCS(=O)(=O)N1CCC(C(C)c2c(C)c(C(=O)O)c3cnccn23)CC1] | 6-(1-(1-(ethylsulfonyl)piperidin-4-yl)ethyl)-7-methylpyrrolo[1,2-a]pyrazine-8-carboxylic acid | 380 |
| 13R | 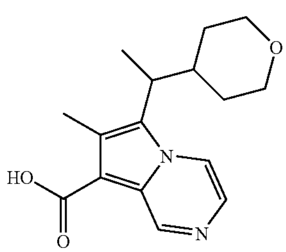 [SMILES: Cc1c(C(=O)O)c2cnccn2c1C(C)C1CCOCC1] | 7-methyl-6-(1-(tetrahydro-2H-pyran-4-yl)ethyl)pyrrolo[1,2-a]pyrazine-8-carboxylic acid | 289 |

| Intermediate No. | Structure | Name | LCMS |
|---|---|---|---|
| 13S | 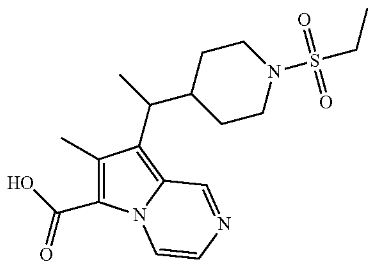 [SMILES: CCS(=O)(=O)N1CCC(C(C)c2c(C)c(C(=O)O)n3ccncc23)CC1] | 8-(1-(1-(ethylsulfonyl)piperidin-4-yl)ethyl)-7-methylpyrrolo[1,2-a]pyrazine-6-carboxylic acid | 380 |

Example 13

Synthesis of 6-methyl-7-(1-(N-methylacetamido)ethyl)pyrrolo[1,2-b]pyridazine-5-carboxylic acid (Intermediate 14)

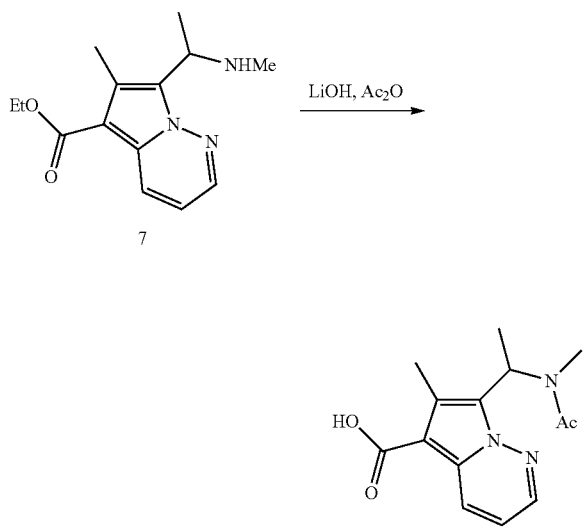

To the solution of ethyl 6-methyl-7-(1-(methylamino)ethyl)pyrrolo[1,2-b]pyridazine-5-carboxylate (70 mg, 0.26 mmol) in THF/MeOH/H$_2$O (1:1:1, 2 mL) was added lithium hydroxide monohydrate (80 mg, 1.9 mmol). The mixture was then stirred with heating at reflux for 2 h. Then the reaction was then allowed to cool to rt and Ac$_2$O was added (270 mg, 2.68 mmol). The reaction was then stirred overnight at room temperature and was conc. in vacuo. The resulting residue was diluted with water (5 mL), acidified with 1 N HCl to pH ~2, and extracted with DCM (20 mL). The organic extract was dried over Na$_2$SO$_4$, filtered and concentrated to afford the title compound as a white solid which was used without further purification (40 mg, yield 54%) m/z 311.

Example 14

Synthesis of 3-(aminomethyl)-4-methoxy-6-methylpyridin-2-ol (Intermediate 15)

Step 1: 2-amino-6-methyl-4-oxo-4H-pyran-3-carbonitrile

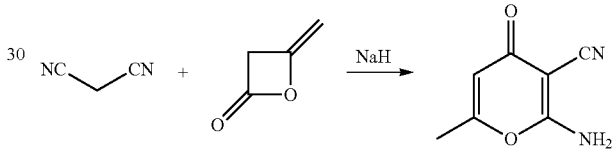

Malononitrile (110 g, 1.67 mol) was dissolved in dry THF (1000 mL) and cooled in ice-water bath. NaH (60% in mineral oil, 67 g, 1.67 mol) was added portionwise below 10° C. very carefully while the reaction flash was evacuated with N$_2$ flow. After addition completed, the mixture was stirred at 0° C. for 30 min. Then 4-methyleneoxetan-2-one (140 g, 1.67 mol) was added dropwise below 0° C. After addition completed, the mixture was stirred at −10° C. for 1 h. The reaction mixture was neutralized by 4 N HCl and concentrated under vacuum to afford the title compound an orange oil. The crude product was used to next step without further purification.

Step 2: 2,4-dihydroxy-6-methylnicotinonitrile

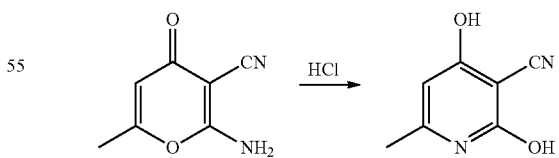

2-amino-6-methyl-4-oxo-4H-pyran-3-carbonitrile from above was dissolved in 4 N HCl/H$_2$O (2500 mL) and refluxed for 5 h with stirring strongly. After cooled to r.t., the precipitate was filtered, washed with H$_2$O (500 mL), ethanol (500 mL) and MTBE (200 mL) and dried under high vacuum to afford the title compound as a yellow powder. (165 g, yield 66%)

Step 3: 2,4-dichloro-6-methylnicotinonitrile

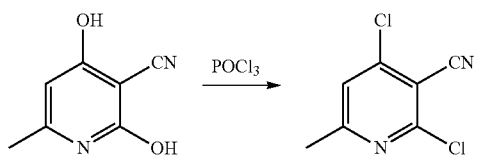

2,4-dihydroxy-6-methylnicotinonitrile (40 g, 266.4 mmol) was dissolved in POCl₃ (120 mL) and added by DMF (4 drops). The mixture was heated for 3 h. Then the mixture was concentrated under vacuum. The residue was dissolved in EtOAc (2 L) and neutralized by saturated NaHCO₃. Then the mixture was filtered through a Celite pad to remove the dark flocculating. The organic layer was separated, dried over Na₂SO₄ and concentrated under vacuum to give the title compound as an off-white solid. (45 g, yield 90%).

Step 4: 2,4-dimethoxy-6-methylnicotinonitrile

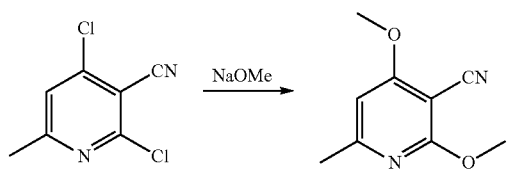

2,4-dichloro-6-methylnicotinonitrile (45 g, 240 mmol) was dissolved in CH₃OH (300 mL). NaOMe (30% in MeOH, 100 mL, 1680 mmol) was added. The mixture was refluxed for 4 h. After cooled to r.t., the reaction mixture was neutralized by HOAc. The solvent was removed under vacuum and the residue was washed with H₂O (300 mL) and MTBE (100 mL). The resulting solid was coevaporated with dry THF (300 mL) to give the title compound as a dark-yellow solid. (40 g, yield 95%)

Step 5: tert-butyl ((2,4-dimethoxy-6-methylpyridin-3-yl)methyl)carbamate

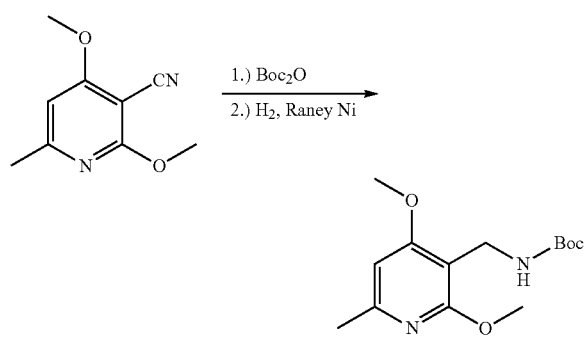

2,4-dimethoxy-6-methylnicotinonitrile (10.0 g, 56 mmol) was dissolved in the mixture of THF (260 mL) and methanol (260 mL). Raney Ni (wet, 10.0 g), TEA (29.0 g, 280 mmol) and Boc₂O (36.8 g, 168 mmol) were added. Then the mixture was hydrogenated (1 atom) at r.t. overnight. After reaction completed, the reaction mixture was filtered through a Celite pad. 6 parallel reactions were combined and concentrated under vacuum to give the title compound as a yellow solid. (84 g, 88%)

Step 6: 3-(aminomethyl)-4-methoxy-6-methylpyridin-2-ol (15)

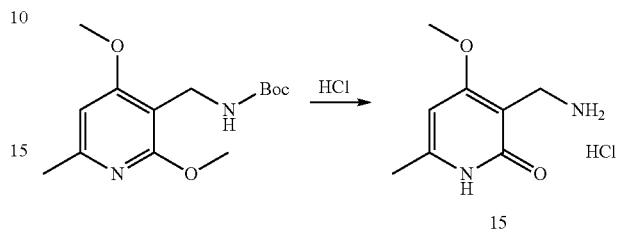

Tert-butyl ((2,4-dimethoxy-6-methylpyridin-3-yl)methyl)carbamate (83 g, 294 mmol) was dissolved in 4 N HCl/H₂O (830 mL). Then the mixture was refluxed for 4.5 h. (The reaction mixture was monitored by MS spectrum to make sure the methyl group at 2-position de-protect completely.) After the reaction completed, the mixture was concentrated under vacuum to give a brown oil. The oil was suspended in EtOH (300 mL) for 15 min to give a yellow precipitate. The precipitate was filtered, washed with ethanol (100 mL) and MTBE (100 mL) and dried under high vacuum to give 38 g of fraction 1 3-(aminomethyl)-4-methoxy-6-methylpyridin-2-ol (Purity 98% by LCMS, yield 63%) as a yellow powder. In the meantime, the filtration from fraction 1 was concentrated under vacuum and the residue was solidified by ethanol (100 mL). The precipitate was filtered, washed with ethanol (100 mL) and MTBE (100 mL) and dried under high vacuum to give 20 g of the title compound as a yellow powder.

Example 15

Synthesis of 3-(aminomethyl)-4,6-dimethylpyridin-2(1H)-one (Intermediate 16)

Step 1: 4,6-dimethyl-2-oxo-1,2-dihydropyridine-3-carbonitrile

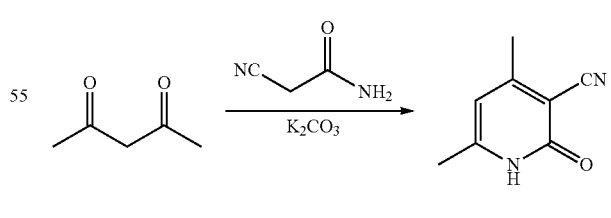

To a solution of pentane-2,4-dione (100 g, 1.0 mol) in H₂O (2 L) were added 2-cyanoacetamide (84 g, 1.0 mol) and K₂CO₃ (13.8 g, 0.1 mol). Then the mixture was stirred at room temperature for 16 hr. The reaction solution was filtrated to give crude product. The crude was washed with water and concentrated to give the title compound (138 g, 93%).

Step 2: tert-butyl ((4,6-dimethyl-2-oxo-1,2-dihydropyridin-3-yl)methyl)carbamate

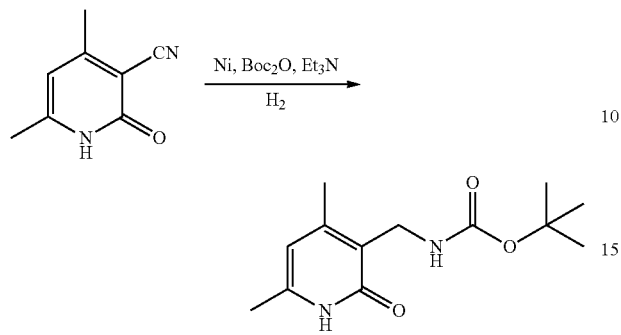

To a solution of 4,6-dimethyl-2-oxo-1,2-dihydropyridine-3-carbonitrile (40 g, 0.27 mol) in THF/CH$_3$OH (1:1, 2 L) were added Ni (40 g), Boc$_2$O (110 g, 0.5 mol) and Et$_3$N (50 g, 0.5 mol). Then the mixture was stirred in H$_2$ atmosphere at room temperature for 48 hr. The reaction solution was filtrated and concentrated to give crude product. The crude was added H$_2$O (200 mL) and extracted by DCM (600 mL×3). The organic layer was concentrated to give the title compound (40 g, 56%) for next step.

Step 3: 3-(aminomethyl)-4,6-dimethylpyridin-2(1H)-one (16)

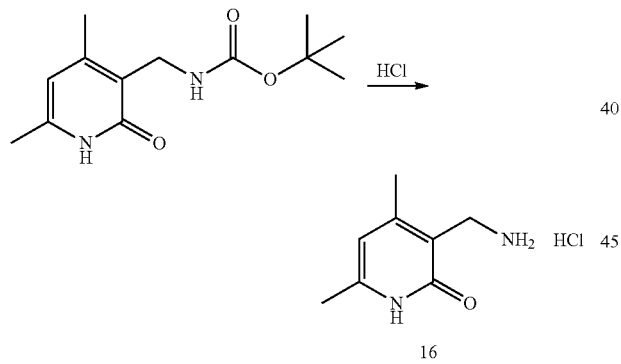

Tert-butyl ((4,6-dimethyl-2-oxo-1,2-dihydropyridin-3-yl)methyl)carbamate (40 g, 0.27 mol) was added into dioxane/HCl (1 L) and the mixture was stirred at room temperature for 4 hr. The reaction solution was filtrated and concentrated to give crude product. The crude was washed with ethyl acetate (100 mL×2) and EtOH (50 mL×1) and concentrated to afford the title compound as its HCl salt (15 g, 40%). LCMS (M+H+) m/z: calc'd. 152.19; found 153.1. $^1$H NMR (DMSO, 400 MHz) δ 11.84 (s, 1H), 8.07 (s, 3H), 5.96 (s, 1H), 3.76-7.75 (d, J=5.6 Hz, 2H), 2.21 (s, 3H), 2.15 (s, 3H).

The intermediate shown in the following table were prepared according to the procedure described in Steps 1-3 of this Example using the appropriate starting materials and modifications.

| Intermediate | Structure | Name | LCMS |
|---|---|---|---|
| 16A | 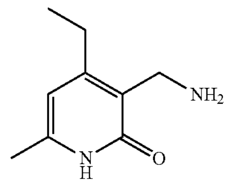 | 3-(aminomethyl)-4-ethyl-6-methylpyridin-2(1H)-one | 167 |
| 16B | 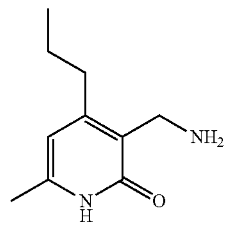 | 3-(aminomethyl)-4-propyl-6-methylpyridin-2(1H)-one | 181 |

Example 16

Synthesis of 7-acetyl-N-((4-methoxy-6-methyl-2-oxo-1,2-dihydropyridin-3-yl)methyl)-6-methylpyrrolo[1,2-b]pyridazine-5-carboxamide (Compound 100)

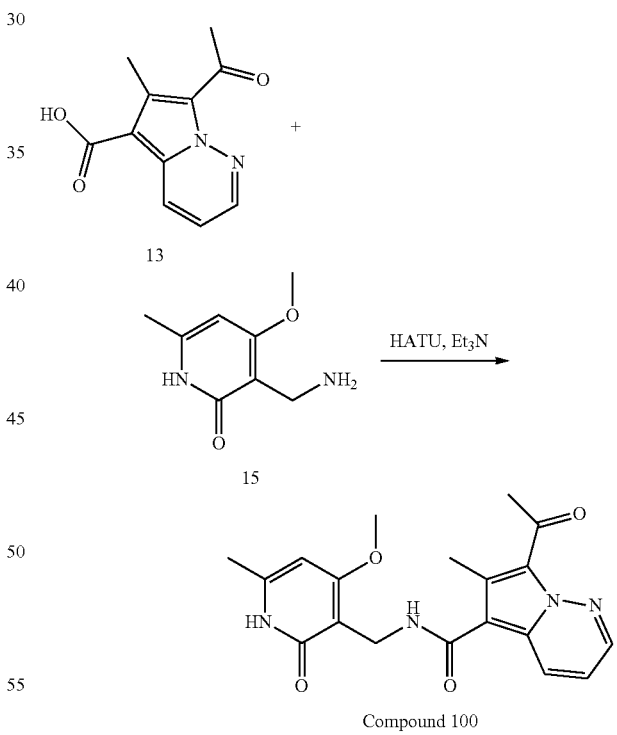

To a solution of 7-acetyl-6-methylpyrrolo[1,2-b]pyridazine-5-carboxylic acid (13; 40 mg, 0.18 mmol) in dichloromethane (10 mL) was added with 1H-benzo[d][1,2,3]triazol-1-ol (15; 140 mg, 0.37 mmol) and triethylamine (56 mg, 0.55 mmol). The reaction was allowed to stir for 30 minutes and 3-(aminomethyl)-4-methoxy-6-methylpyridin-2(1H)-one (40 mg, 0.24 mmol) was added and the reaction mixture was stirred at room temperature for 3 h. The solution was then conc. in vacuo, diluted with water (20 mL), and extracted with ethyl acetate (20 mL). The combined organic phase was dried over anhydrous sodium sulfate, filtered and concentrated to afford a residue. The residue was purified by preparative-HPLC (Column: YMC C18 150*30 mm*5um; Mobile phase A: water with 0.1% HCl; Mobile phase B: MeCN; column temperature: 30° C.; Gradient: B/A 35-65%) to afford the title compound as yellow solid (10 mg, yield 14%). LCMS (M+H$^+$) m/z: calc'd 368.15; found 369.2. $^1$H NMR (400 MHz, CD$_3$OD) δ 8.46-8.44 (m, 1H), 8.30-8.27 (d, 1H), 7.17-7.13 (dd, 1H), 6.94 (s, 1H), 4.11 (s, 3H), 2.79 (s, 3H), 2.64 (s, 3H), 2.54 (s, 3H).

The compounds of the invention shown in the following table were prepared according to the procedure described above using the indicated starting materials and art-known modifications.

| Compound | Name | $^1$H NMR | LCMS | Starting Materials |
|---|---|---|---|---|
| 101 | (±)-N-((4-methoxy-6-methyl-2-oxo-1,2-dihydropyridin-3-yl)methyl)-6-methyl-7-(1-phenylethyl)pyrrolo[1,2-b]pyridazine-5-carboxamide | (400 MHz, CDCl$_3$) δ 8.44-8.46 (m, 1H) 8.00-8.01 (dd, 1H) 7.17-7.24 (t, 5H) 7.14-7.17 (s, 1H) 6.56-6.59 (t, 1H) 5.94 (s, 1H) 5.04-5.10 (t, 1H) 4.60-4.62 (m, 2H,) 3.89 (s, 3 H) 2.35 (s, 3 H), 2.99 (s,3H) 1.76-1.78 (m, 3H) | 431 | 13C, 15 |
| 102 | (±)-7-(1-cyclopropylethyl)-N-((4-methoxy-6-methyl-2-oxo-1,2-dihydropyridin-3-yl)methyl)-6-methylpyrrolo[1,2-b]pyridazine-5-carboxamide | (400 MHz, CDCl$_3$) 8.44 (s, 1H) 8.00 (s, 1H) 6.58 (s, 1H) 6.00 (s, 1H) 4.65 (s, 2H) 3.92 (s, 3H) 2.67-2.65 (m, 1H) 2.49 (s, 3H) 2.34 (s, 3H) 1.46-1.45 (d, 3H) 1.24 (s, 2H) 0.86-0.81 (m, 1H) 0.57-0.55 (m, 1H), 0.26-0.200 (m, 2H) | 395 | 13A, 15 |
| 103 | (±)-N-((4-methoxy-6-methyl-2-oxo-1,2-dihydropyridin-3-yl)methyl)-6-methyl-7-(1-(N-methylmethylsulfonamido)ethyl)pyrrolo[1,2-b]pyridazine-5-carboxamide | (400 MHz, CDCl$_3$-d4) δ 8.53-8.50 (d, 1H), 8.10-8.08 (dd, 1H), 6.72-6.68 (dd, 1H), 5.96 (a, 1H), 5.79-5.77 (dd, 1H), 4.64-4.62 (d, 2H), 3.9(s, 3H), 2.9(s, 3H), 2.62-2.60(d, 3H), 2.31(s, 3H), 1.84-1.82(dd, 3H) | 462 | 13D, 15 |
| 104 | (±)-N-((4-methoxy-6-methyl-2-oxo-1,2-dihydropyridin-3-yl)methyl)-6-methyl-7-(1-(N-methylacetamido)ethyl)pyrrolo[1,2-b]pyridazine-5-carboxamide | (400 MHz, DMSO-d6) δ 8.26-8.23 (m, 2H) 8.10-8.08 (dd, 1H) 7.6 (s, 1H) 6.83-6.79 (m, 1H) 6.09 (m 2H) 4.35-4.34 (d, 2H) 3.85(s, 3H) 2.78-2.76 (s, 3H) 2.5 (s, 3H) 2.21 (s, 3H) 2.05 (s, 3H) 1.70-1.68 (d, 3H) | 426 | 14, 15 |
| 109 | N-((4-methoxy-6-methyl-2-oxo-1,2-dihydropyridin-3-yl)methyl)-6-methyl-7-(1-methyl-1H-pyrazol-5-yl)pyrrolo[1,2-b]pyridazine-5-carboxamide | (400 MHz, CDCl$_3$) 2.31 (s, 3H) 2.45 (s, 3H) 3.66 (s, 3H) 3.91(s, 3H) 4.65-4.66 (d, J = 2.4 Hz, 2H) 5.95 (s, 1H) 6.37-6.38 (d, J = 2 Hz, 1H) 6.75-6.79 (m, 1H) 7.55-7.58 (m, 1H) 7.63-7.64 (m, J = 2 Hz, 1H) 8.09-8.11 (m, 1H) 8.66-8.69 (m, 1H) | 407 | 13F, 15 |
| 110 | N-((4-methoxy-6-methyl-2-oxo-1,2-dihydropyridin-3-yl)methyl)-6-methyl-7-(1-(1-methyl-2-oxo-1,2-dihydropyridin-4-yl)ethyl)pyrrolo[1,2-b]pyridazine-5-carboxamide | (400 MHz, METHANOL-d$_4$) 1.73 (d, J = 7.53 Hz, 3 H) 2.33 (s, 3 H) 2.41 (s, 3 H) 3.49 (s, 3 H) 3.95 (s, 3 H) 4.51 (br. s., 2 H) 5.34 (t, J = 5.02 Hz, 1 H) 6.14-6.20 (m, 1 H) 6.30 (br. s., 1 H) 6.47 (s, 1 H) 6.75 (d, J = 5.52 Hz, 1 H) 7.45 (d, J = 7.03 Hz, 1 H) 8.09 (d, J = 4.52 Hz, 1 H) 8.19 (d, J = 10.54 Hz, 1 H) | 462 | 13M, 15 |
| 111 | (±)-N-((4-methoxy-6-methyl-2-oxo-1,2-dihydropyridin-3-yl)methyl)-6-methyl-7-(1-(1-methyl-2-oxo-1,2-dihydropyridin-3-yl)ethyl)pyrrolo[1,2-b]pyridazine-5-carboxamide | (400 MHz, CD$_3$OD): 8.15-8.17 (m, 2H), 7.7-7.71(m, 1H), 7.48-7.50 (m, 1H), 6.78-6.83 (m, 2H), 4.95-5.02 (m, 1H), 4.55 (s, 2H), 4.09 (s, 3H), 3.47 (s, 3H), 2.5 (s, 3H), 2.45 (s, 3H), 1.69-1.70 (d, J = 7.2 Hz, 3H) | 462 | 13I, 15 |
| 112 | (±)-N-((4-methoxy-6-methyl-2-oxo-1,2-dihydropyridin-3-yl)methyl)-6-methyl-7-(1-(methylsulfonamido)ethyl)pyrrolo[1,2-b]pyridazine-5-carboxamide | (CDCl$_3$, 400 MHz) δ 8.54-8.52 (d, 1H), 8.03-8.02 (d, 1H), 6.69-6.65(q, 1H), 5.88 (s 1H), 5.05-5.03 (q, 1H), 4.54 (s, 2H), 3.83(s, 3H), 2.47(s, 3H), 2.25(s, 6H), 1.61-1.59 (d, 3H) | 448 | 13O, 15 |
| 113 | (±)-N-((4-methoxy-6-methyl-2-oxo-1,2-dihydropyridin-3-yl)methyl)-6-methyl-7-(1-(pyridin-3-yl)ethyl)pyrrolo[1,2-b]pyridazine-5-carboxamide | (400 MHz, CDCl$_3$) 3.88 (s, 3H)12.83 (s, 1H), 4.61-4.63 (d, J = 5.6 Hz, 2H), 4.99-5.02 (d, J = 7.6 Hz, 1H), 5.92 (s, 1H), 6.57-6.61 (m, 1H), 7.12-7.16 (m, 1H), 7.26-7.40 (m, 1H), 7.52-7.56 (m, 1H), 7.97-8.00 (m, 1H), 8.38-8.52 (m, 2H), 8.52 (s, 1H), 12.83 (s, 1H) | 432 | 13J, 15 |

| Compound | Name | ¹H NMR | LCMS | Starting Materials |
|---|---|---|---|---|
| 114 | 7-(3,5-dimethylisoxazol-4-yl)-N-((4-methoxy-6-methyl-2-oxo-1,2-dihydropyridin-3-yl)methyl)-6-methylpyrrolo [1,2-b]pyridazine-5-carboxamide | (400 MHz, CDCl₃) δ: 2.09 (s, 3H), 2.24-2.40 (m, 9H), 3.91 (s, 3H), 4.65-4.67 (d, J = 5.6 Hz, 2H), 5.96 (s, 1H), 6.72-6.76 (m, 1H), 7.49-7.53 (m, 1H), 8.05-8.08 (m, 1H), 8.63-8.67 (m, 1H), 12.32 (s, 1H) | 421 | 13E, 15 |
| 115 | (±)-N-((4-methoxy-6-methyl-2-oxo-1,2-dihydropyridin-3-yl)methyl)-7-methyl-6-(1-(tetrahydro-2H-pyran-4-yl)ethyl)pyrrolo[1,2-a]pyrazine-8-carboxamide | (400 MHz, Methanol-d4) 1.01-0.99 (m, 1H), 1.23-1.13 (m, 2H), 1.44 (d, J = 7.2 Hz, 3H), 2.03-2.00 (m, 1H), 2.18-2.15 (m, 1H), 2.34 (s, 3H), 2.46 (s, 3H), 3.18-3.14 (m, 1H), 3.28-3.25 (m, 1H), 3.50-3.44 (m, 1H), 3.80-3.76 (m, 1H), 3.97 (s, 3H), 4.05-4.01 (m, 1H), 4.54 (s, 2H), 6.30 (s, 1H), 7.51-7.50 (m, 2H), 8.22-8.20 (m, 1H), 8.98 (s, 1H) | 439 | 13R, 15 |
| 116 | (±)-N-((4-methoxy-6-methyl-2-oxo-1,2-dihydropyridin-3-yl)methyl)-6-methyl-7-(1-(tetrahydro-2H-pyran-4-yl)ethyl)pyrrolo[1,2-b]pyridazine-5-carboxamide | (400 MHz, CDCl₃) 12.40 (1 H), 8.45 (dd, J = 9.0, 2.0 Hz, 1 H), 8.02 (dd, J = 4.2, 1.7 Hz, 1 H), 7.35-7.43 (m, 1 H) 6.58 (dd, J = 9.2 Hz, 4.2 Hz, 1H), 5.96 (s, 1 H), 4.64 (d, J = 5.5 Hz, 2 H), 4.03 (dd, J = 11.5, 3.0 Hz, 1 H), 3.91 (s, 3 H), 3.77 (dd, J = 11.8, 2.7 Hz, 1 H), 3.41 (td, J = 11.8, 2.0 Hz, 1 H), 3.21 (td, J = 11.8, 2.0 Hz, 2 H), 2.49 (s, 3 H), 2.26-2.39 (m, 4 H), 1.95 (d, J = 12.0 Hz, 1 H), 1.26-1.44 (m, 4 H), 1.13 (qd, J = 12.3, 4.5 Hz, 1 H), 0.92 (d, J = 14.5 Hz, 1H) | 439 | 13K, 15 |
| 117 | (±)-8-(1-(1-(ethylsulfonyl)piperidin-4-yl)ethyl)-N-((4-methoxy-6-methyl-2-oxo-1,2-dihydropyridin-3-yl)methyl)-7-methylpyrrolo[1,2-a]pyrazine-6-carboxamide | (400 MHz, CDCl₃): d 1.16-1.13 (m, 1H), 1.25-1.21 (m, 1H), 1.38-1.34 (m, 4H), 1.42-1.40 (m, 1H), 1.46 (d, J = 2.8, 1H), 2.15-2.11 (m, 1H), 2.33 (s, 3H), 2.46 (s, 3H), 2.59-2.53 (m, 1H), 2.86-2.73 (m, 2H), 2.94-2.88 (m, 2H), 3.66-3.63 (m, 3.89 (s, 1H), 3.92 (s, 3H), 4.64-4.63 (m, 2H), 6.00 (s, 2H), 7.56-7.54 (m, 1H), 7.64-7.63 (m, 1H), 8.88 (m, 1H), 9.16 (d, J = 4.8, 1H) | 530 | 13S, 15 |
| 118 | N-((4,6-dimethyl-2-oxo-1,2-dihydropyridin-3-yl)methyl)-7-(3,5-dimethylisoxazol-4-yl)-6-methylpyrrolo[1,2-b]pyridazine-5-carboxamide | (400 MHz, CDCl₃) δ: 2.09 (s, 3H), 2.25-2.27 (m, 6H), 2.39 (s, 3H), 2.45 (s, 3H),4.60-4.62 (m, 2H), 5.97 (s, 1H), 6.74-6.76 (m, 1H), 7.39-7.42 (brs, 1H), 8.08 (dd, J = 4 Hz, J = 1.6 Hz, 1H), 8.62 (dd, J = 12 Hz, J = 1.6 Hz, 1H) | 405 | 13E,16 |
| 119 | (±)-6-(1-(1-(ethylsulfonyl)piperidin-4-yl)ethyl)-N-((4-methoxy-6-methyl-2-oxo-1,2-dihydropyridin-3-yl)methyl)-7-methylpyrrolo[1,2-a]pyrazine-8-carboxamide | (400 MHz, MeOD) 1.09-1.29 (m, 6H), 1.14-1.48(m, 4H), 2.15-2.19(m, 2H), 2.39(s, 2H), 2.54(s, 3H), 2.68(m, 1H), 2.86(m, 1H), 2.98 (q, J = 3.2 Hz, 2H), 3.57 (d, J = 12 Hz, 1H), 3.83 (d, J = 12 Hz, 1H), 4.00 (s, 3H), 4.54 (s, 2H) C6.51(s, 3H), 7.64 (d, J = 5.6 Hz, 1H), 8.66 (d, J = 6.0 Hz, 1H), 9.19 (s, 1H). | 530 | 13Q, 15 |
| 120 | 7-(1,4-dimethyl-1H-pyrazol-5-yl)-N-((4-methoxy-6-methyl-2-oxo-1,2-dihydropyridin-3-yl)methyl)-6-methylpyrrolo[1,2-b]pyridazine-5-carboxamide | (400 MHz, CDCl₃ 1.89 (s, 3H) 2.33 (s, 3H) 2.41 (s, 3H) 3.60 (s, 3H) 3.92 (s, 3H) 4.69-4.67 (d, J = 5.6 Hz, 2H) 5.97 (s, 1H) 6.81-6.78 (m, 1H) 7.48 (s, 1H) 7.59-7.57 (s, 1H) 8.12-8.11 (m, 1H) 8.72-8.70 (m, 1H) 12.04 (s, 1H) | 421 | 13H, 15 |
| 121 | (±)-7-(1-(1-(ethylsulfonyl)piperidin-4-yl)ethyl)-N-((4-methoxy-6-methyl-2-oxo-1,2-dihydropyridin-3-yl)methyl)-6-methylpyrrolo[1,2-b]pyridazine-5-carboxamide | (400 MHz, Methanol-d4) 1.11-1.12 (m, 2H), 1.32-1.37(m, 3H), 1.42 (d, J = 7.2 Hz, 2H) 2.10 (d, J = 13.2 Hz, 1H), 2.21(m, 1H), 2.31(s, 3H), 2.47(s, 3H), 2.50-2.57 (m, 1H), 2.75-2.88(m, 4H), 3.60 (d, J = 12 Hz, 2H), 3.7-4.0 (m, 4H), 4.64-4.67 (m, 2H), 5.97 (s, 1H), 6.56-6.61 (m, 1H) C7.40-7.43(m, 1H), 8.00-8.02 (m, 1H), 8.46 (d, J = 8.6 Hz, 1H) | 530 | 13L, 15 |

| Compound | Name | ¹H NMR | LCMS | Starting Materials |
|---|---|---|---|---|
| 122 | 7-(1,4-dimethyl-1H-pyrazol-3-yl)-N-((4-methoxy-6-methyl-2-oxo-1,2-dihydropyridin-3-yl)methyl)-6-methylpyrrolo[1,2-b]pyridazine-5-carboxamide | (400 MHz, Methanol-d4) 2.02 (s, 3H) 2.47 (s, 3H) 2.58 (s, 3H) 4.12 (s, 3H) 4.16 (s, 3H) 4.63 (s, 2H) 7.03 (s, 1H) 7.09-7.07 (m, 1H) 8.02 (s, 1H) 8.17-8.14 (m, 0.5H) 8.31-8.30 (m, 1H) 8.39-8.37 (m, 1H) 8.92-8.69 (m, 0.5 H) | 421 | 13G, 15 |
| 123 | 7-(3,5-dimethylisoxazol-4-yl)-6-methyl-N-((6-methyl-2-oxo-4-propyl-1,2-dihydropyridin-3-yl)methyl)pyrrolo[1,2-b]pyridazine-5-carboxamide | (400 MHz, CDCl₃) δ: 1.01 (t, J = 7.2 Hz, 3H), 1.62-1.66 (m, 2H), 2.08 (s, 3H), 2.45 (s, 6H), 2.37 (s, 3H), 2.73 (t, J = 7.6 Hz, 2H), 4.60 (d, J = 4 Hz, 2H), 5.95 (s, 1H), 6.74 (q, J = 4.4 Hz, 1H), 7.44-7.47 (brs, 1H), 8.06 (dd, J = 4 Hz, J = 1.6 Hz, 1H), 8.59 (d, J = 8 Hz, 1H), 11.11 (brs, 1H) | 434 | 13E, 16B |
| 124 | (±)-N-((4,6-dimethyl-2-oxo-1,2-dihydropyridin-3-yl)methyl)-6-methyl-7-(1-(1-methylpiperidin-4-yl)ethyl)pyrrolo[1,2-b]pyridazine-5-carboxamide | (400 MHz, MeOD) δ 1.89-1.96 (m, 3H), 2.20-2.16(d, J = 14.4 Hz, 3H), 2.37(s, 3H), 2.50(s, 3H), 2.62(s, 3H), 2.65(s, 2H), 2.87(m, 3H), 3.17 (m, 2H), 3.60 (d, J = 12 Hz, 2H), 4.13-4.19 (m, 1H), 4.57 (s, 2H), 6.58 (s, 1H), 7.15(m, 1H), 8.29-8.32 (d, J = 12 Hz, 1H), 8.46 (m, 1H) | 436 | 13P, 16 |

Example 17

Synthesis of (R or S)-7-(1-(N-ethylmethylsulfonamido)ethyl)-N-((4-methoxy-6-methyl-2-oxo-1,2-dihydropyridin-3-yl)methyl)-6-methylpyrrolo[1,2-b]pyridazine-5-carboxamide (Peak 1; Compound 107) and (R or S)-7-(1-(N-ethylmethylsulfonamido)ethyl)-N-((4-methoxy-6-methyl-2-oxo-1,2-dihydropyridin-3-yl)methyl)-6-methylpyrrolo[1,2-b]pyridazine-5-carboxamide (Peak 2; Compound 108)

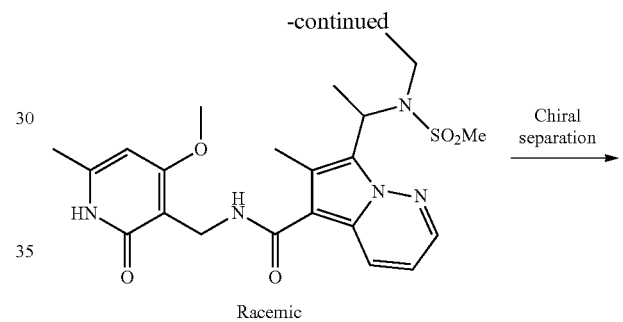

Racemic

Chiral separation →

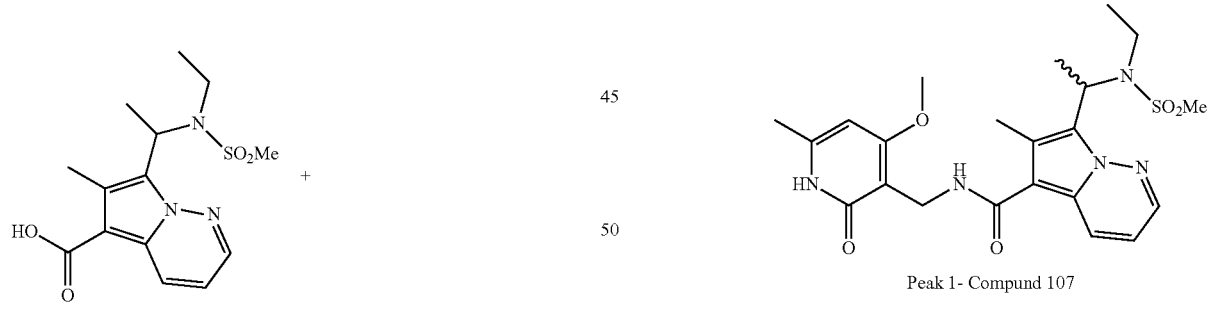

Peak 1- Compound 107

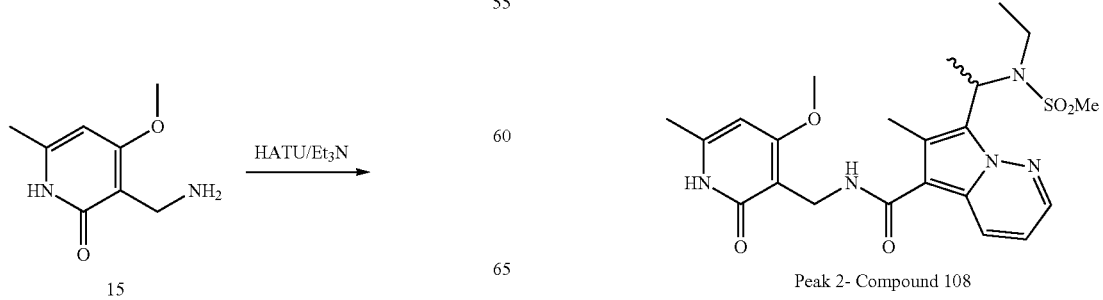

Peak 2- Compound 108

To a suspension of 7-(1-(N-ethylmethylsulfonamido)ethyl)-6-methylpyrrolo[1,2-b]pyridazine-5-carboxylic acid (13M; 130 mg, 0.4 mmol) in DMF (6 mL) was added TEA (202 mg, 2.0 mmol), 3-(aminomethyl)-4-methoxy-6-methylpyridin-2(1H)-one hydrochloride (15; 106 mg, 0.52 mmol) and HATU (303 mg, 0.8 mmol) at 25° C. under $N_2$. The reaction was stirred for 4 h before being diluted with EtOAc and washed with sat'd aqueous $NaHCO_3$. The organic layer was concentrated under vacuum and purified by preparatory HPLC (Column: Gemini 150*25 mm Mobile phase A: water with 0.1% $NH_3.H_2O$ solution Mobile phase B: MeCN 20-50-15) to give pure racemic title compound (20 mg, yield 10.5%)

The racemic mixture (18 mg) was separated via SFC (Column: AD (250*30 mm, Sum); Flow rate: 50 mL/min: Mobile: A, phase: 40% IPA+$NH_3.H_2O$, B, 60% $CO_2$; Wavelength: 220 nm) to give peak 1 (Compound 107; 3.9 mg) and peak 2 (Compound 108; 6.5 mg).

Peak 1: LCMS (M+H$^+$) m/z: calc'd 475.19; found 475.9. $^1$H NMR (CDCl3, 400 M Hz) d 11.79 (s, 1H), 8.53 (dd, $J_1$=1.6 Hz, $J_2$=8.8 Hz, 1H), 8.10 (dd, $J_1$=1.6 Hz, $J_2$=4.4 Hz, 1H), 7.45 (d, J=4.8 Hz, 1H), 6.71 (dd, $J_1$=4.4 Hz, $J_2$=9.2 Hz, 1H), 5.96 (s, 1H), 5.70 (dd, $J_1$=7.2 Hz, $J_2$=14.8 Hz, 1H), 4.63 (d, J=5.6 Hz, 2H), 3.91 (s, 3H), 3.67-3.48 (m, 1H), 3.37-3.30 (m, 1H), 2.62 (d, J=14.8 Hz, 6H), 2.31 (s, 3H), 1.87 (d, J=7.6 Hz, 3H), 0.95 (t, J=7.2 Hz, 3H).

Peak 2: LCMS (M+H$^+$) m/z: calc'd 475.19; found 476.0. $^1$H NMR (CDCl3, 400 M Hz) d 11.33 (s, 1H), 8.53 (dd, $J_1$=1.6 Hz, $J_2$=8.8 Hz, 1H), 8.10 (dd, $J_1$=1.6 Hz, $J_2$=4.4 Hz, 1H), 7.45 (d, J=4.8 Hz, 1H), 6.71 (dd, $J_1$=4.4 Hz, $J_2$=9.2 Hz, 1H), 5.96 (s, 1H), 5.70 (dd, $J_1$=7.2 Hz, $J_2$=14.8 Hz, 1H), 4.63 (d, J=5.6 Hz, 2H), 3.91 (s, 3H), 3.67-3.48 (m, 1H), 3.37-3.30 (m, 1H), 2.62 (d, J=14.8 Hz, 6H), 2.31 (s, 3H), 1.87 (d, J=7.6 Hz, 3H), 0.95 (t, J=7.2 Hz, 3H).

Compound 101 was separated into its isolated enantiomers according to the procedure described in this Example. The separated enantiomers were characterized as below:

Example 18

Synthesis of 7-(1-(1-(2,2-difluoropropanoyl)piperidin-4-yl)ethyl)-N-((4-methoxy-6-methyl-2-oxo-1,2-dihydropyridin-3-yl)methyl)-6-methylpyrrolo[1,2-b]pyridazine-5-carboxamide (Compound 135)

Step 1: Synthesis of 7-(1-(1-((benzyloxy)carbonyl)piperidin-4-yl)ethyl)-6-methylpyrrolo[1,2-b]pyridazine-5-carboxylic acid

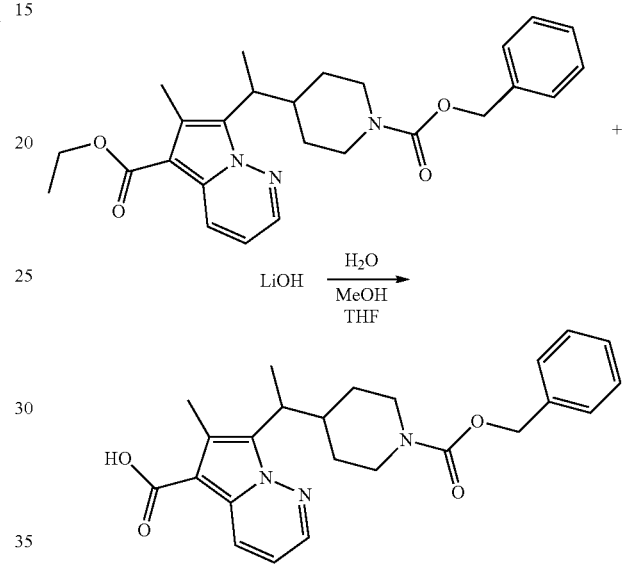

To a solution of ethyl 7-(1-(1-((benzyloxy)carbonyl)piperidin-4-yl)ethyl)-6-methylpyrrolo[1,2-b]pyridazine-5-carboxylate (6D; 450 mg, 1.0 mmol) in MeOH (3.0 mL), THF (3.0 mL), and water (2.0 mL) was added lithium hydroxide hydrate (420 mg, 10.0 mmol) and the reactions was stirred at reflux for 24 hours. The reaction solution was concentrated and the residue was adjusted pH to 3~4 with 1.0 M HCl. The solution was then extracted with EtOAc and the combined organics phase was washed with brine, dried over $Na_2SO_4$, filtered, and concentrated to afford 7-(1-(1-((ben-

| Compound No. | Name | $^1$H | LCMS |
|---|---|---|---|
| 105 (Peak 1) | (R or S)-N-((4-methoxy-6-methyl-2-oxo-1,2-dihydropyridin-3-yl)methyl)-6-methyl-7-(1-phenylethyl)pyrrolo[1,2-b]pyridazine-5-carboxamide | (400 MHz, CDCl$_3$) δ 8.44-8.46 (m, 1H) 8.00-8.01 (dd, 1H) 7.17-7.24 (t, 5H) 7.14-7.17 (s, 1H) 6.56-6.59 (t, 1H) 5.94 (s, 1H) 5.04-5.10 (t, 1H) 4.60-4.62 (m, 2H,) 3.89 (s, 3 H) 2.35 (s, 3 H), 2.99 (s, 3H) 1.76-1.78 (m, 3H) | 431 |
| 106 Peak 2 | (R or S)-N-((4-methoxy-6-methyl-2-oxo-1,2-dihydropyridin-3-yl)methyl)-6-methyl-7-(1-phenylethyl)pyrrolo[1,2-b]pyridazine-5-carboxamide | (400 MHz, CDCl$_3$) δ 8.44-8.46 (m, 1H) 8.00-8.01 (dd, 1H) 7.17-7.24 (t, 5H) 7.14-7.17 (s, 1H) 6.56-6.59 (t, 1H) 5.94 (s, 1H) 5.04-5.10 (t, 1H) 4.60-4.62 (m, 2H,) 3.89 (s, 3 H) 2.35 (s, 3 H), 2.99 (s, 3H) 1.76-1.78 (m, 3H) | 431 | zyloxy)carbonyl)piperidin-4-yl)ethyl)-6-methylpyrrolo[1,2-b]pyridazine-5-carboxylic acid (390 mg, 92% yield). LCMS (M+H⁺) m/z 422.

Step 2: Synthesis of benzyl 4-(1-(5-(((4-methoxy-6-methyl-2-oxo-1,2-dihydropyridin-3-yl)methyl)carbamoyl)-6-methylpyrrolo[1,2-b]pyridazin-7-yl)ethyl)piperidine-1-carboxylate

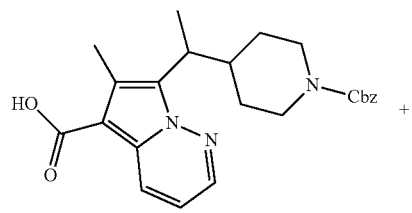

To a solution of 7-(1-(1-((benzyloxy)carbonyl)piperidin-4-yl)ethyl)-6-methylpyrrolo[1,2-b]pyridazine-5-carboxylic acid (390 mg, 0.925 mmol) in dichloromethane (10.0 mL) was added 3-(aminomethyl)-4-methoxy-6-methylpyridin-2(1H)-one hydrochloride (284 mg, 1.39 mmol), (1-cyano-2-ethoxy-2-oxoethylidenaminooxy)dimethylamino-morpholino-carbenium hexafluorophosphate (475 mg, 1.11 mmol)(COMU), and triethylamine (468 mg, 4.63 mmol). The reaction was stirred at 25° C. for 17 h before the reaction mixture was filtered. The filtrate was concentrated and the crude residue was purified by silica gel chromatography (eluent: dichloromethane/MeOH=50/1) to afford benzyl 4-(1-(5-(((4-methoxy-6-methyl-2-oxo-1,2-dihydropyridin-3-yl)methyl)carbamoyl)-6-methylpyrrolo[1,2-b]pyridazin-7-yl)ethyl)piperidine-1-carboxylate (500 mg, yield 94%). LCMS (M+H⁺) m/z 572.

Step 3: Synthesis of N-((4-methoxy-6-methyl-2-oxo-1,2-dihydropyridin-3-yl)methyl)-6-methyl-7-(1-(piperidin-4-yl)ethyl)pyrrolo[1,2-b]pyridazine-5-carboxamide

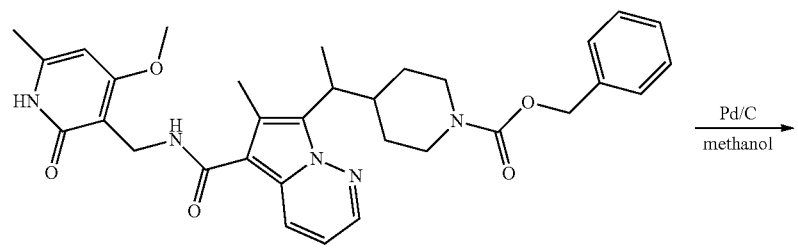

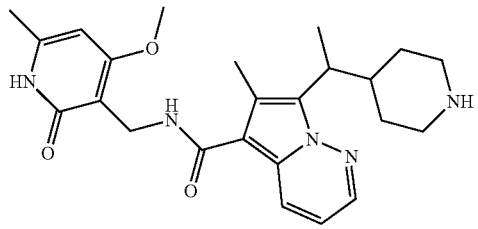

-continued

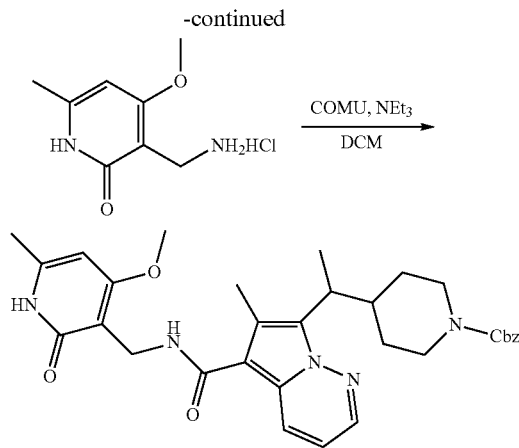

To a solution of benzyl 4-(1-(5-(((4-methoxy-6-methyl-2-oxo-1,2-dihydropyridin-3-yl)methyl)carbamoyl)-6-methylpyrrolo[1,2-b]pyridazin-7-yl)ethyl)piperidine-1-carboxylate (500 mg, 0.875 mmol) in MeOH (10.0 mL) was added palladium on carbon (200 mg, 10 wt % Pd) and the reaction was stirred under hydrogen at 25° C. for 2.5 hours. The reaction mixture was then filtered and the filtrate was concentrated to give N-((4-methoxy-6-methyl-2-oxo-1,2-dihydropyridin-3-yl)methyl)-6-methyl-7-(1-(piperidin-4-yl)ethyl)pyrrolo[1,2-b]pyridazine-5-carboxamide (350 mg, yield 91%). LCMS (M+H⁺) m/z 438.

Step 4: Synthesis of 7-(1-(1-(2,2-difluoropropanoyl)piperidin-4-yl)ethyl)-N-((4-methoxy-6-methyl-2-oxo-1,2-dihydropyridin-3-yl)methyl)-6-methylpyrrolo[1,2-b]pyridazine-5-carboxamide (Compound 135)

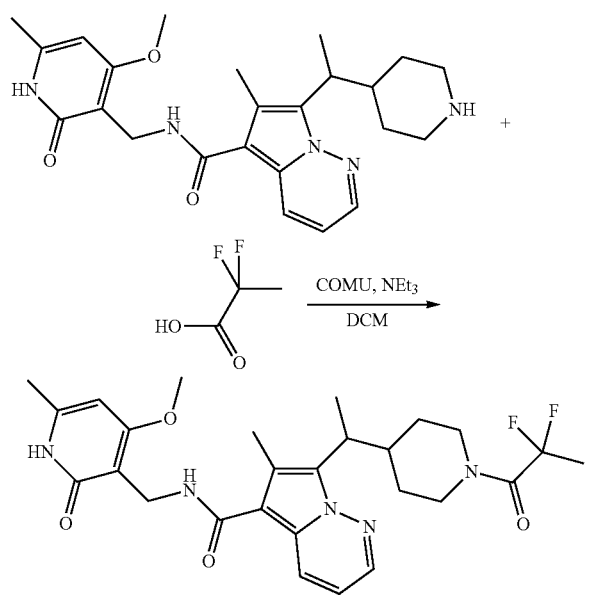

To a solution of N-((4-methoxy-6-methyl-2-oxo-1,2-dihydropyridin-3-yl)methyl)-6-methyl-7-(1-(piperidin-4-yl)ethyl)pyrrolo[1,2-b]pyridazine-5-carboxamide (80 mg, 0.183 mmol) in dichloromethane (3.0 mL) was added 2,2-difluoropropanoic acid (30.0 mg, 0.274 mmol), (1-cyano-2-ethoxy-2-oxoethylidenaminooxy)dimethylamino-morpholino-carbenium hexafluorophosphate (94 mg, 0.219 mmol) (COMU), and triethylamine (92.5 mg, 0.914 mmol). The reaction was stirred at room temperature for 3 h before the reaction mixture was concentrated. The crude residue was purified by preparative-HPLC (Condition: Column: ASB C18 150*25 mm; Mobile phase A: MeCN; Mobile phase B: water with 0.1% HCl; column temperature: 30° C.; Gradient: B in A, 34-64%; Flow rate: 25 ml/min) to afford 7-(1-(1-(2,2-difluoropropanoyl)piperidin-4-yl)ethyl)-N-((4-methoxy-6-methyl-2-oxo-1,2-dihydropyridin-3-yl)methyl)-6-methylpyrrolo[1,2-b]pyridazine-5-carboxamide (5.6 mg, 6% yield). LCMS (M+H$^+$) m/z: 530. $^1$H NMR (400 MHz, MeOH-d$_4$) δ 8.22-8.15 (m, 2H), 6.83-6.76 (m, 2H), 4.55 (br. s., 2H), 4.33 (d, J=13.4 Hz, 1H), 4.24 (d, J=12.8 Hz, 1H), 4.07 (s, 3H), 3.19-3.11 (m, 1H), 2.99-2.88 (m, 1H), 2.80-2.74 (m, 1H), 2.55 (br. s., 1H), 2.48 (br. s., 3H), 2.42 (s, 3H), 2.16 (d, J=13.2 Hz, 1H), 1.83-1.69 (m, 3H), 1.43 (d, J=7.2 Hz, 3H), 1.29-1.21 (m, 1H), 1.06 (br. s., 1H), 1.01-0.91 (m, 1H)

The following compounds were synthesized following step 4 using the appropriate starting materials and modifications:

| Compound No. | Name | 1H NMR | LCMS |
|---|---|---|---|
| 136 | 7-(1-(1-(2-fluoro-2-methylpropanoyl)piperidin-4-yl)ethyl)-N-((4-methoxy-6-methyl-2-oxo-1,2-dihydropyridin-3-yl)methyl)-6-methylpyrrolo[1,2-b]pyridazine-5-carboxamide | $^1$H NMR (400 MHz, MeOH-d$_4$) δ 8.19 (d, J = 5.6 Hz, 2H), 6.87 (br. s., 1H), 6.84-6.80 (m, 1H), 4.56 (br. s., 2H), 4.26 (d, J = 12.0 Hz, 1H), 4.09 (s, 3H), 3.21 (br. s., 1H), 3.12 (br. s., 1H), 2.89 (br. s., 1H), 2.66 (d, J = 12.0 Hz, 1H), 2.51 (s, 3H), 2.43 (s, 3H), 2.14 (d, J = 12.4 Hz, 1H), 1.55 (br. s., 6H), 1.44 (d, J = 7.2 Hz, 3H), 1.35-1.16 (m, 2H), 1.08-0.96 (m, 2H) | 526 |
| 137 | N-((4-methoxy-6-methyl-2-oxo-1,2-dihydropyridin-3-yl)methyl)-6-methyl-7-(1-(1-(3,3,3-trifluoropropanoyl)piperidin-4-yl)ethyl)pyrrolo[1,2-b]pyridazine-5-carboxamide | 1H NMR (400 MHz, MeOH-d4) δ 8.18 (d, J = 7.6 Hz, 2H), 6.89 (s, 1H), 6.84-6.80 (m, 1H), 4.56 (s, 2H), 4.31 (d, J = 13.6 Hz, 1H), 4.10 (s, 3H), 3.98 (d, J = 13.0 Hz, 1H), 3.70 (d, J = 13.4 Hz, 1H), 3.48-3.44 (m, 1H), 3.38-3.35 (m, 1H), 3.18-3.09 (m, 1H), 2.98-2.86 (m, 1H), 2.73-2.62 (m, 1H), 2.52 (s, 3H), 2.43 (s, 4H), 2.13 (t, J = 12.0 Hz, 1H), 1.44 (d, J = 7.2 Hz, 3H), 1.06-1.00 (m, 1H), 0.99-0.88 (m, 1H) | 548 |
| 138 | 7-(1-(1-(2,2-difluoroacetyl)piperidin-4-yl)ethyl)-N-((4-methoxy-6-methyl-2-oxo-1,2-dihydropyridin-3-yl)methyl)-6-methylpyrrolo[1,2-b]pyridazine-5-carboxamide | $^1$H NMR (400 MHz, MeOH-d$_4$) δ 8.19 (d, J = 7.2 Hz, 2H), 6.91 (s, 1H), 6.86-6.81 (m, 1H), 6.40-6.31 (m, 1H), 4.56 (s, 2H), 4.51 (d, J = 13.6 Hz, 1H), 4.24 (d, J = 13.2 Hz, 1H), 4.10 (s, 3H), 3.79 (d, J = 14.0 Hz, 1H), 3.21-3.12 (m, 1H), 3.00-2.89 (m, 1H), 2.78 (t, J = 12.0 Hz, 1H), 2.53 (s, 3H), 2.46-2.41 (m, 3H), 2.17 (br. s., 1H), 1.44 (d, J = 6.8 Hz, 3H), 1.31-1.22 (m, 1H), 1.10-1.05 (m, 1H), 1.04-0.94 (m, 1H) | 516 |
| 139 | N-((4-methoxy-6-methyl-2-oxo-1,2-dihydropyridin-3-yl)methyl)-6-methyl-7-(1-(1-(2,2,2-trifluoroacetyl)piperidin-4-yl)ethyl)pyrrolo[1,2-b]pyridazine-5-carboxamide | $^1$H NMR (400 MHz, MeOH-d$_4$) δ 8.16 (d, J = 9.2 Hz, 1H), 8.09 (dd, J = 1.2, 4.4 Hz, 1H), 6.70 (dd, J = 4.4, 8.8 Hz, 1H), 6.25 (s, 1H), 4.49 (s, 2H), 4.25 (d, J = 13.6 Hz, 1H), 4.06 (s, 3H), 3.92 (s, 3H), 3.80 (d, J = 13.2 Hz, 0.5H), 3.22 (d, J = 12.0 Hz, 1H), 3.02 (t, J = 12.0 Hz, 0.5H), 2.87 (t, J = 12.0 Hz, 0.5H), 2.65 (t, J = 12.0 Hz, 1H), 2.54-2.46 (m, 1H), 2.44-2.37 (m, 3H), 2.30 (s, 3H), 2.19 (d, | 534 |

J = 13.6 Hz, 1H), 1.43 (d, J = 7.2 Hz, 3H), 1.31-1.23 (m, 1H), 1.13 (br. s., 1H), 1.07-0.97 (m, 1H)

Example 19

Synthesis of N-((4-methoxy-6-methyl-2-oxo-1,2-dihydropyridin-3-yl)methyl)-6-methyl-7-(1-(1-(3,3,3-trifluoropropyl)piperidin-4-yl)ethyl)pyrrolo[1,2-b]pyridazine-5-carboxamide (Compound 134)

Step 1: Synthesis of ethyl 6-methyl-7-(1-(1-(3,3,3-trifluoropropyl)piperidin-4-yl)ethyl)pyrrolo[1,2-b]pyridazine-5-carboxylate

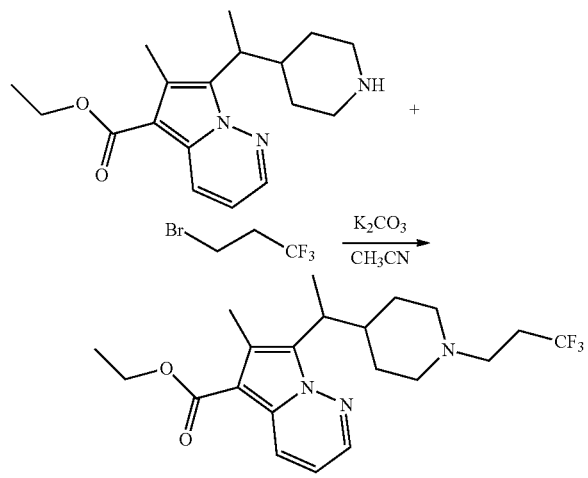

A mixture of ethyl 6-methyl-7-(1-(piperidin-4-yl)ethyl)pyrrolo[1,2-b]pyridazine-5-carboxylate (11A, 50 mg, 0.16 mmol), 3-bromo-1,1,1-trifluoropropane (42 mg, 0.28 mmol) and potassium carbonate (65 mg, 0.48 mmol) in acetonitrile (5 mL) was stirred at 50° C. for 5 hours under nitrogen. The mixture was diluted with EtOAc (50 ml) and water (50 ml). The layers were separated and the organic layer was dried over Na$_2$SO$_4$, filtered, and concentrated to afford ethyl 6-methyl-7-(1-(1-(3,3,3-trifluoropropyl)piperidin-4-yl)ethyl)pyrrolo[1,2-b]pyridazine-5-carboxylate (50 mg yellow oil, 77% yield). LCMS (M+H$^+$) m/z 412.

Step 2: Synthesis of 6-methyl-7-(1-(1-(3,3,3-trifluoropropyl)piperidin-4-yl)ethyl)pyrrolo[1,2-b]pyridazine-5-carboxylic acid

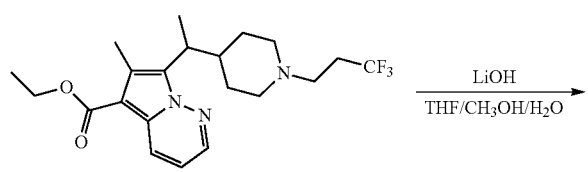

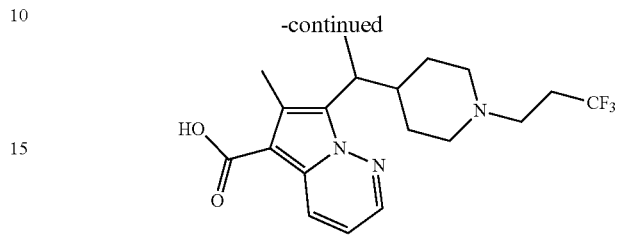

A mixture of ethyl 6-methyl-7-(1-(1-(3,3,3-trifluoropropyl)piperidin-4-yl)ethyl)pyrrolo[1,2-b]pyridazine-5-carboxylate (50 mg, 0.122 mmol) and lithium hydroxide (29.1 mg, 1.22 mmol) dissolved in MeOH (2 mL), water (1 mL), and THF (1 mL) was stirred at 60° C. for 16 hours under nitrogen. The reaction solution was acidified with aqueous hydrochloric acid (1M) to pH=5 and diluted with EtOAc (50 ml) and water (50 ml). The layers were separated and the organic layer was dried over Na$_2$SO$_4$, filtered, and concentrated to afford 6-methyl-7-(1-(1-(3,3,3-trifluoropropyl)piperidin-4-yl)ethyl)pyrrolo[1,2-b]pyridazine-5-carboxylic acid (40 mg yellow solid, 86% yield). LCMS (M+H$^+$) m/z 384.

Step 3: Synthesis of N-((4-methoxy-6-methyl-2-oxo-1,2-dihydropyridin-3-yl)methyl)-6-methyl-7-(1-(1-(3,3,3-trifluoropropyl)piperidin-4-yl)ethyl)pyrrolo[1,2-b]pyridazine-5-carboxamide

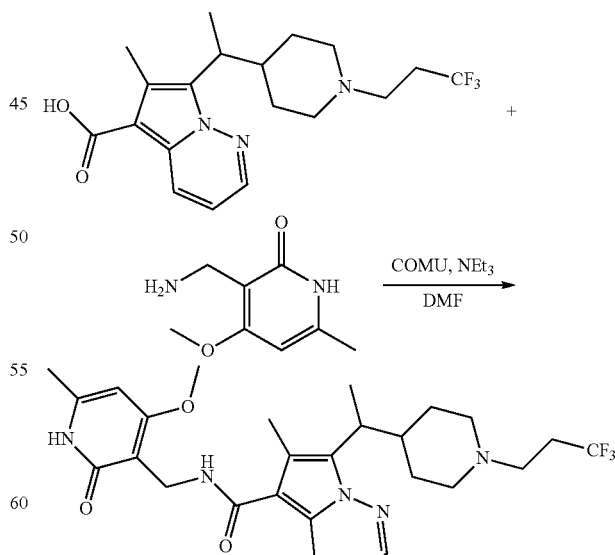

A mixture of 6-methyl-7-(1-(1-(3,3,3-trifluoropropyl)piperidin-4-yl)ethyl)pyrrolo[1,2-b]pyridazine-5-carboxylic acid (40 mg, 0.104 mmol), 3-(aminomethyl)-4-methoxy-6- methylpyridin-2(1H)-one (22 mg, 0.125 mmol), triethylamine (32 mg, 0.313 mmol), and (1-cyano-2-ethoxy-2-oxoethylidenaminooxy)dimethylamino-morpholino-carbenium hexafluorophosphate (54 mg, 0.125 mmol) in DMF (3 mL) was stirred at 20° C. for 3 h under a nitrogen atmosphere. The mixture was washed with brine (5 mL), dried over Na$_2$SO$_4$, filtered, and concentrated to give the crude product. The crude product was separated by preparative HPLC (Condition: Column: ASB C18 150*25 mm; A: Water+0.1% HCl; B: CH$_3$CN; column temperature: 30° C.; Gradient: B in A 12~42%) to afford N-((4-methoxy-6-methyl-2-oxo-1,2-dihydropyridin-3-yl)methyl)-6-methyl-7-(1-(1-(3,3,3-trifluoropropyl)piperidin-4-yl)ethyl)pyrrolo[1,2-b]pyridazine-5-carboxamide (15.4 mg, blue oil, 28% yield). LCMS (M+H+) m/z 534. $^1$H NMR (400 MHz, MeOD) δ 8.23-8.17 (m, 2H), 6.85-6.89 (m, 2H), 4.55 (s, 2H), 4.07 (s, 3H), 3.71-3.64 (d, J=24 Hz, 1H), 3.41-3.36 (m, 1H), 3.11-3.10 (m, 2H), 2.79-2.75 (m, 3H), 2.49 (s, 3H), 2.45 (s, 3H), 2.45-2.35 (d, J=36.8 Hz, 1H), 1.59-1.56 (m, 2H), 1.47-1.45 (d, J=7.2 Hz, 3H), 1.39-1.36 (m, 1H), 1.32-1.26 (m, 2H).

Example 20

Synthesis of ethyl 7-(1-(1-(2-fluoro-2-methylpropanoyl)piperidin-4-yl)ethyl)-6-methylpyrrolo[1,2-b]pyridazine-5-carboxylate (Compound 144)

Step 1: Synthesis of ethyl 7-(1-(1-(2-fluoro-2-methylpropanoyl)piperidin-4-yl)ethyl)-6-methylpyrrolo[1,2-b]pyridazine-5-carboxylate (Intermediate 17A)

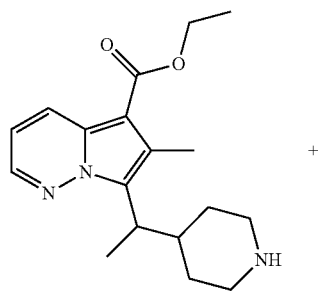

+

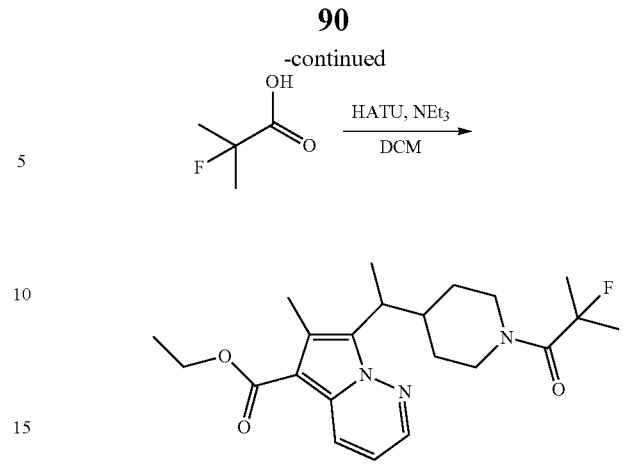

A mixture of ethyl 6-methyl-7-(1-(piperidin-4-yl)ethyl)pyrrolo[1,2-b]pyridazine-5-carboxylate (50 mg, 0.16 mmol), 2-fluoro-2-methylpropanoic acid (20 mg, 0.19 mmol), 2-(3H-[1,2,3]triazolo[4,5-b]pyridin-3-yl)-1,1,3,3-tetramethylisouronium hexafluorophosphate(V) (72 mg, 0.19 mmol) and triethylamine (48 mg, 0.48 mmol) in dichloromethane (5 mL) was stirred at 20° C. for 3 h under nitrogen. The mixture was diluted with EtOAc (50 ml) and water (50 ml). The layers were separated and the organic layer was dried over Na$_2$SO$_4$, filtered, and concentrated to afford crude material, which was purified by prep-TLC (petroleum ether: EtOAc=10:1) to afford ethyl 7-(1-(1-(2-fluoro-2-methylpropanoyl)piperidin-4-yl)ethyl)-6-methyl-pyrrolo[1,2-b]pyridazine-5-carboxylate (50 mg yellow oil, 78% yield). LCMS (M+H$^+$) m/z 404.

The following intermediates were synthesized in a similar manner to ethyl 7-(1-(1-(2-fluoro-2-methylpropanoyl)piperidin-4-yl)ethyl)-6-methylpyrrolo[1,2-b]pyridazine-5-carboxylate using the appropriate starting materials and modifications:

| Intermediate # | Structure | Name | LCMS m/z |
|---|---|---|---|
| 17B | ![structure] | ethyl 7-(1-(1-(2,2-difluoropropanoyl)piperidin-4-yl)ethyl)-6-methylpyrrolo[1,2-b]pyridazine-5-carboxylate | 408 |
| 17C | ![structure] | ethyl 7-(1-(1-(2,2-difluoroacetyl)piperidin-4-yl)ethyl)-6-methylpyrrolo[1,2-b]pyridazine-5-carboxylate | 394 |

| Intermediate # | Structure | Name | LCMS m/z |
|---|---|---|---|
| 17D | 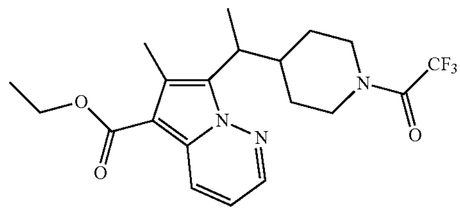 [SMILES: CCOC(=O)c1c(C)c(C(C)C2CCN(C(=O)C(F)(F)F)CC2)n2ncccc12] | ethyl 6-methyl-7-(1-(1-(2,2,2-trifluoroacetyl)piperidin-4-yl)ethyl)pyrrolo[1,2-b]pyridazine-5-carboxylate | 412 |
| 17E | 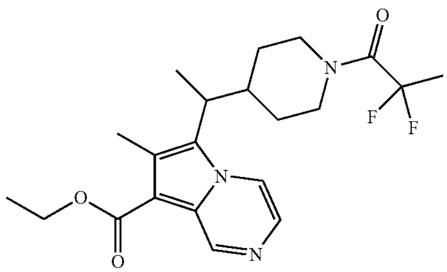 [SMILES: CCOC(=O)c1c(C)c(C(C)C2CCN(C(=O)C(C)(F)F)CC2)n2ccncc12] | ethyl 6-(1-(1-(2,2-difluoropropanoyl)piperidin-4-yl)ethyl)-7-methylpyrrolo[1,2-a]pyrazine-8-carboxylate | ND |

Step 2: Synthesis of ethyl 7-(1-(1-(2-fluoro-2-methylpropyl)piperidin-4-yl)ethyl)-6-methylpyrrolo[1,2-b]pyridazine-5-carboxylat (Intermediate 18A)

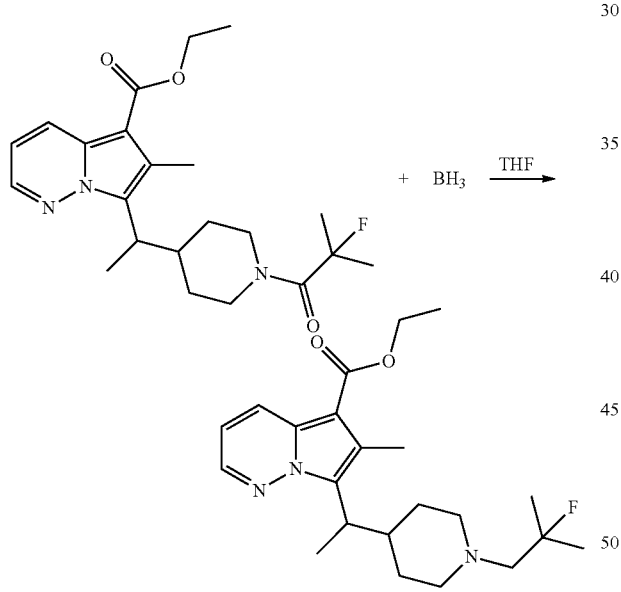

To a solution of ethyl 7-(1-(1-(2-fluoro-2-methylpropanoyl)piperidin-4-yl)ethyl)-6-methylpyrrolo[1,2-b]pyridazine-5-carboxylate (50 mg, 0.13 mmol) in THF (3 mL) was added borane (2 mL, 10M/L) dropwise at 25° C. It was stirred at 25° C. for 2 h before being quenched by addition of MeOH (5 mL) at 0° C. The solution was diluted with EtOAc (50 ml) and water (50 ml). The layers were separated and the organic layer was dried over Na$_2$SO$_4$, filtered, and concentrated to afford crude material which was purified by prep-TLC (petroleum ether: EtOAc=3:1) to afford ethyl 7-(1-(1-(2-fluoro-2-methylpropyl)piperidin-4-yl)ethyl)-6-methylpyrrolo[1,2-b]pyridazine-5-carboxylate (30 mg yellow oil, 62% yield). LCMS (M+H$^+$) m/z 390.

The following intermediates were synthesized in a similar manner to ethyl 7-(1-(1-(2-fluoro-2-methylpropyl)piperidin-4-yl)ethyl)-6-methylpyrrolo[1,2-b]pyridazine-5-carboxylate using the appropriate starting materials and modifications:

| Intermediate # | Structure | Name | LCMS |
|---|---|---|---|
| 18B | 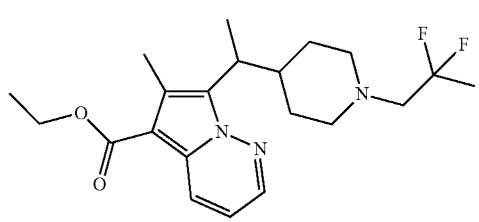 [SMILES: CCOC(=O)c1c(C)c(C(C)C2CCN(CC(C)(F)F)CC2)n2ncccc12] | ethyl 7-(1-(1-(2,2-difluoropropyl)piperidin-4-yl)ethyl)-6-methylpyrrolo[1,2-b]pyridazine-5-carboxylate | 394 |

| Intermediate # | Structure | Name | LCMS |
|---|---|---|---|
| 18C | 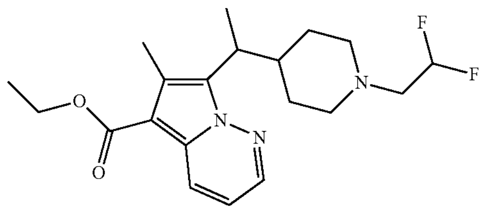 [SMILES: CCOC(=O)c1c(C)c(C(C)C2CCN(CC(F)F)CC2)n2ncccc12] | ethyl 7-(1-(1-(2,2-difluoroethyl)piperidin-4-yl)ethyl)-6-methylpyrrolo[1,2-b]pyridazine-5-carboxylate | 380 |
| 18D | 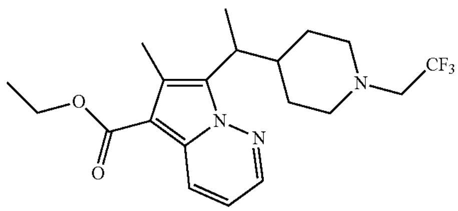 [SMILES: CCOC(=O)c1c(C)c(C(C)C2CCN(CC(F)(F)F)CC2)n2ncccc12] | ethyl 6-methyl-7-(1-(1-(2,2,2-trifluoroethyl)piperidin-4-yl)ethyl)pyrrolo[1,2-b]pyridazine-5-carboxylate | 398 |
| 18E | 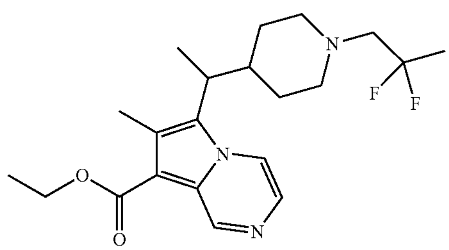 [SMILES: CCOC(=O)c1c(C)c(C(C)C2CCN(CC(C)(F)F)CC2)n2ccncc12] | ethyl 6-(1-(1-(2,2-difluoropropyl)piperidin-4-yl)ethyl)-7-methylpyrrolo[1,2-a]pyrazine-8-carboxylate | ND |

Step 3: Synthesis of 7-(1-(1-(2-fluoro-2-methylpropyl)piperidin-4-yl)ethyl)-6-methylpyrrolo[1,2-b]pyridazine-5-carboxylic acid (Intermediate 19A)

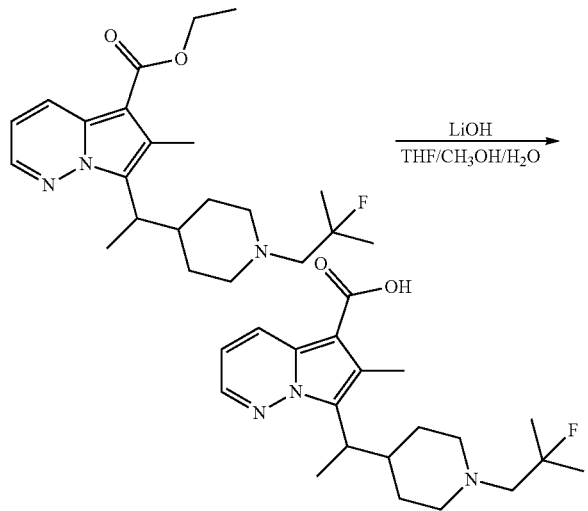

A mixture of ethyl 7-(1-(1-(2-fluoro-2-methylpropyl)piperidin-4-yl)ethyl)-6-methylpyrrolo[1,2-b]pyridazine-5-carboxylate (30 mg, 0.07 mmol) and lithium hydroxide (19 mg, 0.77 mmol) in MeOH (2 mL), water (1 mL), and THF (1 mL) was stirred at 60° C. for 16 h under nitrogen. It was acidified with aqueous hydrochloric acid (1M) to pH=5 and diluted with EtOAc (50 ml) and water (50 ml). The layers were separated and the organic layer was dried over $Na_2SO_4$, filtered, and concentrated to afford 6-methyl-7-(1-(1-(2,2,2-trifluoroethyl)piperidin-4-yl)ethyl)pyrrolo[1,2-b]pyridazine-5-carboxylic acid (20 mg yellow solid, 72% yield). LCMS (M+H$^+$) m/z 362.

The following intermediates were synthesized in a similar manner to 7-(1-(1-(2-fluoro-2-methylpropyl)piperidin-4-yl)ethyl)-6-methylpyrrolo[1,2-b]pyridazine-5-carboxylic acid using the appropriate starting materials and modifications:

| Intermediate # | Structure | Name | LCMS |
|---|---|---|---|
| 19B | 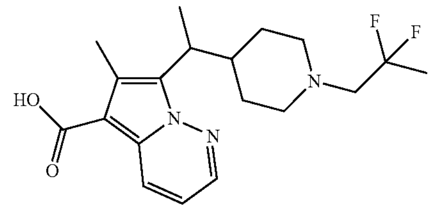 [SMILES: Cc1c(C(=O)O)c2cccnn2c1C(C)C1CCN(CC(C)(F)F)CC1] | 7-(1-(1-(2,2-difluoropropyl)piperidin-4-yl)ethyl)-6-methylpyrrolo[1,2-b]pyridazine-5-carboxylic acid | 366 |
| 19C | 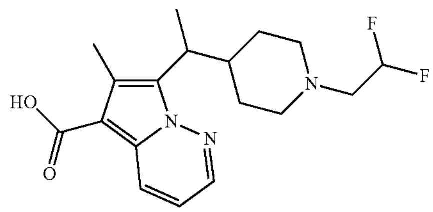 [SMILES: Cc1c(C(=O)O)c2cccnn2c1C(C)C1CCN(CC(F)F)CC1] | 7-(1-(1-(2,2-difluoroethyl)piperidin-4-yl)ethyl)-6-methylpyrrolo[1,2-b]pyridazine-5-carboxylic acid | 352 |
| 19D | 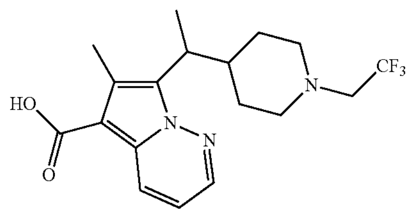 [SMILES: Cc1c(C(=O)O)c2cccnn2c1C(C)C1CCN(CC(F)(F)F)CC1] | 6-methyl-7-(1-(1-(2,2,2-trifluoroethyl)piperidin-4-yl)ethyl)pyrrolo[1,2-b]pyridazine-5-carboxylic acid | 370 |
| 19E | 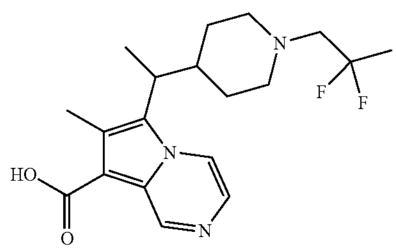 [SMILES: Cc1c(C(=O)O)c2cnccn2c1C(C)C1CCN(CC(C)(F)F)CC1] | 6-(1-(1-(2,2-difluoropropyl)piperidin-4-yl)ethyl)-7-methylpyrrolo[1,2-a]pyrazine-8-carboxylic acid | 366 |

Step 4: Synthesis of 7-(1-(1-(2-fluoro-2-methylpropyl)piperidin-4-yl)ethyl)-N-((4-methoxy-6-methyl-2-oxo-1,2-dihydropyridin-3-yl)methyl)-6-methylpyrrolo[1,2-b]pyridazine-5-carboxamide (Compound 144)

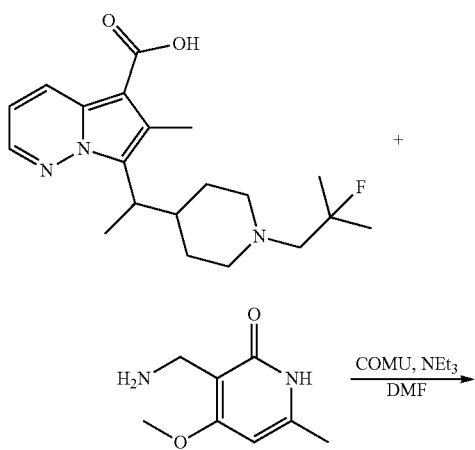

A mixture of 6-methyl-7-(1-(1-(2,2,2-trifluoroethyl)piperidin-4-yl)ethyl)pyrrolo[1,2-b]pyridazine-5-carboxylic acid (20 mg, 0.055 mmol), 3-(aminomethyl)-4-methoxy-6-methylpyridin-2(1H)-one (12 mg, 0.065 mmol), triethylamine (17 mg, 0.16 mmol), and (1-cyano-2-ethoxy-2-oxoethylidenaminooxy)dimethylamino-morpholino-carbenium hexafluorophosphate (29 mg, 0.066 mmol) in DMF (3 mL) was stirred at 20° C. for 3 hours under nitrogen. The mixture was partitioned between with EtOAc and water and the layers separated. The organic layer was dried over $Na_2SO_4$, filtered, and concentrated to afford crude material. The crude material was purified by preparative-HPLC (Instrument:

Gilson GX281; Condition: Column: Gemini 150*25 mm*Sum; Mobile phase A: water with 0.05% ammonia solution; Mobile phase B: MeCN; column temperature: 30° C.; Gradient: B in A 47-77%) to afford 7-(1-(1-(2-fluoro-2-methylpropyl)piperidin-4-yl)ethyl)-N-((4-methoxy-6-methyl-2-oxo-1,2-dihydropyridin-3-yl)methyl)-6-methyl-pyrrolo[1,2-b]pyridazine-5-carboxamide (3.6 mg, 13% yield). LCMS (M+H$^+$) m/z 512. $^1$H NMR (400 MHz, CD$_3$OD): δ 8.15-8.13 (d, J=9.2 Hz, 1H), 8.09-8.08 (t, J=4.4 Hz, 1H), 6.70-6.66 (dd, J$_1$=9.2 Hz, J$_2$=9.2 Hz, 2H), 6.26 (s, 1H),4.60 (s, 2H), 4.69 (s, 2H), 3.9 (s, 3H), 3.72 (s, 1H), 2.95 (s, 2H), 2.77-2.74 (s, J=12.0 Hz, 2H), 2.41 (s, 3H),2.35 (s, 1H), 2.30 (s, 3H), 1.97 (s, 1H), 1.40-1.38 (d, J=6.8 Hz, 3H), 1.32-1.31 (d, J=3.2 Hz, 3H), 1.27-1.26 (d, J=3.2 Hz, 3H), 1.13 (m, 1H), 1.01-0.93 (m, 2H).

The following compounds were synthesized in a similar manner to Compound 144 using the appropriate intermediates:

| Compound Number | Name | 1H NMR | LCMS | Intermediates Used |
|---|---|---|---|---|
| 143 | 7-(1-(1-(2,2-difluoropropyl)piperidin-4-yl)ethyl)-N-((4-methoxy-6-methyl-2-oxo-1,2-dihydropyridin-3-yl)methyl)-6-methylpyrrolo[1,2-b]pyridazine-5-carboxamide | $^1$H NMR (400 MHz, CD$_3$OD) δ 8.20 (s, 1H), 8.18 (s, 1H), 6.88 (s, 1H), 6.86-6.83 (m, 1H), 4.56 (s, 2H), 4.11 (s, 3H), 3.77-3.68 (m, 2H), 3.52-3.49 (d, J = 11.2 Hz, 2H), 3.24-3.19(m, 2H), 3.19-2.98 (m, 1H), 2.52 (s, 3H) 2.46 (s, 3H), 2.36-2.33 (m, 2H), 1.69 (t, 3H), 1.47-1.45 (d, J = 7.2 Hz, 3H), 1.45-1.27 (m, 3H). | 516 | 11A, 19B |
| 145 | 7-(1-(1-(2,2-difluoroethyl)piperidin-4-yl)ethyl)-N-((4-methoxy-6-methyl-2-oxo-1,2-dihydropyridin-3-yl)methyl)-6-methylpyrrolo[1,2-b]pyridazine-5-carboxamide | $^1$H NMR (400 MHz, CD$_3$OD) δ 8.16-8.14 (d, J = 9.2 Hz, 1H), 8.09-8.08 (d, J = 4.4 Hz, 1H), 6.74-6.67 (dd, J1 = 8.8 Hz, J2 = 9.2 Hz, 1H), 6.26 (s, 1H), 6.11-5.83 (t, 1H), 4.59 (s, 2H), 4.49 (s, 2H), 3.92 (s, 3H), 3.19-3.12 (m, 2H), 2.82-2.64 (m, 2H), 2.41 (s, 3H), 2.23 (s, 3H), 2.20-2.00 (m, 3H), 1.41-1.40 (d, J = 7.2 Hz, 3H), 1.12-1.17 (m, 2H), 1.14-1.02 (m, 1H). | 502 | 11A, 19C |
| 133 | N-((4-methoxy-6-methyl-2-oxo-1,2-dihydropyridin-3-yl)methyl)-6-methyl-7-(1-(1-(2,2,2-trifluoroethyl)piperidin-4-yl)ethyl)pyrrolo[1,2-b]pyridazine-5-carboxamide | $^1$H NMR (400 MHz, CD$_3$OD) δ 8.29-8.12 (m, 2H), 7.02-6.81 (m, 2H), 4.67-4.49 (m, 2H), 4.30-4.06 (m, 4H), 3.83-3.65 (m, 2H), 3.59-3.41 (m, 2H), 3.16-3.02 (m, 1H), 2.84-2.67 (m, 2H), 2.60-2.40 (m, 5H), 2.38-2.29 (m, 1H), 1.80-1.21 (m, 7H) | 520 | 11A, 19D |
| 140 | 6-(1-(1-(2,2-difluoropropyl)piperidin-4-yl)ethyl)-N-((4-methoxy-6-methyl-2-oxo-1,2-dihydropyridin-3-yl)methyl)-7-methylpyrrolo[1,2-a]pyrazine-8-carboxamide | $^1$H NMR (400 MHz, MeOH-d4) δ 1.50 (m, 3H), 1.82-1.78 (m, 5H), 2.36-2.31 (m, 3H), 2.41 (s, 3H), 2.57 (s, 3H), 3.22-3.13 (m, 3H), 3.56-3.42 (m, 1H), 3.78 (m, 3H), 4.02 (s, 3H), 4.57 (m, 2H), 6.55 (s, 1H), 7.71-7.70 (m, 1H), 8.74 (m, 1H), 9.23 (s, 1H). | 516 | 11B, 19E |

Example 21

Synthesis of 6-chloro-N-((4,6-dimethyl-2-oxo-1,2-dihydropyridin-3-yl)methyl)-7-(1-(1-(2-hydroxy-2-methylpropyl)piperidin-4-yl)ethyl)pyrrolo[1,2-b]pyridazine-5-carboxamide (Compound 141)

Step 1. Synthesis of ethyl 7-(1-((benzyloxy)carbonyl)piperidine-4-carbonyl)pyrrolo[1,2-b]pyridazine-5-carboxylate

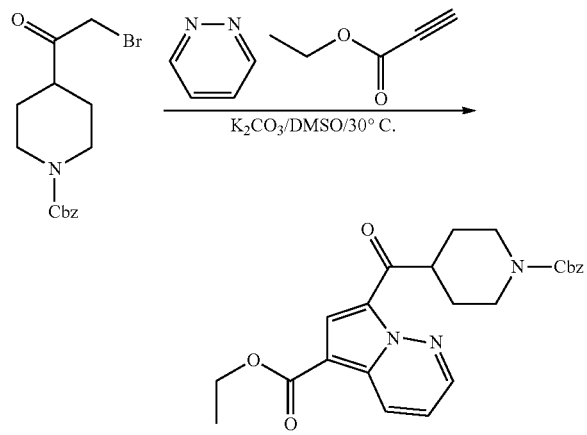

To a solution of benzyl 4-(2-bromoacetyl)piperidine-1-carboxylate (1F; 5.0 g, 14.7 mmol) in anhydrous (methylsulfinyl)methane (5 ml) were added ethyl propiolate (1.73 g, 17.6 mmol), potassium carbonate (5.07 g, 36.7 mmol) and pyridazine (1.41 g, 17.6 mmol). The reaction mixture was stirred at room temperature for 2.5 h. Then the reaction was quenched by water (20 ml) and extracted with EtOAc (30 mL×3). The combined organic layer was dried over Na2SO4 and concentrated to give the crude product and the crude product was purified by column chromatograph on silica gel (eluted: petrol ether/acetic ester=30:1~5:1) to afford ethyl 7-(1-((benzyloxy)carbonyl)piperidine-4-carbonyl)pyrrolo[1,2-b]pyridazine-5-carboxylate (1.9 g, 30%) as a brown oil.

Step 2. Synthesis of ethyl 7-(1-(1-((benzyloxy)carbonyl)piperidin-4-yl)-1-hydroxyethyl)pyrrolo[1,2-b]pyridazine-5-carboxylate

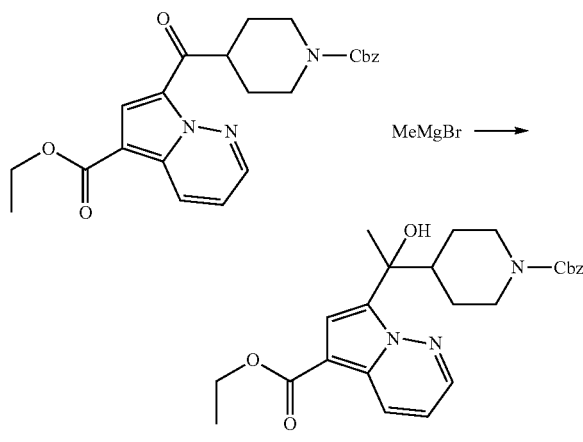

To a solution of ethyl 7-(1-(1-((benzyloxy)carbonyl)piperidin-4-yl)-1-hydroxyethyl)pyrrolo[1,2-b]pyridazine-5-carboxylate (1.9 g, 6.27 mmol) in anhydrous THF (22.5 mL) was added methylmagnesium bromide solution (9.5 mL, 2 mol/L) dropwise at −65° C. The resulting mixture was stirred at −65° C. for 2 hours. The reaction was quenched by saturated ammonium chloride (9 ml) at −20° C. The aqueous phase was extracted with EtOAc (50 ml×3) and the combined organic layers were dried over Na₂SO₄, filtered, and concentrated to give crude ethyl 7-(1-(1-((benzyloxy)carbonyl)piperidin-4-yl)-1-hydroxyethyl)pyrrolo[1,2-b]pyridazine-5-carboxylate as a red oil. It was used directly in the next step.

Step 3. Synthesis of ethyl 7-(1-(1-((benzyloxy)carbonyl)piperidin-4-yl)ethyl)pyrrolo[1,2-b]pyridazine-5-carboxylate

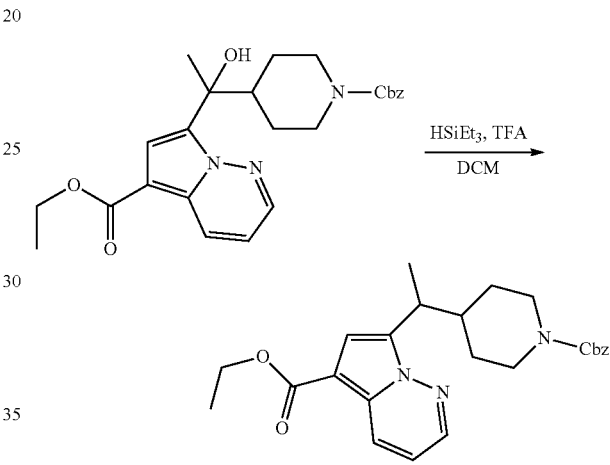

To a solution of ethyl 7-(1-(1-((benzyloxy)carbonyl)piperidin-4-yl)ethyl)pyrrolo[1,2-b]pyridazine-5-carboxylate (1.97 g, 4.36 mmol) in anhydrous dichloromethane (6.5 mL) was added triethylsilane (1.2 mL), trifluoroacetic acid (1.2 mL) at −20° C. The reaction mixture was stirred at −10° C. for 1 h. Then the reaction mixture was quenched by saturated sodium bicarbonate solution and extracted with EtOAc (40 ml×3). The combined organic layer was dried over Na₂SO₄, filtered, and concentrated to give crude product. The crude product was purified by column chromatograph on silica gel (eluted: petrol ether/acetic ester=35:1~20:1) to afford ethyl 7-(1-(1-((benzyloxy)carbonyl)piperidin-4-yl)ethyl)pyrrolo[1,2-b]pyridazine-5-carboxylate (1.53 g, 82% yield) as a yellow oil. LCMS (M+H⁺) m/z 436.

Step 4. Synthesis of ethyl 7-(1-(piperidin-4-yl)ethyl)pyrrolo[1,2-b]pyridazine-5-carboxylate

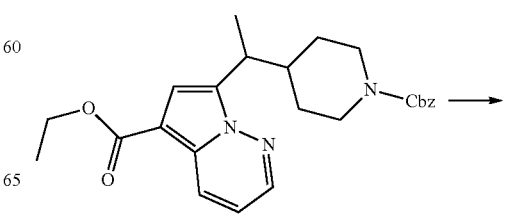

-continued

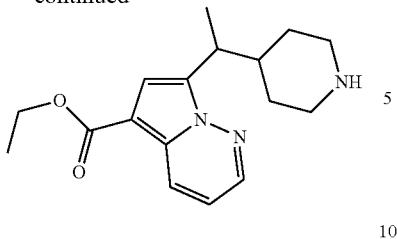

A mixture of compound ethyl 7-(1-(1-((benzyloxy)carbonyl)piperidin-4-yl)ethyl)pyrrolo[1,2-b]pyridazine-5-carboxylate (2.0 g, 4.6 mmol) and Pd/C (54.7 mg) in MeOH (30 mL) was stirred under hydrogen (1 atm) at room temperature for 18 hours. The reaction mixture was filtered and the filtrate was concentrated to give crude product. The crude product was used directly in the next step.

Step 5. Synthesis of ethyl 7-(1-(1-(tert-butoxycarbonyl)piperidin-4-yl)ethyl)pyrrolo[1,2-b]pyridazine-5-carboxylate

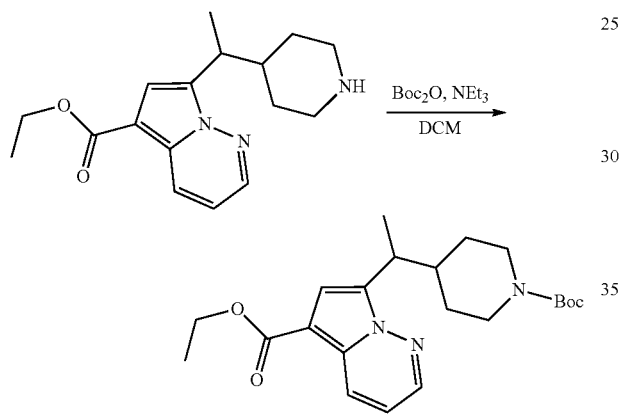

To a solution of ethyl 7-(1-(piperidin-4-yl)ethyl)pyrrolo[1,2-b]pyridazine-5-carboxylate (1.38 g, 4.59 mmol) in anhydrous dichloromethane (20 mL) were added triethylamine (926.7 mg, 9.16 mmol) and di-tert-butyl dicarbonate (2.0 g, 9.16 mmol). The reaction mixture was stirred at room temperature overnight. The reaction was quenched by water (20 mL) and extracted with EtOAc (100 mL×3). The combined organic layers were dried over Na$_2$SO$_4$, filtered, and concentrated. The crude product was purified by column chromatograph on silica gel (eluted: petrol ether/acetic ester=35:1~25:1) to give ethyl7-(1-(1-(tert-butoxycarbonyl)piperidin-4-yl)ethyl)pyrrolo[1,2-b]pyridazine-5-carboxylate (1.46 g, 79% yield). LCMS (M+H$^+$) m/z 302.

Step 6. Synthesis of ethyl 7-(1-(1-(tert-butoxycarbonyl)piperidin-4-yl)ethyl)-3,6-dichloropyrrolo[1,2-b]pyridazine-5-carboxylate

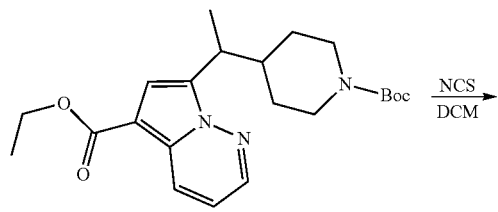

-continued

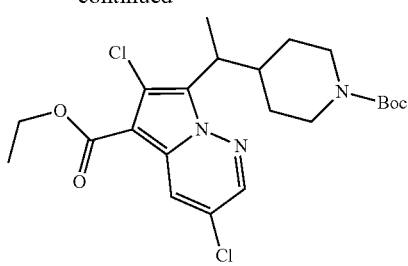

To a solution of compound ethyl7-(1-(1-(tert-butoxycarbonyl)piperidin-4-yl)ethyl)pyrrolo[1,2-b]pyridazine-5-carboxylate (1.0 g, 2.5 mmol) in anhydrous DMF was added NCS (655.2 mg, 5 mmol) in portions at −30° C. The reaction mixture was stirred at room temperature for 10 hours. The reaction mixture was quenched by water and extracted with EtOAc (30 mL×3). The organic layer was dried over Na$_2$SO$_4$, filtered, and concentrated to give the crude product, The crude product was used directly in the next step.

Step 7. Synthesis of ethyl 7-(1-(1-(tert-butoxycarbonyl)piperidin-4-yl)ethyl)-6-chloropyrrolo[1,2-b]pyridazine-5-carboxylate

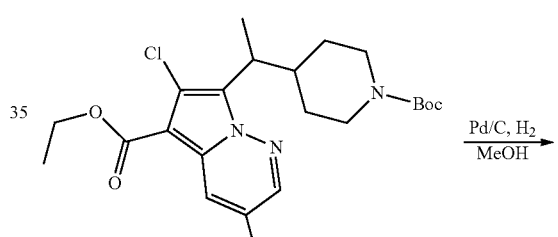

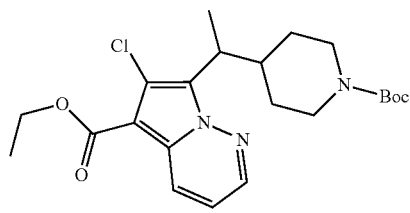

To a solution of compound ethyl 7-(1-(1-(tert-butoxycarbonyl)piperidin-4-yl)ethyl)-3,6-dichloropyrrolo[1,2-b]pyridazine-5-carboxylate (463.4 mg, 1.07 mmol) in anhydrous MeOH (20 ml) was added palladium on carbon (29.3 mg, 0.25 mmol, 10 wt % Pd). The reaction mixture was purged with H$_2$ (1 atm) and allowed to stirred at room temperature for 8 hours. Then the mixture was filtered and concentrated to give the crude product. The crude product was purified by column chromatograph on silica gel (eluted: petrol ether/acetic ester=25:1~5:1) to give ethyl 7-(1-(1-(tert-butoxycarbonyl)piperidin-4-yl)ethyl)-6-chloropyrrolo[1,2-b]pyridazine-5-carboxylate (100 mg, yield 24%) as a yellow oil.

Step 8: Synthesis of ethyl 6-chloro-7-(1-(piperidin-4-yl)ethyl)pyrrolo[1,2-b]pyridazine-5-carboxylate

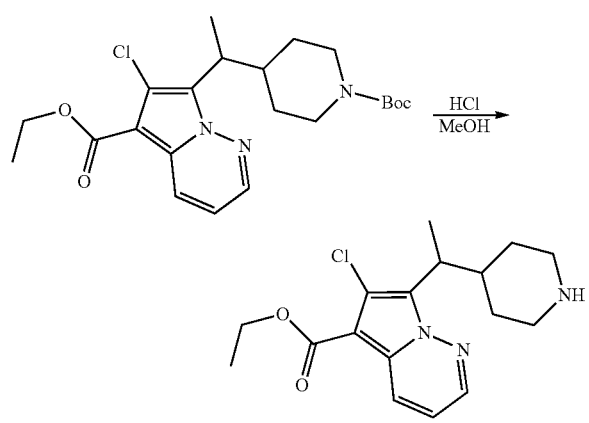

The compound of ethyl 7-(1-(1-(tert-butoxycarbonyl)piperidin-4-yl)ethyl)-6-chloropyrrolo[1,2-b]pyridazine-5-carboxylate (100 mg, 0.23 mmol) was dissolved in hydrogen chloride (10 ml) in MeOH, and the mixture was stirred at room temperature for 2 hours. Then the mixture was concentrated to give crude ethyl 6-chloro-7-(1-(piperidin-4-yl)ethyl)pyrrolo[1,2-b]pyridazine-5-carboxylate. It was used directly in the next step.

Step 9: Synthesis of ethyl 6-chloro-7-(1-(1-(2-hydroxy-2-methylpropyl)piperidin-4-yl)ethyl)pyrrolo[1,2-b]pyridazine-5-carboxylate

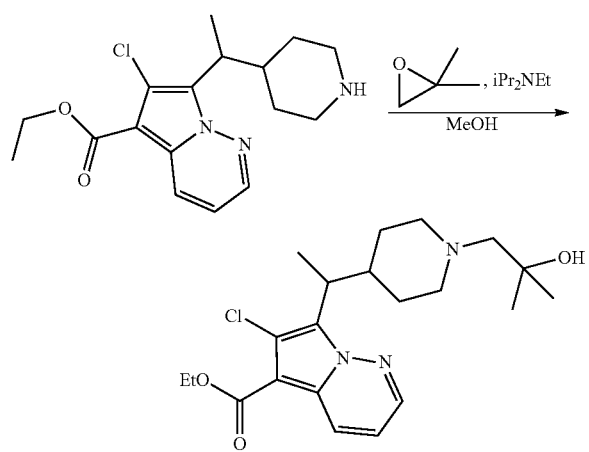

To a solution of crude compound ethyl 6-chloro-7-(1-(piperidin-4-yl)ethyl)pyrrolo[1,2-b]pyridazine-5-carboxylate (77 mg, 0.23 mmol) in anhydrous MeOH (3 ml) was added N-ethyl-N-isopropylpropan-2-amine (118.7 mg, 0.92 mmol) and 2,2-dimethyloxirane (66.34 mg, 0.92 mmol) at room temperature. The reaction mixture was stirred at 45° C. overnight. The reaction mixture was concentrated to give the crude ethyl 6-chloro-7-(1-(1-(2-hydroxy-2-methylpropyl)piperidin-4-yl)ethyl)pyrrolo[1,2-b]pyridazine-5-carboxylate. The crude product was used directly in the next step. LCMS (M+H$^+$) m/z 408.

Step 10: Synthesis of 6-chloro-7-(1-(1-(2-hydroxy-2-methylpropyl)piperidin-4-yl)ethyl)pyrrolo[1,2-b]pyridazine-5-carboxylic acid

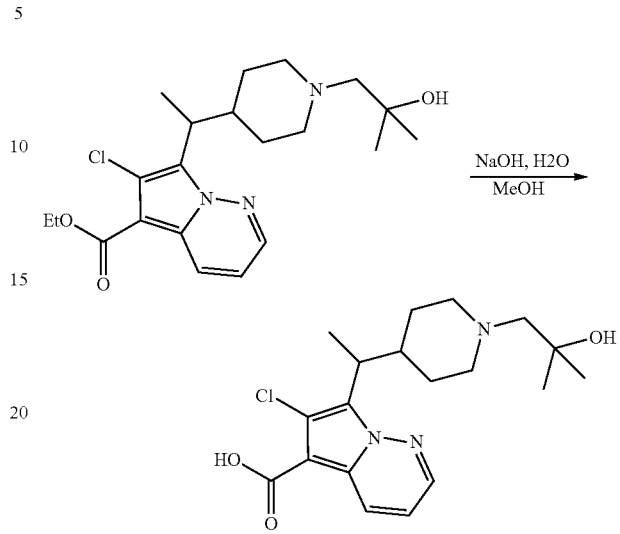

To a solution of crude compound ethyl 6-chloro-7-(1-(1-(2-hydroxy-2-methylpropyl)piperidin-4-yl)ethyl)pyrrolo[1,2-b]pyridazine-5-carboxylate (93.5 mg, 0.23 mmol) in MeOH (3.5 ml) and water (3.5 ml) was added sodium hydroxide (46 mg, 1.15 mmol) at room temperature. The reaction mixture was stirred at 70° C. for 3.5 hours. Then the reaction mixture was acidified to pH=3 with 2N hydrogen chloride and concentrated to give the crude 6-chloro-7-(1-(1-(2-hydroxy-2-methylpropyl)piperidin-4-yl)ethyl)pyrrolo[1,2-b]pyridazine-5-carboxylic acid. LCMS (M+H$^+$) m/z 380.

Step 11: Synthesis of 6-chloro-N-((4,6-dimethyl-2-oxo-1,2-dihydropyridin-3-yl)methyl)-7-(1-(1-(2-hydroxy-2-methylpropyl)piperidin-4-yl)ethyl)pyrrolo[1,2-b]pyridazine-5-carboxamid (Compound 141)

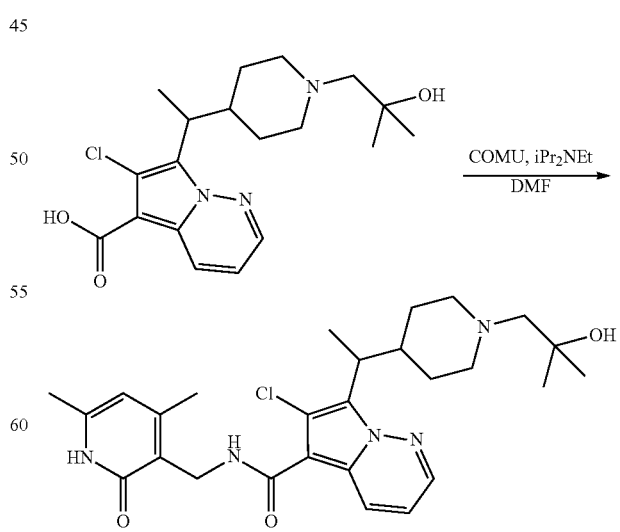

To a solution of crude compound 6-chloro-7-(1-(1-(2-hydroxy-2-methylpropyl)piperidin-4-yl)ethyl)pyrrolo[1,2- b]pyridazine-5-carboxylic acid (88.75 mg, 0.23 mmol) in anhydrous DMF (2.5 ml) were added 1-cyano-2-ethoxy-2-oxoethylidenaminooxy)dimethylamino-morpholino-carbenium hexafluorophosphate (395.6 mg, 0.92 mmol) and N-ethyl-N-isopropylpropan-2-amine (118.7 mg, 0.92 mmol) at room temperature. The reaction mixture was stirred at room temperature for 10 min. Then 3-(aminomethyl)-4,6-dimethylpyridin-2(1H)-one (44 mg, 0.23 mmol) was added at room temperature and the reaction mixture stirred at room temperature for overnight. The reaction was concentrated and the resulting crude product was purified by preparative HPLC (Mobile phase A: water with 0.05% ammonia solution; Mobile phase B: MeCN; column temperature: 30° C., Gradient: 50-80% B 10 min) to give 6-chloro-N-((4,6-dimethyl-2-oxo-1,2-dihydropyridin-3-yl)methyl)-7-(1-(1-(2-hydroxy-2-methylpropyl)piperidin-4-yl)ethyl)pyrrolo[1,2-b]pyridazine-5-carboxamide (31.1 mg, 26% yield). LCMS (M+H⁺) m/z 514. ¹H NMR (400 MHz, CHLOROFORM-d) δ 12.15 (s., 1 H), 8.74 (dd, J=9.03, 1.51 Hz, 1H), 8.11 (dd, J=4.52, 1.51 Hz, 1 H), 7.96 (t, J=5.52 Hz, 1 H), 6.73 (dd, J=9.29, 4.27 Hz, 1 H), 5.94 (s, 1 H), 4.59 (d, J=5.52 Hz, 2 H), 3.32 (s., 1 H), 3.01 (s., 1 H), 2.76 (s., 1 H), 2.41 (s, 4 H), 2.30 (s, 5 H), 2.18 (s., 1 H), 2.11-2.04(m, 1 H), 1.98 (d, J=13.05 Hz, 2 H), 1.40 (d, J=7.03 Hz, 4 H), 1.26 (s, 1 H), 1.12 (s, 3 H), 1.15 (s, 3 H), 1.01 (d, J=12.55 Hz, 1 H)

Compound 142 was synthesized in a similar manner to Compound 141 using the appropriate starting materials and modifications:

| Compound No. | Name | 1H NMR | LCMS |
|---|---|---|---|
| 142 | 6-chloro-7-(1-(1-(2-hydroxy-2-methylpropyl)piperidin-4-yl)ethyl)-N-((4-methoxy-6-methyl-2-oxo-1,2-dihydropyridin-3-yl)methyl)pyrrolo[1,2-b]pyridazine-5-carboxamide | ¹H NMR (400 MHz, CHLOROFORM-d) δ 12.95 (s, 1 H), 8.82-8.74 (m, 1 H), 8.10 (dd, J = 4.52, 1.51 Hz, 1 H), 7.98 (t, J = 5.27 Hz, 1 H), 6.72 (dd, J = 9.03, 4.52 Hz, 1 H), 5.95 (s, 1 H), 4.63 (d, J = 5.52 Hz, 2 H), 3.90 (s, 3 H), 3.32 (s, 1 H), 3.09 (s, 1 H), 2.84 (s, 1 H), 2.44 (s., 1 H), 2.38 (s, 5 H), 2.28-2.20(m, 1 H), 2.12 (d, J = 9.03 Hz, 1 H), 2.00 (d, J = 12.05 Hz, 1 H), 1.40 (d, J = 7.53 Hz, 3 H), 1.25 (s., 2 H), 1.17 (s, 3 H), 1.14 (s, 3 H), 1.03 (d, J = 13.05 Hz, 1 H) | 530 |

Example 22

Synthesis of 7-tert-butyl 5-ethyl 6-methylpyrrolo[1,2-b]pyridazine-5,7-dicarboxylate (Compound 125)

Step 1: Synthesis of 7-tert-butyl 5-ethyl 6-methylpyrrolo[1,2-b]pyridazine-5,7-dicarboxylate

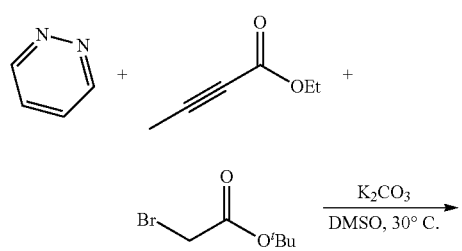

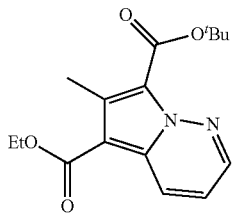

To a solution of pyridazine (2.0 g, 25.0 mmol) in dimethyl sulfoxide (100.0 mL) was added ethyl but-2-ynoate (2.8 g, 25.0 mmol), tert-butyl 2-bromoacetate (4.87 g, 25.0 mmol) and potassium carbonate (6.9 g, 50.0 mmol). The resulting solution was stirred at 30° C. under N₂ for 8 hours. The mixture was partitioned between ethyl acetate and water. The organic phase was removed and the aqueous layer was extracted with ethyl acetate. The combined organic layers were washed by brine, dried over anhydrous sodium sulfate, and concentrated in vacuo. The residue was purified by silica gel chromatography (petroleum ether:ethyl acetate=12:1) to afford 7-tert-butyl 5-ethyl 6-methylpyrrolo[1,2-b]pyridazine-5,7-dicarboxylate (620.0 mg, 8.2%) as a light yellow solid.

Step 2: Synthesis of 5-(ethoxycarbonyl)-6-methylpyrrolo[1,2-b]pyridazine-7-carboxylic acid

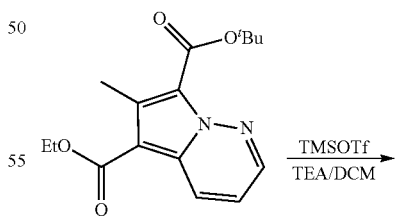

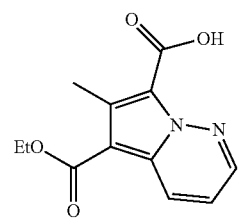

To a solution of 7-tert-butyl 5-ethyl 6-methylpyrrolo[1,2-b]pyridazine-5,7-dicarboxylate (300.0 mg, 0.99 mmol) in dichloromethane (18.5 mL) was added triethylamine (3.0 g, 29.7 mmol). To the reaction mixture was added trimethylsilyl trifluoromethanesulfonate (4.4 g, 19.8 mmol) in a dropwise manner. The resulting solution was stirred at room temperature under N₂ for 2 hours. The reaction was quenched by the addition of water and the mixture was concentrated in vacuo to afford the crude product which was in the next step without further purification.

Step 3: Synthesis of ethyl 6-methyl-7-(morpholine-4-carbonyl)pyrrolo[1,2-b]pyridazine-5-carboxylate (Intermediate 20A)

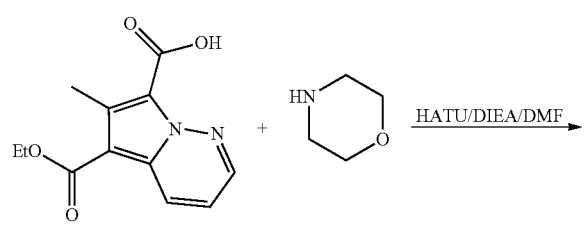

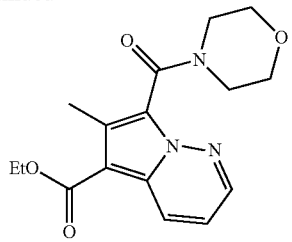

To a solution of 5-(ethoxycarbonyl)-6-methylpyrrolo[1,2-b]pyridazine-7-carboxylic acid (150.0 mg, 0.6 mmol) in N,N-dimethylformamide (3.0 mL) was added O-(7-azabenzotriazol-1-yl)-N,N,N,N,-tetramethyluronium (456.0 mg, 1.2 mmol), N,N-diisopropylethylamine (232.2 mg, 1.8 mmol) and morpholine (104.5 mg, 1.2 mmol). The resulting solution was stirred at 30° C. under N₂ overnight. The mixture was partitioned between ethyl acetate and water. The organic phase was removed and the aqueous layer was extracted with ethyl acetate. The aqueous layer was extracted with ethyl acetate. The combined organic layers were washed with brine, dried over anhydrous sodium sulfate, and concentrated in vacuo. The residue was purified by silica gel pad (dichloromethane:methanol=30:1) to afford ethyl 6-methyl-7-(morpholine-4-carbonyl)pyrrolo[1,2-b]pyridazine-5-carboxylate (120.0 mg, 62.6%) as a yellow oil.

The intermediate shown in the following table was prepared according to the procedure described above using the appropriate starting materials and modifications:

| Intermediate | Structure | Name | LCMS |
|---|---|---|---|
| 20B | 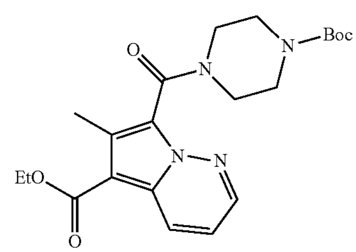 [SMILES: CCOC(=O)c1c(C)c(C(=O)N2CCN(C(=O)OC(C)(C)C)CC2)n2ncccc12] | Ethyl 7-(4-(tert-butoxycarbonyl)piperazine-1-carbonyl)-6-methylpyrrolo[1,2-b]pyridazine-5-carboxylate | ND |
| 20C | 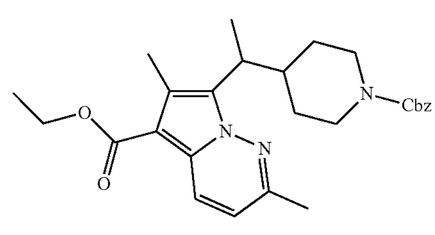 [SMILES: CCOC(=O)c1c(C)c(C(C)C2CCN(C(=O)OCc3ccccc3)CC2)n2nc(C)ccc12] | Ethyl 7-(1-(1-((benzyloxy)carbonyl)piperidin-4-yl)ethyl)-2,6-dimethylpyrrolo[1,2-b]pyridazine-5-carboxylate | ND |
| 20D | 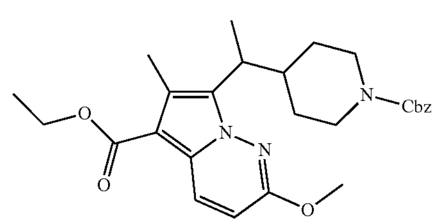 [SMILES: CCOC(=O)c1c(C)c(C(C)C2CCN(C(=O)OCc3ccccc3)CC2)n2nc(OC)ccc12] | Ethyl 7-(1-(1-((benzyloxy)carbonyl)piperidin-4-yl)ethyl)-2-methoxy-6-methylpyrrolo[1,2-b]pyridazine-5-carboxylate | 457 |

Step 4: Synthesis of 6-methyl-7-(morpholine-4-carbonyl)pyrrolo[1,2-b]pyridazine-5-carboxylic acid (Intermediate 21A)

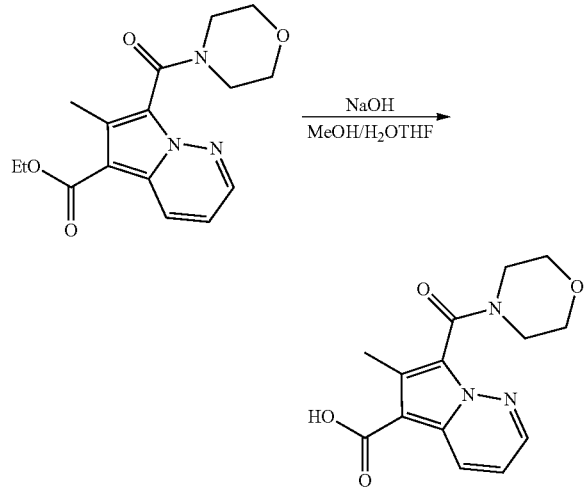

To a solution of ethyl 6-methyl-7-(morpholine-4-carbonyl)pyrrolo[1,2-b]pyridazine-5-carboxylate (120.0 mg, 0.38 mmol) in tetrahydrofuran/methanol/water (2.0 mL/2.0 mL/2.0 mL) was added sodium hydroxide (80.0 mg, 2.0 mmol). The reaction mixture was stirred at 50° C. overnight. To the resultant reaction mixture was added 1N hydrogen chloride until the reaction mixture was adjusted to pH 5-6. The mixture was subsequently concentrated in vacuo to afford 6-methyl-7-(morpholine-4-carbonyl)pyrrolo[1,2-b]pyridazine-5-carboxylic acid (96.0 mg, 87.7%) as yellow oil which was used for the next step directly.

Step 5: Synthesis of N-((4,6-dimethyl-2-oxo-1,2-dihydropyridin-3-yl)methyl)-6-methyl-7-(morpholine-4-carbonyl)pyrrolo[1,2-b]pyridazine-5-carboxamide (Compound 125)

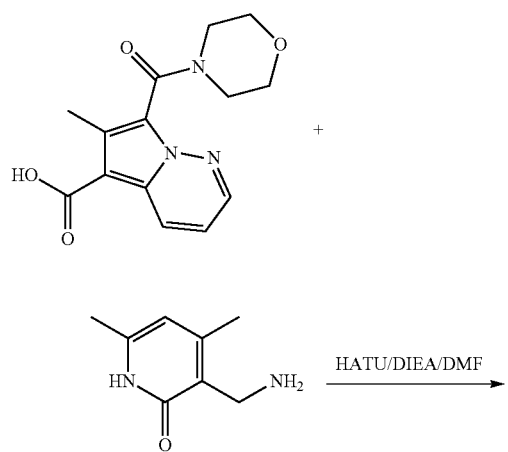

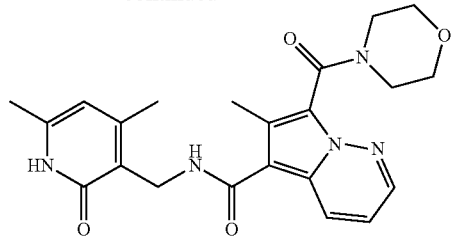

To a solution of 6-methyl-7-(morpholine-4-carbonyl)pyrrolo[1,2-b]pyridazine-5-carboxylic acid (96.0 mg, 0.33 mmol) in N,N-dimethylformamide (2.5 mL) was added O-(7-azabenzotriazol-1-yl)-N,N,N,N,-tetramethyluronium (250.8 mg, 0.66 mmol), N,N-diisopropylethylamine (127.7 mg, 0.99 mmol) and 3-(aminomethyl)-4,6-dimethylpyridin-2(1H)-one (150.7 mg, 0.99 mmol). The resulting solution was stirred at room temperature under $N_2$ overnight. The mixture was partitioned between ethyl acetate and water. The organic phase was removed and the aqueous layer was extracted with ethyl acetate. The combined organic layers were washed with brine, dried over anhydrous sodium sulfate, and concentrated in vacuo. The residue was subjected to preparatory HPLC for purification to afford N-((4,6-dimethyl-2-oxo-1,2-dihydropyridin-3-yl)methyl)-6-methyl-7-(morpholine-4-carbonyl)pyrrolo[1,2-b]pyridazine-5-carboxamide (17.0 mg, 12.1%) as a light yellow solid. LCMS (M+H$^+$) m/z: calcd. 423.47. found 423.9. $^1$H NMR (400 MHz, DMSO-d$_6$) δ 11.54 (br.s, 1H), 8.34-8.26 (m, 2H), 7.91-7.83 (m, 1H), 6.96-6.89 (m, 1H), 5.89 (s, 1H), 4.34-4.26 (m, 2H), 3.81-3.49 (m, 6H), 3.16-3.04 (m, 2H), 2.36 (s, 3H), 2.25 (s, 3H), 2.11 (s, 3H).

Example 23

Synthesis of N-((4,6-dimethyl-2-oxo-1,2-dihydropyridin-3-yl)methyl)-6-methyl-7-(4-(methylsulfonyl)piperazine-1-carbonyl)pyrrolo[1,2-b]pyridazine-5-carboxamide (Compound 126)

Step 1: Synthesis of ethyl 6-methyl-7-(piperazine-1-carbonyl)pyrrolo[1,2-b]pyridazine-5-carboxylate

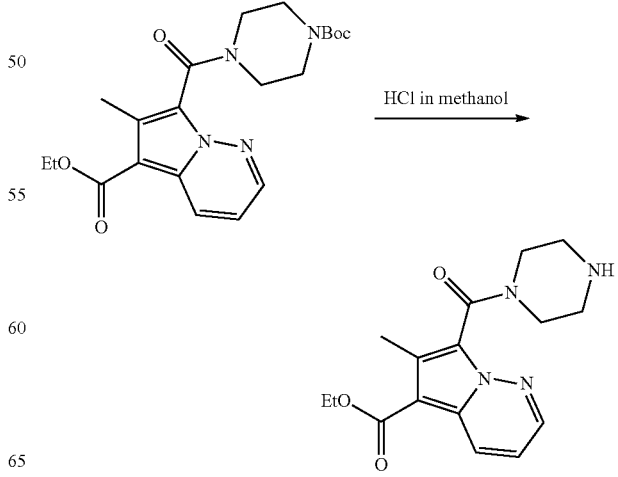

To a solution of ethyl 7-(4-(tert-butoxycarbonyl)piperazine-1-carbonyl)-6-methylpyrrolo[1,2-b]pyridazine-5-carboxylate (20B; 394.0 mg, 0.94 mmol) in HCl in methanol (4.0 mL) was stirred at room temperature under $N_2$ for 2 hours. The reaction mixture was concentrated in vacuo to afford the crude product which was used for the next step directly.

Step 2: Synthesis of ethyl 6-methyl-7-(4-(methylsulfonyl)piperazine-1-carbonyl)pyrrolo[1,2-b]pyridazine-5-carboxylate

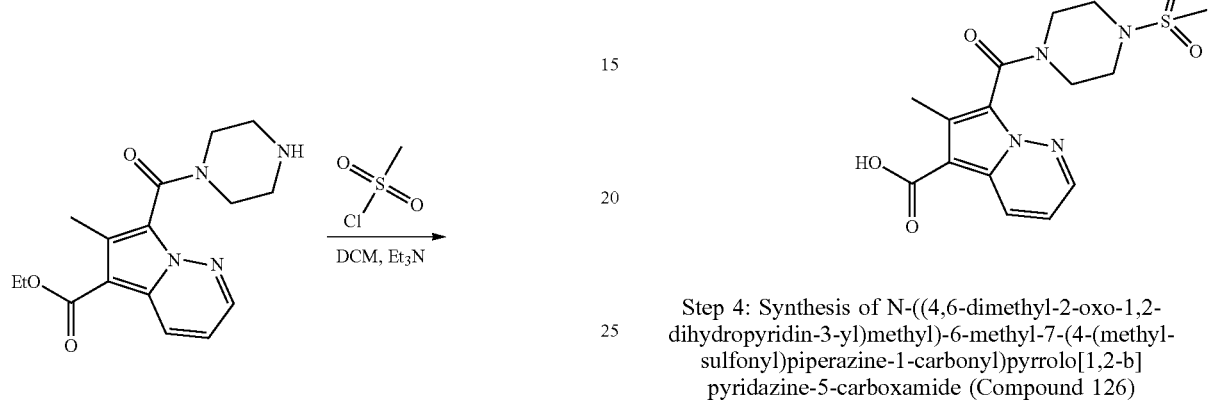

To a cooled (0° C.) solution of ethyl 6-methyl-7-(piperazine-1-carbonyl)pyrrolo[1,2-b]pyridazine-5-carboxylate (299.5 mg, 0.95 mmol) in dichloromethane (5.0 mL) was added triethylamine (479.8 mg, 4.75 mmol), followed by the addition of methanesulfonyl chloride (130.4 mg, 1.14 mmol). The resulting solution was stirred at room temperature under $N_2$ overnight. The mixture was poured into ice water and extracted with ethyl acetate. The aqueous phase was further extracted with ethyl acetate. The combined organic layers were washed by brine, dried over anhydrous sodium sulfate, and concentrated in vacuo to afford ethyl 6-methyl-7-(4-(methylsulfonyl)piperazine-1-carbonyl)pyrrolo[1,2-b]pyridazine-5-carboxylate (277.8 mg, 100%) as yellow oil which was used for the next step without further purification.

Step 3: Synthesis of 6-Methyl-7-(4-(methylsulfonyl)piperazine-1-carbonyl)pyrrolo[1,2-b]pyridazine-5-carboxylic acid Ethyl 6-methyl-7-(4-(methylsulfonyl)piperazine-1-carbonyl)pyrrolo[1,2-b]pyridazine-5-carboxylate was converted to 6-methyl-7-(4-(methylsulfonyl)piperazine-1-carbonyl)pyrrolo[1,2-b]pyridazine-5-carboxylic acid as described in Step 4 of the previous Example.

Step 4: Synthesis of N-((4,6-dimethyl-2-oxo-1,2-dihydropyridin-3-yl)methyl)-6-methyl-7-(4-(methylsulfonyl)piperazine-1-carbonyl)pyrrolo[1,2-b]pyridazine-5-carboxamide (Compound 126)

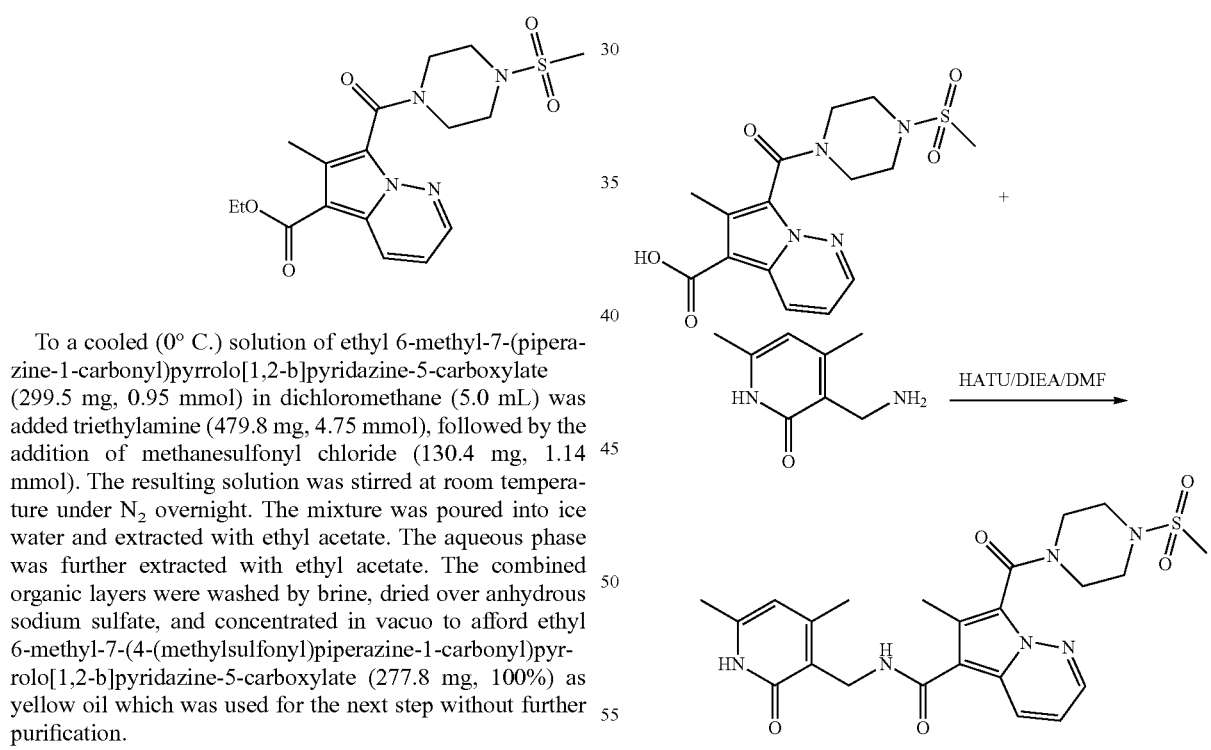

6-methyl-7-(4-(methylsulfonyl)piperazine-1-carbonyl)pyrrolo[1,2-b]pyridazine-5-carboxylic acid was combined with 3-(aminomethyl)-4,6-dimethylpyridin-2(1H)-one to produce Compound 126 as described in Step 5 in the previous Example. LCMS (M+H$^+$) m/z: 501. $^1$H NMR (400 MHz, DMSO-d$_6$) δ 11.60 (s, 1H), 8.45-8.18 (m, 2H), 7.95-7.81 (m, 1H), 7.04-6.88 (m, 1H), 5.89 (s, 1H), 4.37-4.23 (m, 2H), 3.95-3.64 (m, 2H), 3.27-3.16 (m, 4H), 3.14-2.97 (m, 2H), 2.93 (s, 3H), 2.37 (s, 3H), 2.25 (s, 3H), 2.12 (s, 3H).

Example 24

Synthesis of ethyl 2,6-dimethyl-7-(1-(piperidin-4-yl)ethyl)pyrrolo[1,2-b]pyridazine-5-carboxylate (Compound 129)

Step 1: Synthesis of ethyl 2,6-dimethyl-7-(1-(piperidin-4-yl)ethyl)pyrrolo[1,2-b]pyridazine-5-carboxylate (Intermediate 21A)

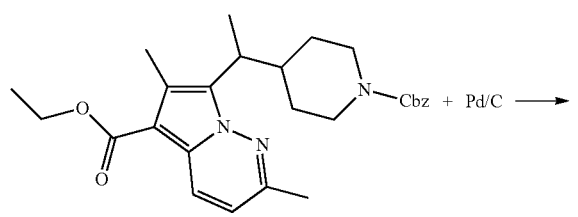

A mixture of compound ethyl 7-(1-(1-(((benzyloxy)carbonyl)piperidin-4-yl)ethyl)-2,6-dimethylpyrrolo[1,2-b]pyridazine-5-carboxylate (20C; 220 mg, 0.48 mmol) and Pd/C (40 mg) in methanol (5 mL) was stirred under hydrogen (15 psi) at room temperature for 2 hours. The reaction mixture was filtered and the filtrate was concentrated to give crude product. The crude product was purified by preparatory TLC (dichloromethane:methanol=10:1) to give ethyl 2,6-dimethyl-7-(1-(piperidin-4-yl)ethyl)pyrrolo[1,2-b]pyridazine-5-carboxylate (110 mg, 69.6% yield). LCMS (M+H$^+$) m/z: calcd 329.1. found 330.1.

The intermediate shown in the following table was prepared according to the procedure described above using 20D as the starting material:

Step 2: Synthesis of ethyl 7-(1-(1-(2-hydroxy-2-methylpropyl)piperidin-4-yl)ethyl)-2,6-dimethylpyrrolo[1,2-b]pyridazine-5-carboxylate (Intermediate 22A)

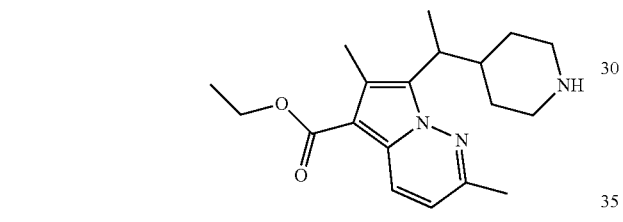

To a solution of ethyl 2,6-dimethyl-7-(1-(piperidin-4-yl)ethyl)pyrrolo[1,2-b]pyridazine-5-carboxylate (50 mg, 0.15 mmol) in methanol (2 mL) was added 2,2-dimethyloxirane (32 mg, 0.45 mmol) and N-ethyl-N-isopropylpropan-2-amine (116 mg, 0.9 mmol). The reaction mixture was stirred at 40° C. overnight. The reaction was completed and concentrated to give crude product ethyl 7-(1-(1-(2-hydroxy-2-methylpropyl)piperidin-4-yl)ethyl)-2,6-dimethylpyrrolo[1,2-b]pyridazine-5-carboxylate (30 mg, 50% yield). LCMS (M+H$^+$) m/z: calcd 401.1; found 401.9.

The intermediate shown in the following table was prepared according to the procedure described above using the appropriate starting material:

| Intermediate | Structure | Name | LCMS |
|---|---|---|---|
| 21B | 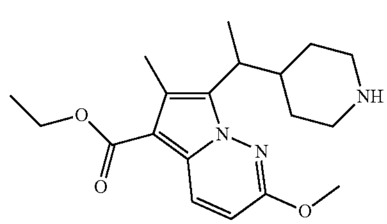 [SMILES: CCOC(=O)c1c(C)c(C(C)C2CCNCC2)n2nc(OC)ccc12] | Ethyl 2-methoxy-6-methyl-7-(1-(piperidin-4-yl)ethyl)pyrrolo[1,2-b]pyridazine-5-carboxylate | 346 |

| Intermediate | Structure | Name | LCMS |
|---|---|---|---|
| 22B | 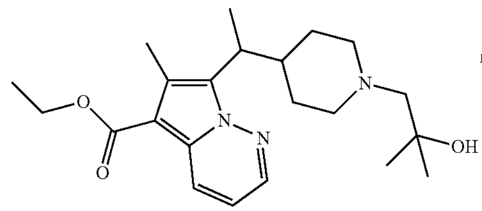 | Ethyl 7-(1-(1-(2-hydroxy-2-methylpropyl)piperidin-4-yl)ethyl)-6-methylpyrrolo[1,2-b]pyridazine-5-carboxylate | ND |

Step 3: Synthesis of 7-(1-(1-(2-hydroxy-2-methyl-propyl)piperidin-4-yl)ethyl)-6-methylpyrrolo[1,2-b]pyridazine-5-carboxylic acid (Intermediate 23A)

Step 4: Synthesis of N-((4,6-dimethyl-2-oxo-1,2-dihydropyridin-3-yl)methyl)-7-(1-(1-(2-hydroxy-2-methylpropyl)piperidin-4-yl)ethyl)-6-methylpyrrolo[1,2-b]pyridazine-5-carboxamide (Compound 129)

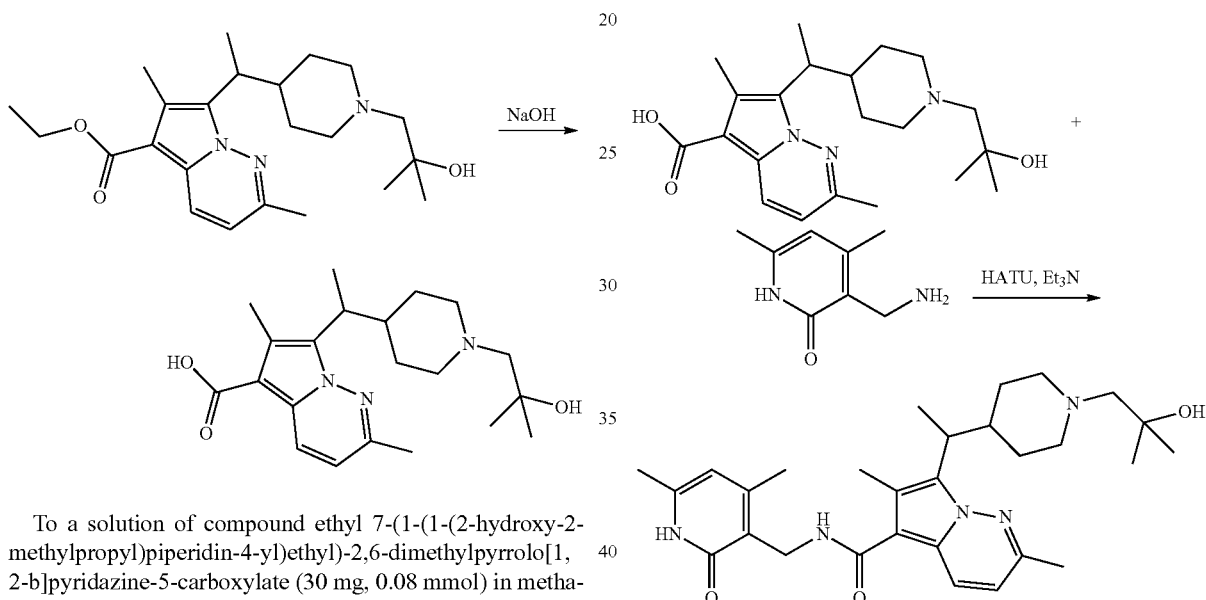

To a solution of compound ethyl 7-(1-(1-(2-hydroxy-2-methylpropyl)piperidin-4-yl)ethyl)-2,6-dimethylpyrrolo[1,2-b]pyridazine-5-carboxylate (30 mg, 0.08 mmol) in methanol (2 mL) and water (1 mL) was added sodium hydroxide (15 mg, 0.38 mmol). The reaction mixture was stirred at 70° C. overnight. The reaction mixture was neutralized with 2N hydrochloric acid and the resultant solution was concentrated to give the crude product 7-(1-(1-(2-hydroxy-2-methylpropyl)piperidin-4-yl)ethyl)-2,6-dimethylpyrrolo[1,2-b]pyridazine-5-carboxylic acid (15 mg, 53.4% yield) as a yellow solid. LCMS (M+H⁺) m/z: calcd 373.2; found 373.9.

The intermediate shown in the following table was prepared according to the procedure described above using the appropriate starting materials:

To a solution of compound 7-(1-(1-(2-hydroxy-2-methylpropyl)piperidin-4-yl)ethyl)-2,6-dimethylpyrrolo[1,2-b]pyridazine-5-carboxylic acid (15 mg, 0.04 mmol) and 3-(aminomethyl)-4,6-dimethylpyridin-2(1H)-one (8.5 mg, 0.06 mmol) in dichloromethane (3 mL) were added compound O-(7-Azabenzotriazol-1-yl)-N,N,N',N'-tramethyluronium hexafluorophosphate (28 mg, 0.07 mmol) and triethylamine (7.4 mg, 0.07 mmol). The reaction mixture was stirred at 50° C. for 3 hours. The crude product was purified by preparative HPLC (Mobile phase A: water with 0.05%

| Intermediate | Structure | Name | LCMS |
|---|---|---|---|
| 23B | | 7-(1-(1-(2-Hydroxy-2-methylpropyl)piperidin-4-yl)ethyl)-6-methylpyrrolo[1,2-b]pyridazine-5-carboxylic acid | 360 | ammonia solution; Mobile phase B: MeCN; column temperature: 30° C., Gradient: 30-60% B over 10 min) to give product N-((4,6-dimethyl-2-oxo-1,2-dihydropyridin-3-yl)methyl)-7-(1-(1-(2-hydroxy-2-methylpropyl)piperidin-4-yl)ethyl)-2,6-dimethylpyrrolo[1,2-b]pyridazine-5-carboxamide (12 mg, 63%) as a yellow solid. LCMS (M+H$^+$) calcd. 507.32. found 508.1. $^1$H NMR (400 MHz, CDCl$_3$) δ 0.96-1.07 (m, 1H), 1.31-1.32 (d, J=3.2 Hz, 6H), 1.34-1.36 (d, J=7.2 Hz, 4H), 1.94-2.20 (m, 3H), 2.23 (s, 6H), 2.40-2.43 (m, 8H), 2.49 (s, 1H), 2.78 (s, 1H), 2.93 (s, 2H), 4.54-4.56 (d, J=5.6 Hz, 2H), 5.94 (s, 1H), 6.58 (m, 1H), 7.20 (m, 1H), 8.26-8.28 (d, J=9.2 Hz, 1H).

The compound of the invention shown in the following table was prepared according to the procedure described above using the indicated starting materials and art-known modifications.

To a solution of ethyl 2-methoxy-6-methyl-7-(1-(piperidin-4-yl)ethyl)pyrrolo[1,2-b]pyridazine-5-carboxylate (21B; 210 mg, 0.61 mmol) in N,N-dimethylformamide (10 mL) were added 1-chloropropan-2-one (84 mg, 0.91 mmol) and potassium carbonate (252 mg, 1.83 mmol). The reaction mixture was stirred at 50° C. for 3 hours. The reaction was quenched by adding water (20 mL). The organic phase was removed and the aqueous phase was extracted with ethyl acetate (10 mL×3). The combined organic layers were concentrated to give crude product ethyl 2-methoxy-6-methyl-7-(1-(1-(2-oxopropyl)piperidin-4-yl)ethyl)pyrrolo[1,2-b]pyridazine-5-carboxylate (200 mg, 81.9% yield). LCMS (M+H$^+$) m/z: calcd 401.2 found 401.9.

| Compound | Name | $^1$H NMR | LCMS | Intermediate Used |
|---|---|---|---|---|
| 128 | N-((4,6-dimethyl-2-oxo-1,2-dihydropyridin-3-yl)methyl)-7-(1-(1-(2-hydroxy-2-methylpropyl)piperidin-4-yl)ethyl)-6-methylpyrrolo [1,2-b]pyridazine-5-carboxamide | $^1$H NMR (400 MHz, CDCl$_3$) δ 0.97-0.94 (d, J = 12 Hz, 7H), 1.13-1.10 (d, J = 12 Hz, 4H), 2.08 (m, 3H), 2.24 (s, 6H), 2.42 (s, 3H), 2.48 (s, 3H), 2.69 (s, 1H), 3.03 (m, 3H), 4.58-4.56 (d, J = 8 Hz, 2H), 5.94 (s, 1H), 6.58 (m, 1H), 7.22 (m, 1H), 8.02-8.01 (d, J = 4 Hz, 1H), 8.42-40 (d, J = 8 Hz, 1H). | 494 | 23B |

Example 25

Synthesis of N-((4,6-dimethyl-2-oxo-1,2-dihydropyridin-3-yl)methyl)-7-(1-(1-(2-hydroxy-2-methylpropyl)piperidin-4-yl)ethyl)-2-methoxy-6-methylpyrrolo[1,2-b]pyridazine-5-carboxamide (Compound 127)

Step 1: Synthesis of ethyl 2-methoxy-6-methyl-7-(1-(1-(2-oxopropyl)piperidin-4-yl)ethyl)pyrrolo[1,2-b]pyridazine-5-carboxylate

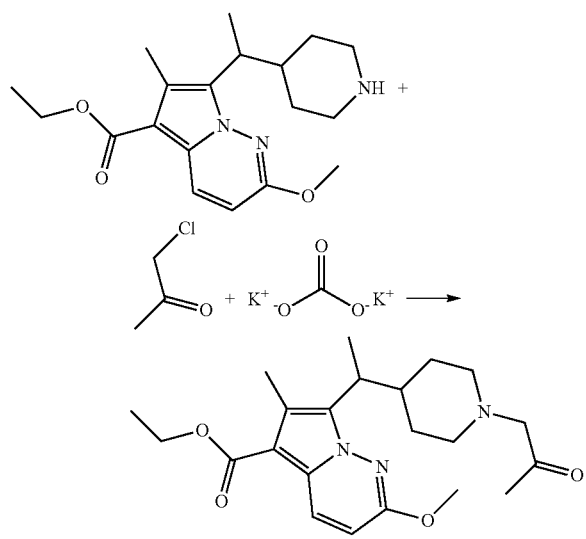

Step 2: Synthesis of ethyl 7-(1-(1-(2-hydroxy-2-methylpropyl)piperidin-4-yl)ethyl)-2-methoxy-6-methylpyrrolo[1,2-b]pyridazine-5-carboxylate

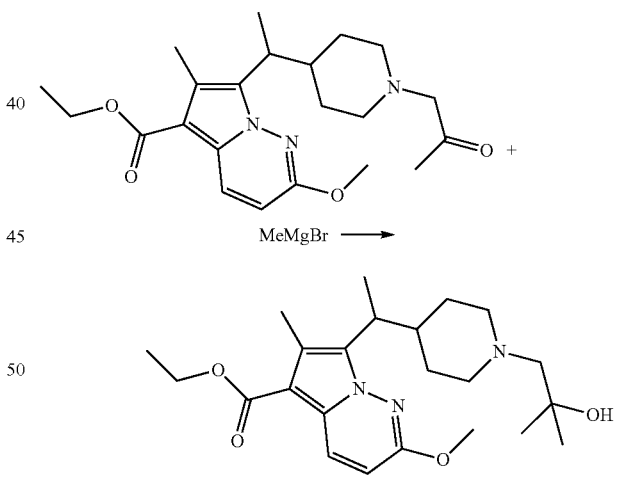

To a cooled (−78° C.) solution of ethyl 2-methoxy-6-methyl-7-(1-(1-(2-oxopropyl)piperidin-4-yl)ethyl)pyrrolo[1,2-b]pyridazine-5-carboxylate (200 mg, 0.50 mmol) in tetrahydrofuran (5 mL) was added methylmagnesium bromide solution (0.85 mL, 3 M). The resultant mixture was stirred at −30° C. for 3 h. The reaction was subsequently quenched with saturated aqueous ammonium chloride (100 mL). The organic phase was removed and aqueous phase was extracted with ethyl acetate (10 mL×3). The combined organic layers were dried over sodium sulfate and concentrated to give the crude product ethyl 7-(1-(1-(2-hydroxy- 2-methylpropyl)piperidin-4-yl)ethyl)-2-methoxy-6-methyl-pyrrolo[1,2-b]pyridazine-5-carboxylate (200 mg, 96.1% yield) as a yellow oil.

Step 3: Synthesis of 7-(1-(1-(2-Hydroxy-2-methylpropyl)piperidin-4-yl)ethyl)-2-methoxy-6-methyl-pyrrolo[1,2-b]pyridazine-5-carboxylic acid

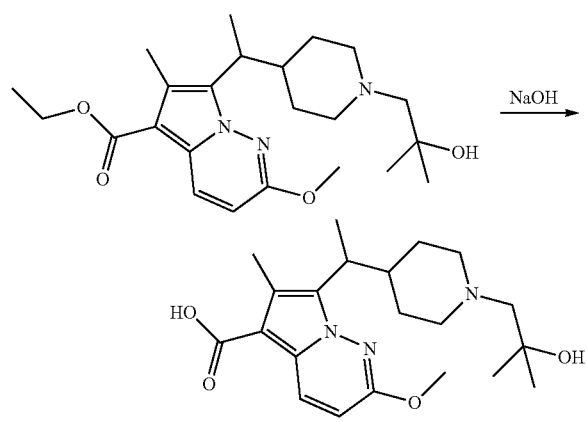

The conversion of ethyl 7-(1-(1-(2-hydroxy-2-methylpropyl)piperidin-4-yl)ethyl)-2-methoxy-6-methylpyrrolo[1,2-b]pyridazine-5-carboxylate to 7-(1-(1-(2-Hydroxy-2-methylpropyl)piperidin-4-yl)ethyl)-2-methoxy-6-methylpyrrolo[1,2-b]pyridazine-5-carboxylic acid was achieved as described in Step 3 of the previous Example.

Step 4: Synthesis of N-((4,6-dimethyl-2-oxo-1,2-dihydropyridin-3-yl)methyl)-7-(1-(1-(2-hydroxy-2-methylpropyl)piperidin-4-yl)ethyl)-2-methoxy-6-methylpyrrolo[1,2-b]pyridazine-5-carboxamide (Compound 127)

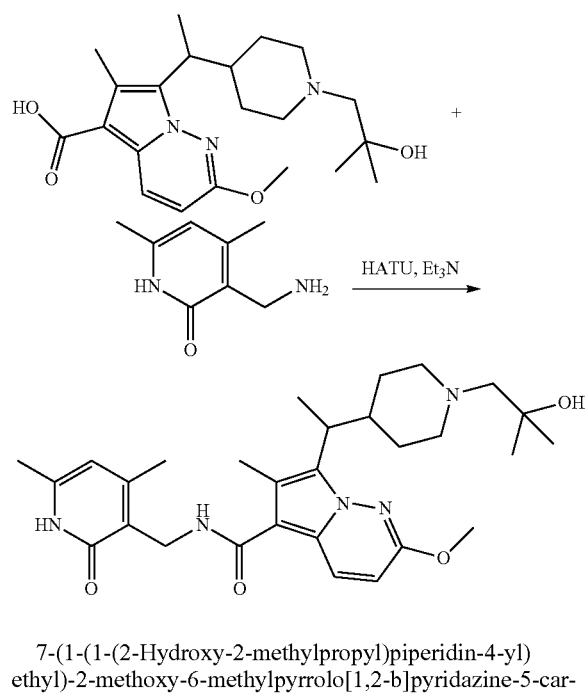

7-(1-(1-(2-Hydroxy-2-methylpropyl)piperidin-4-yl)ethyl)-2-methoxy-6-methylpyrrolo[1,2-b]pyridazine-5-car-boxylic acid was combined with 3-(aminomethyl)-4,6-dimethylpyridin-2(1H)-one to produce Compound 127 as described in Step 4 in the previous Example. LCMS (M+H⁺) m/z: 524. ¹H NMR (400 MHz, CDCl₃) δ 1.11-1.08 (d, J=12 Hz, 6H), 1.34 (m, 4H), 1.96 (m, 3H), 2.11-2.08 (d, J=12 Hz, 6H), 2.26 (m, 6H), 2.40 (m, 1H), 2.97-2.92 (d, J=20 Hz, 4H), 3.34 (s, 1H), 3.90 (s, 3H), 4.54-4.53 (d, J=4 Hz, 2H), 5.91 (s, 1H), 6.29-6.27 (d, J=8 Hz, 1H), 7.16 (m, 1H), 8.30-8.27 (d, J=12 Hz, 1H).

Example 26

Synthesis of 7-(1-(dimethylamino)ethyl)-N-((4-methoxy-6-methyl-2-oxo-1,2-dihydropyridin-3-yl)methyl)-6-methylpyrrolo[1,2-b]pyridazine-5-carboxamide (Compound 130)

Step 1: Synthesis of Ethyl 7-(1-(dimethylamino)ethyl)-6-methylpyrrolo[1,2-b]pyridazine-5-carboxylate The intermediates shown in the following table were prepared using intermediate 4G and the appropriate amine according to the procedure described in Step 1 of Example 9.

| Intermediate | Structure | Name | LCMS |
|---|---|---|---|
| 24A | 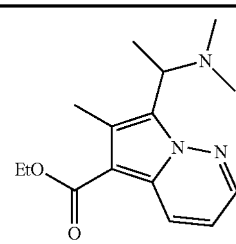 | Ethyl 7-(1-(dimethylamino)ethyl)-6-methylpyrrolo[1,2-b]pyridazine-5-carboxylate | 276 |
| 24B | 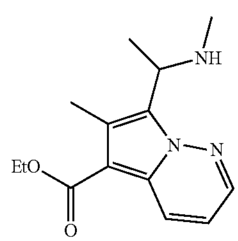 [SMILES: CCOC(=O)c1c(C)c(C(C)NC)n2ncccc12] | Ethyl 7-(1-(ethyl(methyl)amino)ethyl)-6-methylpyrrolo[1,2-b]pyridazine-5-carboxylate | ND |

Step 1A: Synthesis of ethyl 7-(1-(ethyl(methyl)amino)ethyl)-6-methylpyrrolo[1,2-b]pyridazine-5-carboxylate (Intermediate 25B)

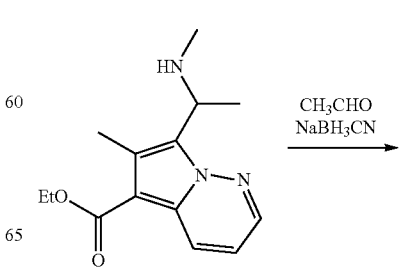

-continued

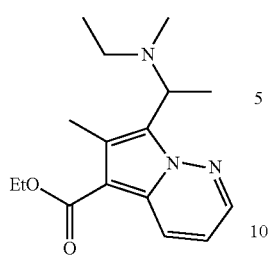

To a solution of ethyl-6-methyl-7-(1-(methylamino)ethyl) pyrrolo[1,2-b]pyridazine-5-carboxylate (24B; 300 mg, 1.15 mmol) in acetic acid (5 mL) was sequentially added acetaldehyde (253 mg, 5.75 mmol) and sodium cyanoborohydride (214 mg, 3.45 mmol). The resultant reaction mixture was stirred at room temperature overnight. After 24 h, the reaction mixture was concentrated and purified on silica gel eluted with (dichloromethane/methanol 50:1→20:1) to give product ethyl 7-(1-(ethyl(methyl)amino)ethyl)-6-methylpyrrolo[1,2-b]pyridazine-5-carboxylate (150 mg, 45% yield) as a yellow oil. LCMS (M+H$^+$) m/z: calcd. 289.1, found 290.1.

Step 2: Synthesis of 7-(1-(Dimethylamino)ethyl)-6-methylpyrrolo[1,2-b]pyridazine-5-carboxylic acid (Intermediate 26A)

The intermediates shown in the following table were prepared according to the dealkylation procedure described in Example 12 using the appropriate starting materials and modifications.

| Intermediate | Structure | Name | Starting Material |
|---|---|---|---|
| 26A | 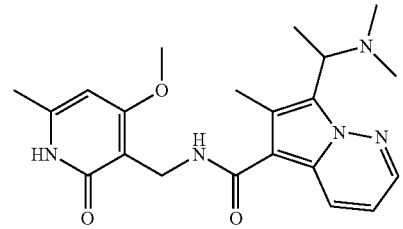 | 7-(1-(Dimethylamino)ethyl)-6-methylpyrrolo[1,2-b]pyridazine-5-carboxylic acid | 24A |
| 26B | 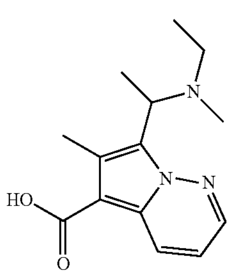 [SMILES: CCN(C)C(C)c1c(C)c(C(=O)O)c2cccnn12] | 7-(1-(Ethyl(methyl)amino)ethyl)-6-methylpyrrolo[1,2-b]pyridazine-5-carboxylic acid | 25B |

Step 3: Synthesis of 7-(1-(dimethylamino)ethyl)-N-((4-methoxy-6-methyl-2-oxo-1,2-dihydropyridin-3-yl)methyl)-6-methylpyrrolo[1,2-b]pyridazine-5-carboxamide (Compound 130)

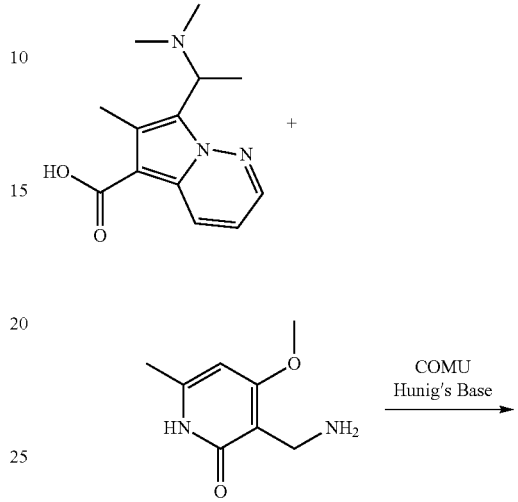

To a solution of 7-(1-(dimethylamino)ethyl)-6-methylpyrrolo[1,2-b]pyridazine-5-carboxylic acid (26A; 40 mg, 0.16 mmol) in N,N-dimethylformamide (2 mL) were added 3-(aminomethyl)-4-methoxy-6-methylpyridin-2(1H)-one (40.8 mg, 0.24 mmol), N-ethyl-N-isopropylpropan-2-amine (62.6 mg, 0.48 mmol), and (1-Cyano-2-ethoxy-2-oxoethylidenaminooxy)dimethylamino-morpholino-carbenium hexafluorophosphate (102.7 mg, 0.24 mmol). The mixture was stirred at room temperature overnight. The reaction mixture was concentrated and purified by preparative HPLC to give product 7-(1-(dimethylamino)ethyl)-N-((4-methoxy-6-methyl-2-oxo-1,2-dihydropyridin-3-yl)methyl)-6-methylpyrrolo[1,2-b]pyridazine-5-carboxamide (5.5 mg, 8.5%) as a yellow solid. LCMS (M+H$^+$) m/z: calcd. 397.21, found 398.2. $^1$H NMR (400 MHz, CDCl$_3$) δ 1.66-1.64 (d, J=8 Hz, 3H), 2.36 (m, 9H), 2.60 (s, 3H), 3.90 (s, 3H), 4.40 (s, 1H), 4.63-4.62 (d, J=12 Hz, 2H), 5.95 (s, 1H), 6.65 (m, 1H), 7.41 (s, 1H), 8.09 (m, 1H), 8.49 (m, 1H).

The compound of the invention shown in the following table was prepared according to the procedure described above using the indicated starting materials and art-known modifications.

| Compound | Name | ¹H NMR | LCMS | Starting Material |
|---|---|---|---|---|
| 131 | 7-(1-(ethyl(methyl)amino)ethyl)-N-((4-methoxy-6-methyl-2-oxo-1,2-dihydropyridin-3-yl)methyl)-6-methylpyrrolo[1,2-b]pyridazine-5-carboxamide | ¹H NMR (400 MHz, CDCl₃) δ 0.98 (m, 3H), 1.53 (m, 3H), 2.3 (s, 6H), 2.48 (m, 2H), 2.63 (s, 3H), 3.91 (s, 3H), 4.42-4.40 (d, J = 8 Hz, 1H), 4.65-4.64 (d, J = 4 Hz, 1H), 5.95 (s, 1H), 6.60 (m, 1H), 7.39 (s, 1H), 8.08-8.07 (d, J = 4 Hz, 1H), 8.50-8.48 (d, J = 8 Hz, 1H). | 353 | 26B |

Example 27

Synthesis of 6-chloro-N-((4-methoxy-6-methyl-2-oxo-1,2-dihydropyridin-3-yl)methyl)-7-(1-(tetrahydro-2H-pyran-4-yl)ethyl)pyrrolo[1,2-b]pyridazine-5-carboxamide (Compound 132)

Steps 1-3: Synthesis of ethyl 7-(1-(tetrahydro-2H-pyran-4-yl)ethyl)pyrrolo[1,2-b]pyridazine-5-carboxylate 2-bromo-1-(tetrahydro-2H-pyran-4-yl)ethanone (from Example 3, step 2) was combined with methyl but-2-ynoate (3) and pyridazine (2) as described in Example 4 to produce ethyl 7-(tetrahydro-2H-pyran-4-carbonyl)pyrrolo[1,2-b]pyridazine-5-carboxylate. That intermediate was treated with methylmagnesium bromide in THF as described in Example 8, step 1 to produce ethyl 7-(1-hydroxy-1-(tetrahydro-2H-pyran-4-yl)ethyl)pyrrolo[1,2-b]pyridazine-5-carboxylate. The hydroxyl intermediate was then treated with Et₃SiH dissolved in THF, followed by TFA, as described in Example 8, step 2 to produce ethyl 7-(1-(tetrahydro-2H-pyran-4-yl)ethyl)pyrrolo[1,2-b]pyridazine-5-carboxylate.

Step 4: Synthesis of ethyl 3,6-dichloro-7-(1-(tetrahydro-2H-pyran-4-yl)ethyl)pyrrolo[1,2-b]pyridazine-5-carboxylate

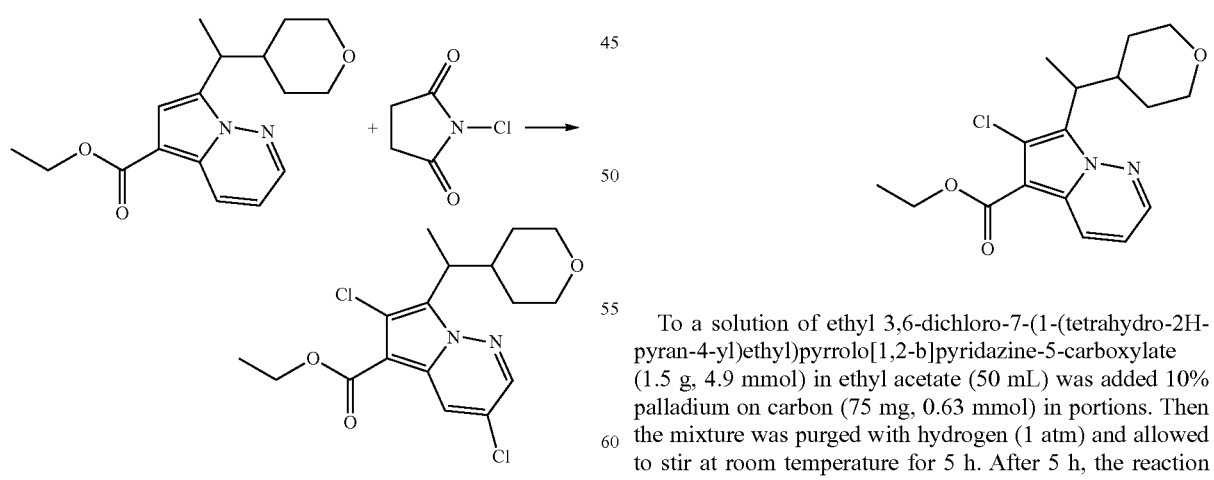

To a cooled (−30° C.) solution of ethyl 7-(1-(tetrahydro-2H-pyran-4-yl)ethyl)pyrrolo[1,2-b]pyridazine-5-carboxylate (2.5 g, 8.25 mmol) in anhydrous N,N-dimethylformamide (50 mL) was added 1-chloropyrrolidine-2,5-dione (2.2 g, 16.5 mmol) in portions. The resulting mixture was allowed to stir at room temperature for 6 h. The reaction mixture was quenched with water (200 mL), and then extracted with ethyl acetate (200 mL×3). The combined organic phases were dried by anhydrous sodium sulphate, and concentrated in vacuo. The resultant oil was purified by column chromatograph on silica gel (eluted with petroleum ether/ethyl ester 10:1 to 5:1) to give ethyl 3,6-dichloro-7-(1-(tetrahydro-2H-pyran-4-yl)ethyl)pyrrolo[1,2-b]pyridazine-5-carboxylate (2.3 g, 75% yield) as a yellow oil. LCMS (M+H⁺) m/z: calcd. 371.05, found 371.9.

Step 5: Synthesis of ethyl 6-chloro-7-(1-(tetrahydro-2H-pyran-4-yl)ethyl)pyrrolo[1,2-b]pyridazine-5-carboxylate To a solution of ethyl 3,6-dichloro-7-(1-(tetrahydro-2H-pyran-4-yl)ethyl)pyrrolo[1,2-b]pyridazine-5-carboxylate (1.5 g, 4.9 mmol) in ethyl acetate (50 mL) was added 10% palladium on carbon (75 mg, 0.63 mmol) in portions. Then the mixture was purged with hydrogen (1 atm) and allowed to stir at room temperature for 5 h. After 5 h, the reaction mixture was filtered. The filtrate was concentrated and purified by column chromatograph on silica gel (eluted with petroleum ether/ethyl acetate 10:1 to 5:1) to give ethyl 6-chloro-7-(1-(tetrahydro-2H-pyran-4-yl)ethyl)pyrrolo[1,2-b]pyridazine-5-carboxylate (1.3 g, 96% yield) as a yellow solid. LCMS (M+H⁺) m/z: calcd. 336.35, found 336.9.

Step 6: Synthesis of 6-chloro-7-(1-(tetrahydro-2H-pyran-4-yl)ethyl)pyrrolo[1,2-b]pyridazine-5-carboxylic acid

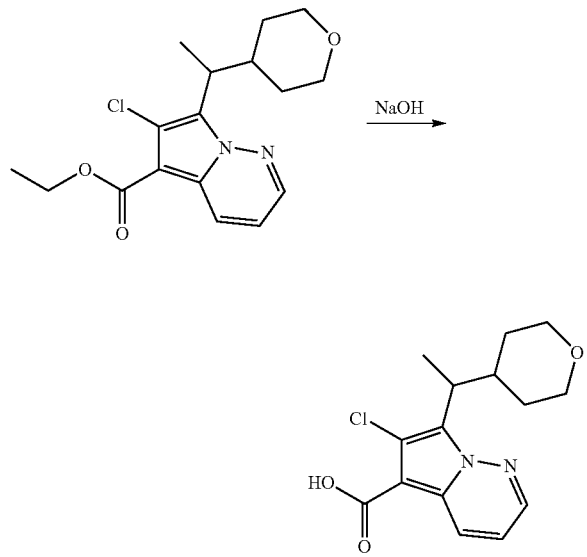 [SMILES: CCOC(=O)c1c(Cl)c(C(C)C2CCOCC2)n2ncccc12 ; "NaOH" ; CC(c1c(Cl)c(C(=O)O)c2cccnn12)C1CCOCC1]

To a solution of ethyl 6-chloro-7-(1-(tetrahydro-2H-pyran-4-yl)ethyl)pyrrolo[1,2-b]pyridazine-5-carboxylate (1.3 g, 3.86 mmol) in tetrahydrofuran/methanol (1:1, 40 mL) was added a solution of sodium hydroxide (772 mg, 19.3 mmol) dissolved in 20 mL water. The resulting reaction system was heated to 70° C. and allowed to stir for 5 h. After 5 h, the reaction mixture was cooled to 0° C. and 4N hydrogen chloride was added until the reaction solution turned slightly acidic (pH 6). Solvent and water was removed under reduced pressure to give 6-chloro-7-(1-(tetrahydro-2H-pyran-4-yl)ethyl)pyrrolo[1,2-b]pyridazine-5-carboxylic acid (1.19 g, assume quantitative yield) as a yellow solid, and it was used directly in the next step. LCMS (M+H+) m/z: calcd. 308.08, found 308.9.

Step 7: Synthesis of 6-chloro-N-((4-methoxy-6-methyl-2-oxo-1,2-dihydropyridin-3-yl)methyl)-7-(1-(tetrahydro-2H-pyran-4-yl)ethyl)pyrrolo[1,2-b]pyridazine-5-carboxamide (Compound 132)

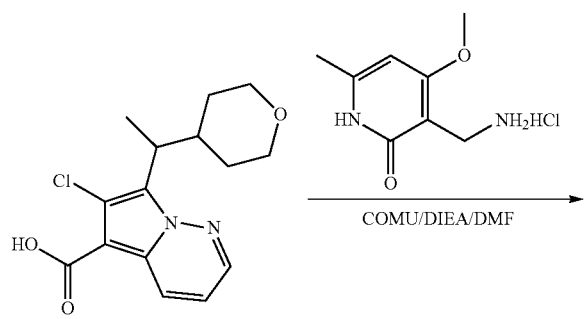

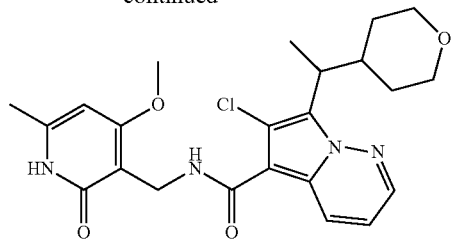

To a solution of 6-chloro-7-(1-(tetrahydro-2H-pyran-4-yl)ethyl)pyrrolo[1,2-b]pyridazine-5-carboxylic acid (1.19 g, crude) in anhydrous N,N-dimethylformamide (20 mL) was added 1-cyano-2-ethoxy-2-oxoethylidenaminooxy)dimethylamino-morpholino-carbenium hexafluorophosphate (2.48 g, 5.79 mmol) and N-ethyl-N-isopropylpropan-2-amine (996 mg, 7.72 mmol). The mixture was allowed to stirred for 30 mins at 0° C., followed by addition of 3-(aminomethyl)-4-methoxy-6-methylpyridin-2(1H)-one hydrochloride (1.18 g, 5.79 mmol). The resultant reaction mixture was allowed to stir for 12 hours at room temperature. The reaction mixture was partitioned between water (50 mL) and dichloromethane. The organic phase was removed and the aqueous phase was extracted with dichloromethane (50 mL×3). The combined organic phases were dried over anhydrous sodium sulfate and concentrated in vacuo. The resultant oil was purified by preparative HPLC (Mobile phase A: water with 0.05% ammonia solution; Mobile phase B: MeCN; column temperature: 30° C. Gradient: 37-44% B over 10 min) to give 6-chloro-N-((4-methoxy-6-methyl-2-oxo-1,2-dihydropyridin-3-yl)methyl)-7-(1-(tetrahydro-2H-pyran-4-yl)ethyl)pyrrolo[1,2-b]pyridazine-5-carboxamide (462.1 mg, 26% yield) as a yellow solid. LCMS (M+H+) m/z: calcd. 458.17, found 459.1. $^1$H NMR (400 MHz, CDCl$_3$) δ 0.96 (m, 1H), 1.21-1.18 (m, 1H), 1.39-1.36 (m, 1H), 1.42 (d, J=7.2, 3H), 1.94-1.91 (m, 1H), 2.37 (m, 1H), 2.40 (s, 3H), 3.25-3.22 (m, 1H), 3.38 (m, 1H), 3.43-3.40 (m, 1H), 3.77 (m, 1H), 3.91 (s, 3H), 4.04-4.01 (m, 1H), 4.66 (d, J=1.2, 2H), 5.96 (s, 1H), 6.75-6.72 (m, 1H), 8.04-8.02 (m, 1H), 8.13-8.12 (m, 1H), 8.82-8.79 (m, 1H), 13.17 (s, 1H).

Example 28

IC$_{50}$ Measurements for Inhibitors Using EZH2

EZH2 Assay: Assays were carried out by mixing rPRC2 together with biotinylated oligonucleosome substrates in the presence of the radio-labeled enzyme co-factor, S-adenosyl-L-methionine ($^3$H SAM) (Perkin Elmer) and monitoring the enzymatically mediated transfer of tritiated methyl groups from $^3$H SAM to histone lysine residues. The amount of resulting tritiated methyl histone product was measured by first capturing the biotinylated oligonucleosomes in streptavidin (SAV) coated FlashPlates (Perkin Elmer), followed by a wash step to remove unreacted $^3$H SAM, and then counting on a TopCount NXT 384 well plate scintillation counter (Perkin Elmer). The final assay conditions for EZH2 were as follows: 50 mM Tris Buffer pH 8.5, 1 mM DTT, 69 μM Brij-35 detergent, 5.0 mM MgCl$_2$, 0.1 mg/mL BSA, 0.2 μM $^3$H SAM, 0.2 μM biotinylated oligonucleosomes, 3.6 μM H3K27me3 peptide and 2 nM EZH2.

Compound IC$_{50}$ measurements were obtained as follows: Compounds were first dissolved in 100% DMSO as 10 mM stock solutions. Ten point dose response curves were generated by dispensing varying amounts of the 10 mM compound solution in 10 wells of the 384 well plate (Echo; Labcyte), pure DMSO was then used to backfill the wells to insure all wells have the same amount of DMSO. A 12.5 μL volume of the HMT enzyme, H3K27me3 peptide and oligonucleosome substrate in assay buffer was added to each well of the assay plate using a Multidrop Combi (Thermo-Fisher). Compounds were pre-incubated with the enzyme for 20 min, followed by initiation of the methyltransferase reaction by addition of 12.5 μL of $^3$H SAM in assay buffer (final volume=25 μL). The final concentrations of compounds ranged from a top default concentration of 80 μM down to 0.16 μM in ten 2-fold dilution steps. Reactions were carried out for 60 minutes and quenched with 20 μL per well of 1.96 mM SAH, 50 mM Tris pH 8.5, 200 mM EDTA. Stopped reactions were transferred to SAV coated Flashplates (Perkin Elmer), incubated for 120 min, washed with a plate washer, and then read on the TopCount NXT (1.0 min/well) to measure the amount of methyl histone product formed during the reaction. The amount of methyl histone product was compared with the amount of product formed in the 0% and 100% inhibition control wells allowing the calculation of % Inhibition in the presence of the individual compounds at various concentrations. IC$_{50}$'s were computed using a 4 parameter fit non-linear curve fitting software package (XLFIT, part of the database package, ActivityBase (IDBS)) where the four parameters were IC$_{50}$, Hill slope, pre-transitional baseline (0% INH), and post-transitional baseline (100% INH); with the latter two parameters being fixed to zero and 100%, respectively, by default.

Assay for Y641N EZH2 was performed as above using reconstituted H3K27Me2 oligonucleosomes as substrate.

Table 2 shows the activity of selected compounds of this invention in the EZH2 and Y641N EZH2 activity inhibition assay. IC$_{50}$ values are reported as follows: "A" indicates an IC$_{50}$ value of less than 100 nM; "B" indicates an IC$_{50}$ value of 100 nM to 1 μM; "C" indicates an IC$_{50}$ value of greater than 1 μM and less than 10 μM for each enzyme; "D" indicates an IC$_{50}$ value of greater than 10 μM for each enzyme; and "*(X μM)" indicates that no inhibition was observed at the highest concentration (i.e., X μM) of compound tested.

TABLE 2

IC50 Values for Compounds of Formula I against EZH2 and Y641N EZH2 Mutant Enzymes.

| Compound No. | EZH2 IC$_{50}$ | Y641N EZH2 IC$_{50}$ |
|---|---|---|
| 100 | C | D |
| 101 | A | A |
| 102 | A | A |
| 103 | A | B |
| 104 | A | B |
| 105 | A | A |
| 106 | A | A |
| 107 | A | B |
| 108 | A | B |
| 109 | B | B |
| 110 | A | B |
| 111 | *(0.25 μM) | C |
| 112 | A | B |
| 113 | A | A |
| 114 | A | A |
| 115 | A | A |
| 116 | A | A |
| 117 | A | A |
| 118 | A | A |
| 119 | A | A |
| 120 | B | B |

TABLE 2-continued

IC50 Values for Compounds of Formula I against EZH2 and Y641N EZH2 Mutant Enzymes.

| Compound No. | EZH2 IC$_{50}$ | Y641N EZH2 IC$_{50}$ |
|---|---|---|
| 121 | A | A |
| 122 | *(0.5 μM) | *(0.5 μM) |
| 123 | A | *(0.5 μM) |
| 124 | A | B |
| 125 | B | |
| 126 | C | |
| 127 | A | |
| 128 | A | |
| 129 | A | |
| 130 | A | |
| 131 | B | |
| 132 | A | |
| 133 | A | A |
| 134 | A | |
| 135 | A | C |
| 136 | A | |
| 137 | A | |
| 138 | A | C |
| 139 | A | A |
| 140 | A | C |
| 141 | A | |
| 142 | A | A |
| 143 | A | |
| 144 | A | B |
| 145 | A | |

Example 29

Et$_{50}$ Measurements for Inhibitors in Hela Cell Assays

H3K27me3 MSD Hela Assay. Trypsinized HeLa cells were counted and diluted in 10% DMEM (Life Technologies, Cat. #10569) to 5000 cells/75 μL. Seventy-five μL of cells were place in each well of a 96-well flat-bottomed plate and incubated at 37° C. for 4 hours. Twenty-five μL of test compound (at various concentrations) was added to the cells and incubation continued at 37° C. for 96 hours. Media was then removed and the cells rinsed once with ice cold PBS. Forty μL of ice-cold MSD Buffer AT (10 mM HEPES, pH 7.9, 5 mM MgCl$_2$, 0.25M sucrose, Benzonase (1:10000), 1% Triton X-100 supplemented with fresh 1× Protease Inhibitor cocktail and 1 mM 4-(2-Aminoethyl)benzenesulfonyl fluoride hydrochloride (AEBSF)) was added to each well and the plates placed on ice for 30 minutes. Ten μL of 5M NaCl was then added to each well and incubation on ice continued for another 15 minutes. The material in each well was suspended pipetting up and down and then transferred to a new 96 well plate. The emptied wells were rinsed with 150 uL ice-cold 20 mM Tris pH 7.5, 1 mM EDTA, 1 mM EGTA, supplemented with fresh 1× Protease Inhibitor cocktail and 1 mM AEBSF ("NO salt NO detergent buffer) and transferred to the respective wells in the new plate. Three hundred μL of NO Salt NO detergent buffer was then added to each well of lysates and the plates frozen at −80° C.

On the same day, an appropriate number of MSD standard bind 96-well plates were coated with 30 μL/well of total H3 capture antibody (Millipore, Cat # MAB3422) at 1 μg/mL concentration in PBS. The antibody solution was evenly distributed first by tapping gently on the sides of the plates and then by shaking the plates for a few minutes at 1000 rpm. Antibody coated plates were stored at 4° C. overnight.

The next day the lysates are thawed to RT. The antibody coated MSD plates are washed 3× with TBS-T (Tris-buffered saline (Fisher Scientific, Cat #BP2471-1)+0.2% Tween-20). One-hundred fifty μL of 5% Blocker A in TBS-T is added to each well. The wells are covered and shaken on a shaker at RT for one hour. The Blocker A step is repeated a second time. After removing the blocker, 25 μL of cell lysate is transferred into each antibody coated well. The plates are shaken for 2 hours at RT, the lysate removed and the plates again washed with Blocker A in TBS-T. Twenty-five μL of appropriate freshly prepared antibody mix (including both primary and secondary antibodies) is added to each well and the plates shaken for 1 hour at RT. The antibody mix used was one (or both) of those indicated in the table below:

| Ab | Concentration (μg/mL) | Primary Ab (μL) | Anti-rabbit detection Ab (μL) | 1% blocker A (μL) |
|---|---|---|---|---|
| H3K27me3 | 33 | 37.88 | 5.00 | 5000 |
| H3 | 12 | 52.08 | 5.00 | 5000 |

Both H3 antibodies were obtained from Cell Signalling (Cat #s 4499 and 9733). The goat anti-rabbit antibody was obtained from Meso-Scale Discovery (Cat #R32AB-1).

The antibody mix was then removed and the wells washed with Blocker A. One hundred-fifty μL of freshly prepared 1×MSD Read Buffer (Meso-Scale Discovery; Cat #R927C-2) was then added to each well and the plates read on a MSD Sector 2400 Plate Reader.

Data was analyzed using Assay Assistant (Constellation Pharmaceuticals In-house product) and Activity Base (IDBS Ltd, Surrey, UK) template. Data files were imported to Assay Assistant and assay conditions were specified. A unique Analysis ID was created and the data files exported to Activity Base. An analysis template was created on Activity Base to measure dose-dependent inhibition of H3K27me3 mark and cell viability respectively. Readout of DMSO wells were used to normalize the data. Resulting curves were fitted using Activity base software Model 205 (IDBS Ltd, Surrey, UK). The data was checked for quality, validated and integrated in excel format using SARview (IDBS Ltd, Surrey, UK).

H3K27me3 Alpha Hela Assay (AlphaLISA). Ten different doses of each test compound (in a series of 3-fold dilutions) were plated in duplicate 384-well tissue culture treated plates (Catalog #781080; Greiner Bio One; Monroe, N.C.). Hela cells grown in culture were trypsinized and counted using a Countess® cell counter (Catalog # C10281; Life Technologies, Grand Island, N.Y.). Cell were diluted to 67,000 cells per mL in 10% DMEM (Catalog #10569-010 Life Technologies, Grand Island, N.Y.) and 15 μL (1,000 cells) were plated into each well using the Biotek Micro-Flo™ Select Dispenser (BioTek Instruments, Inc. Vermont, USA),) of the 384-well plate. Plates were incubated at 37° C./5% $CO_2$ for 72 hrs. One of the duplicate plates was processed for HeLa assay and the other for viability.

To the plate processed for AlphaLISA was added 5 μL per well Cell-Histone Lysis buffer (1×) (Catalog # AL009F1 Perkin Elmer; Waltham, Mass.) and the plate was incubated at RT for 30 minutes on a plate shaker with low speed (Model#4625-Q Thermo Scientific; Waltham, Mass.). Then, 10 μL per well Histone Extraction buffer (catalog # AL009F2; Perkin Elmer; Waltham, Mass.) was added and the plate further incubated at RT for 20 min on plate shaker with low speed. To each well was then added 10 μL per well of a 5× mix of anti-K27me3 acceptor beads plus Biotinylated anti-Histone H3 (C-ter) Antibody (diluted to 3 nM final) (Catalog #AL118 Perkin Elmer; Waltham, Mass.). Dilution of the acceptor beads and then anti-Histone H3 was with 1× Histone Detection buffer (Catalog # AL009F3 Perkin Elmer; Waltham, Mass.) which was produced diluted from the 10× stock provided. The plate was sealed with an aluminum plate sealer and incubated at 23° C. for 60 min. We then added 10 μL 5× solution of Streptavidin Donor beads (Catalog #6760002 Perkin Elmer; Waltham, Mass.) (20 μg/mL final in 1× Histone Detection Buffer), sealed the plate with Aluminum plate sealer and incubated at 23° C. for 30 min. The plates were then read using an EnVision-Alpha Reader (model #2104 Perkin Elmer; Waltham, Mass.).

Cell viability was assayed by adding 15 μL of Cell Titer Glo ((Catalog #G7571 Promega Madison, Wis.) to each well with cells with media. The plates were incubated for RT for 15-20 minutes on a plate shaker at low speed. The plates were then read using an EnVision-Alpha Reader (model #2104 Perkin Elmer; Waltham, Mass.).

Data from both assays was analyzed using Assay Assistant (Constellation Pharmaceuticals In-house product) and Activity Base (IDBS Ltd, Surrey, UK) template. Data files were imported to Assay Assistant and assay conditions were specified. A unique Analysis ID was created and the data files exported to Activity Base. An analysis template was created on Activity Base to measure dose-dependent inhibition of H3K27me3 mark and cell viability respectively. Readout of DMSO wells were used to normalize the data. Resulting curves were fitted using Activity base software Model 205 (IDBS Ltd, Surrey, UK). The data was checked for quality, validated and integrated in excel format using SARview (IDBS Ltd, Surrey, UK).

Table 3 shows the activity of selected compounds of this invention in the two different HeLa cell assays described above. $EC_{50}$ values are reported as follows: "A" indicates an $EC_{50}$ value of less than 400 nM; "B" indicates an $EC_{50}$ value of 400 nM to 2 μM; "C" indicates an $EC_{50}$ value of greater than 2 μM and less than 10 μM for each enzyme; "D" indicates an $EC_{50}$ value of greater than 10 μM for each enzyme; and "*(X μM)" indicates that no inhibition was observed at the highest concentration (i.e., X μM) of compound tested.

TABLE 3

$EC_{50}$ Values for Tested Compounds of the Invention in Hela Cells Expressing H3k27 Wild Type EZH2.

| Compound No. | H3K27me3_Alpha_HeLa (EC50) | H3K27me3_MSD_HeLa_ (EC50) |
|---|---|---|
| 101 | A | A |
| 102 | | B |
| 103 | | B |
| 105 | A | A |
| 106 | | A |
| 107 | | C |
| 108 | | B |
| 110 | | C |
| 112 | | C |
| 113 | | A |
| 114 | | A |
| 115 | | A |
| 116 | A | A |
| 127 | C | |
| 128 | A | |
| 129 | B | |
| 130 | C | |
| 132 | A | |
| 133 | A | |
| 134 | B | |
| 135 | A | |

TABLE 3-continued

EC$_{50}$ Values for Tested Compounds of the Invention
in Hela Cells Expressing H3k27 Wild Type EZH2.

| Compound No. | H3K27me3_Alpha_HeLa (EC50) | H3K27me3_MSD_HeLa_ (EC50) |
|---|---|---|
| 136 | A | |
| 137 | A | |
| 138 | A | |
| 139 | A | |
| 140 | A | |
| 141 | A | |
| 142 | A | |
| 143 | A | |
| 144 | A | |
| 145 | A | |

Karpas-422 GI50 Assay—Ten different doses of each test compound (in a series of 3-fold dilutions) are plated in 384-well tissue culture treated plates (Catalog #781080; Greiner Bio One; Monroe, N.C.). Karpas-422 cells grown in suspension culture are counted using a Countess® cell counter (Catalog # C10281; Life Technologies, Grand Island, N.Y.). Cells are diluted to 25,000 cells per mL in 10% RPMI (Catalog #61870-036 Life Technologies, Grand Island, N.Y.) and 45 µL (1,125 cells) are plated into each well using the Biotek MicroFlo™ Select Dispenser (BioTek Instruments, Inc. Vermont, USA),) of the 384-well plate. Plates were incubated at 37° C./5% CO$_2$ for 168 hrs (7 days).

Cell viability is assayed by adding 30 µL of Cell Titer Glo ((Catalog #G7571 Promega Madison, Wis.) to each well with cells with media. The plates are incubated at RT for 30 minutes on a plate shaker at low speed. The plates are then read using an EnVision-Alpha Reader (model #2104 Perkin Elmer; Waltham, Mass.).

Data from the assay is analyzed using Assay Assistant (Constellation Pharmaceuticals In-house product) and Activity Base (IDBS Ltd, Surrey, UK) template. Data files are imported to Assay Assistant and assay conditions are specified. A unique Analysis ID is created and the data files exported to Activity Base. An analysis template is created on Activity Base to measure dose-dependent cell viability. Readout of DMSO wells are used to normalize the data. Resulting curves are fitted using Activity base software Model 205 (IDBS Ltd, Surrey, UK). The data is checked for quality, validated and integrated in excel format using SARview (IDBS Ltd, Surrey, UK).

We claim:

1. A compound having structural formula I:

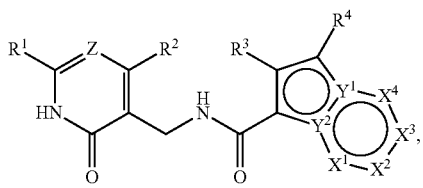

(I)

or a pharmaceutically acceptable salt or tautomer thereof, wherein:

Z is C(R$^9$) or N;
one of Y$^1$ or Y$^2$ is N and the other is C;
one of X$^1$, X$^2$, X$^3$, or X$^4$ is N and each of the others is independently C(R$^5$);

each of R$^1$, R$^2$ and R$^9$ is independently selected from hydrogen, halo, —OH, —CN, C$_1$-C$_4$ alkyl, —O—(C$_1$-C$_4$ alkyl), —N(R$^7$)$_2$, —(C$_0$-C$_4$ alkylene)-aryl, —(C$_0$-C$_4$ alkylene)-heteroaryl, —(C$_0$-C$_4$ alkylene)-heterocyclyl, and —(C$_0$-C$_4$ alkylene)-carbocyclyl; or R$^1$ and R$^9$ are taken together with atoms to which they are bound to form an aryl, heteroaryl, heterocyclyl, or carbocyclyl ring; or R$^2$ and R$^9$ are taken together with atoms to which they are bound to form an aryl, heteroaryl, heterocyclyl, or carbocyclyl ring;

each of R$^3$, R$^4$ and R$^5$ is independently selected from hydrogen, halo, —CN, —(C$_0$-C$_4$ alkylene)-R$^8$, —(C$_2$-C$_6$ alkenylene or alkynylene)-R$^6$, —(C$_1$-C$_4$ alkylene)-O—R$^6$, —(C$_1$-C$_4$ alkylene)-O—(C$_1$-C$_4$ alkylene)-R$^8$, —O—(C$_0$-C$_4$ alkylene)-R$^6$, —O—(C$_2$-C$_4$ alkylene)-O—R$^8$, —O—(C$_1$-C$_4$ alkylene)-R$^6$, —(C$_0$-C$_4$ alkylene)-N(R$^7$)$_2$, —(C$_0$-C$_4$ alkylene)-C(O)—O—R$^6$, —(C$_0$-C$_4$ alkylene)-O—C(O)—R$^6$, —(C$_0$-C$_4$ alkylene)-C(O)—N(R$^7$)$_2$, —(C$_0$-C$_4$ alkylene)-N(R$^7$)—C(O)—R$^6$, —O—(C$_1$-C$_4$ alkylene)-C(O)—N(R$^7$)$_2$, —O—(C$_2$-C$_4$ alkylene)-N(R$^7$)—C(O)—(R$^7$), —(C$_0$-C$_4$ alkylene)-S(O)—R$^8$, —(C$_0$-C$_4$ alkylene)-S(O)$_2$—R$^8$, —(C$_0$-C$_4$ alkylene)-S(O)$_2$—N(R$^7$)$_2$, —(C$_0$-C$_4$ alkylene)-N(R$^7$)—S(O)$_2$—R$^8$, and —(C$_0$-C$_4$ alkylene)-C(O)—R$^8$;

each R$^6$ is independently selected from hydrogen or R$^8$;
each R$^7$ is independently selected from hydrogen, —(C$_0$-C$_4$ alkylene)-R$^6$, —(C$_0$-C$_4$ alkylene)-O—R$^6$, —S(O)$_2$—R$^8$, —C(=O)—R$^8$, —C(=O)—N(R$^6$)$_2$, —(C$_1$-C$_4$ alkylene)-O—C(=O)—R$^8$ and —(C$_0$-C$_4$ alkylene)-C(=O)—O—R$^6$; or two R$^7$ are taken together with the nitrogen atom to which they are commonly bound to form an optionally substituted heterocyclyl or heteroaryl;

R$^8$ is selected from C$_1$-C$_4$ alkyl, aryl, heteroaryl, carbocyclyl and heterocyclyl; wherein unless otherwise designated any alkyl, alkylene, alkenyl, alkynyl, aryl, heteroaryl, heterocyclyl or carbocyclyl portion of the compound is optionally substituted.

2. The compound of claim 1, wherein Z is CH.

3. The compound of claim 1, wherein each of R$^1$ and R$^2$ is independently selected from —C$_1$-C$_3$ alkyl, —C$_1$-C$_3$ haloalkyl, O—(C$_1$-C$_3$ alkyl) and —O—(C$_1$-C$_3$ haloalkyl).

4. The compound of claim 3, wherein R$^1$ is methyl.

5. The compound of claim 4, wherein R$^2$ is selected from —CH$_3$, —CH$_2$CH$_3$, —CH$_2$CH$_2$CH$_3$, —OCH$_3$, and —OCHF$_2$.

6. The compound of claim 5, wherein Y$^1$ is N and X$^4$ is N.

7. The compound of claim 6, wherein X$^5$ is selected from C(H), C(OCH$_3$) and C(CH$_3$).

8. The compound of claim 5, wherein Y$^1$ is N and X$^2$ is N.

9. The compound of claim 5, wherein Y$^2$ is N and X$^3$ is N.

10. The compound of claim 9, wherein R$^3$ is methyl or chloro.

11. The compound of claim 10, wherein R$^4$ is selected from -heteroaryl, —CH(CH$_3$)-heterocyclyl, —CH(CH$_3$)-heteroaryl, —CH(CH$_3$)-aryl, —CH(CH$_3$)-carbocyclyl,)—CH(CH$_3$)—N(R$^{10}$)—S(O)$_2$—(C$_1$-C$_4$ alkyl) —CH(CH$_3$)—N(R$^{10}$)—C(O)—(C$_1$-C$_4$ alkyl), and —CH(CH$_3$)N(R$^{10}$)$_2$, wherein R$^{10}$ is selected from hydrogen and C$_1$-C$_4$ alkyl, and wherein any aryl, heteroaryl, heterocyclyl or carbocyclyl portion of R$^4$ is optionally substituted.

12. The compound of claim 11, wherein R⁴ is selected from 1-(1-methylpiperidin-4-yl)ethyl, 5-methyl-isoxazol-4-yl, 3,5-dimethyl-isoxazol-4-yl, 1,5-dimethyl-1H-pyrazol-3-yl, 1-(1-ethylsulfonylpiperidin-4 - yl)ethyl, 1,4-dimethyl-1H-pyrazol-5 -yl, 1-methyl-1H-pyrazol-5-yl, 1-(tetrahydropyran-4-yl)ethyl, 1-(pyridin-3-yl)ethyl, 1-(methylsulfonylamino)ethyl, 1-(1-methyl-2-oxopiperidin-4-yl)ethyl, 1-(methylsulfonyl(N-ethyl)amino)ethyl, 1-(methylsulfonyl(N-methyl)amino)ethyl, 1-phenylethyl, 1-(methylcarbonyl(N-methyl)amino)ethyl, and 1-cyclopropylethyl.

13. The compound of claim 11, wherein R⁴ is selected from 1-(1-(2,2-difluoropropanoyl)piperidin-4-yl)ethyl, 1-(1-(2,2-difluoroethanoyl)piperidin-4-yl)ethyl, 1-(1-(2,2,2-trifluoroethyl)piperidin-4-yl)ethyl, 1-(1-(2,2,2-trifluoroethanoyl)piperidin-4-yl)ethyl, 1-(1-(2-fluoro-2-methylpropyl)piperidin-4-yl)ethyl, 1-(1-(2,2-difluoropropyl)piperidin-4-yl)ethyl, 1-(1-(3,3,3-trifluoropropanoyl)piperidin-4-yl)ethyl, 1-(1-(3,3,3-trifluoropropyl)piperidin-4-yl)ethyl, 1-(1-(2-hydroxy-2-methylpropyl)piperidin-4-yl)ethyl, 1-(1-(2,2-difluoroethyl)piperidin-4-yl)ethyl, 1-(dimethylamino)ethyl, morpholine-4-carbonyl, 4-methylsulfonylpiperazin-1-ylcarbonyl, 1-(tetrahydro-2H-pyran-4-yl)ethyl, 1-(1-(2-fluoro-2-methylpropanoyl)piperidin-4-yl)ethyl, and 1-(ethyl(methyl)amino)ethyl.

14. The compound of claim 13, wherein each R⁵ is hydrogen.

15. The compound of claim 1, wherein the compound is of the structural formula (II):

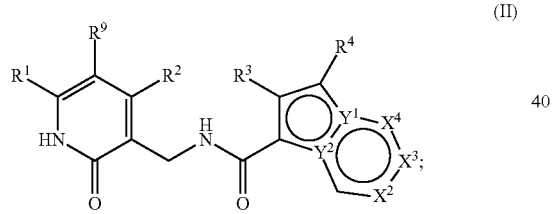

or a pharmaceutically acceptable salt or tautomer thereof, wherein:
each of R¹, R² and R⁹ is independently selected from hydrogen, $C_1$-$C_4$ alkyl, and —O—($C_1$-$C_4$ alkyl);
one of Y¹ or Y² is N and the other is C;
one of X², X³, or X⁴ is N and each of the others is independently CH or —O—($C_1$-$C_4$ alkyl);
R³ is selected from hydrogen, halo, and $C_1$-$C_4$ alkyl;
R⁴ is selected from —C(O)—R⁸, —($C_0$-$C_4$ alkylene)-R⁸, and —($C_0$-$C_4$ alkylene)-N(R⁷)₂;
R⁷ is selected from hydrogen, $C_1$-$C_4$ alkyl, —S(O)₂—$C_1$-$C_4$ alkyl, and —C(=O)—$C_1$-$C_4$ alkyl; or
two R⁷ are taken together with the nitrogen atom to which they are commonly bound to form an optionally substituted heterocyclyl; and
R⁸ is selected from $C_1$-$C_4$ alkyl, aryl, heteroaryl, carbocyclyl and heterocyclyl, wherein each of the aryl, heteroaryl, carbocyclyl and heterocyclyl are optionally substituted.

16. The compound of claim 1, wherein the compound is selected from

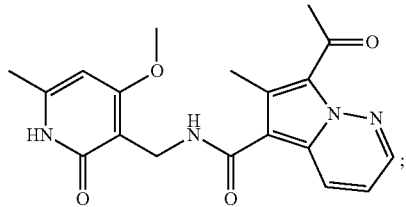

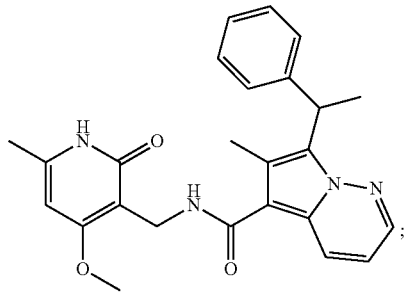

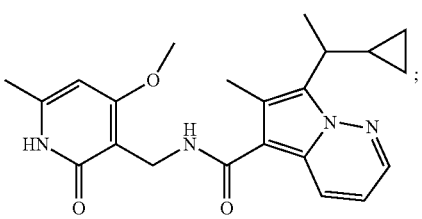

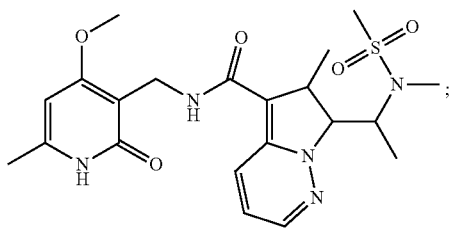

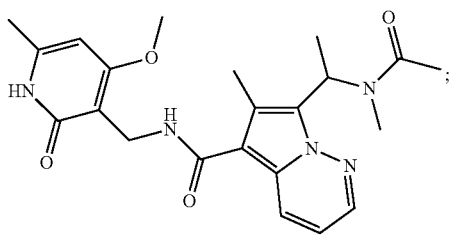

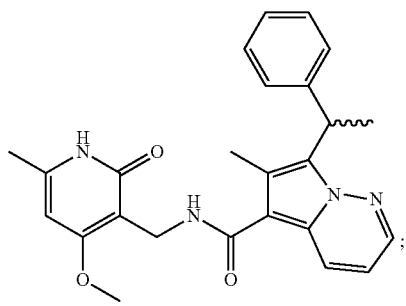

135
-continued
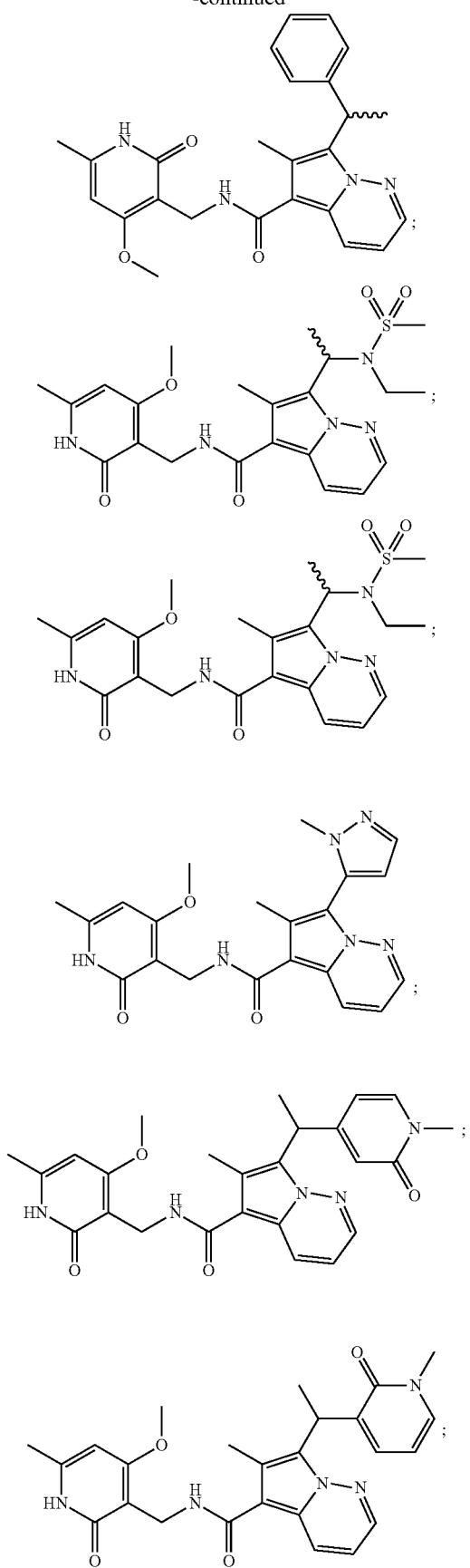
136
-continued
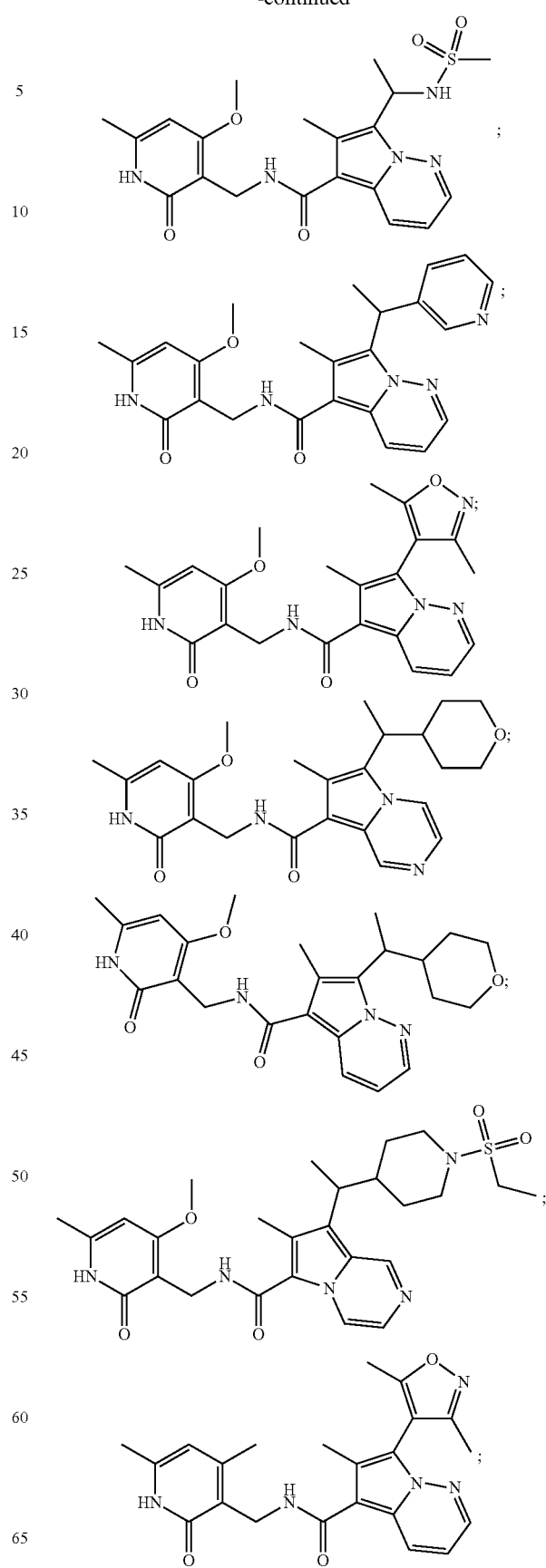

137
-continued
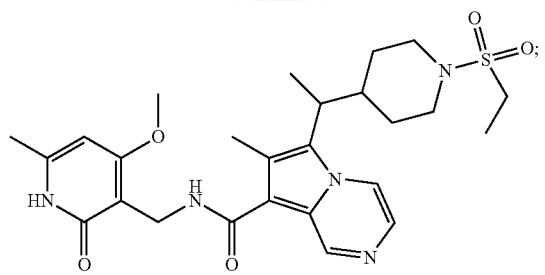
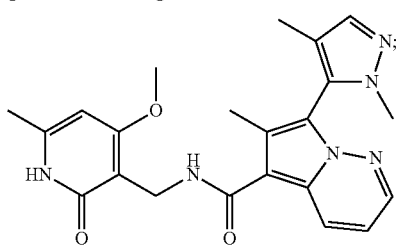
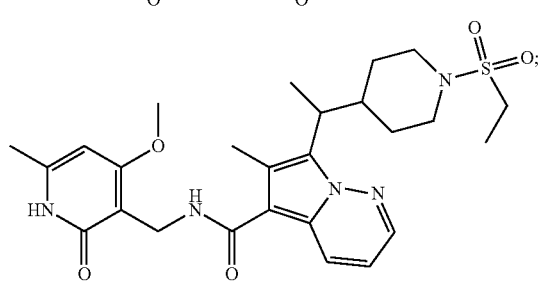
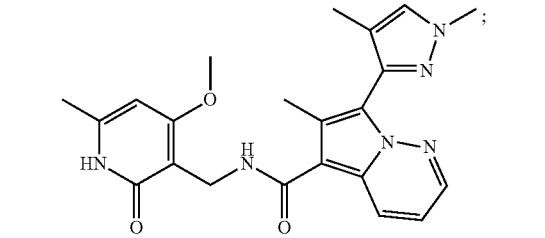
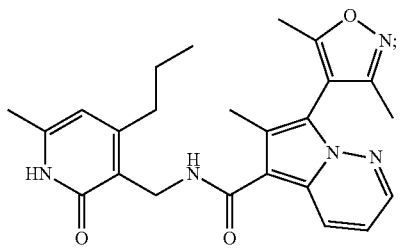
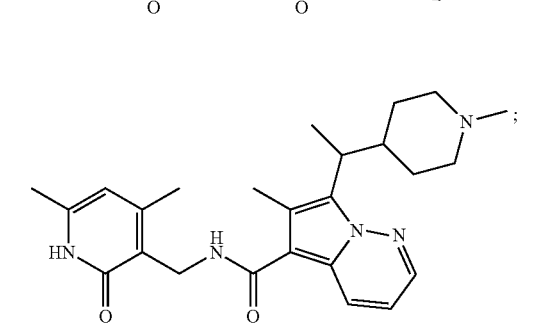
138
-continued
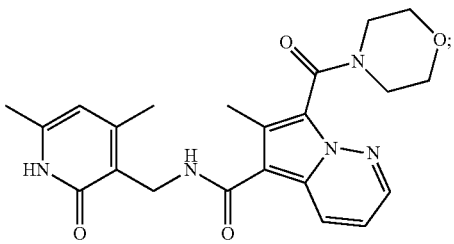
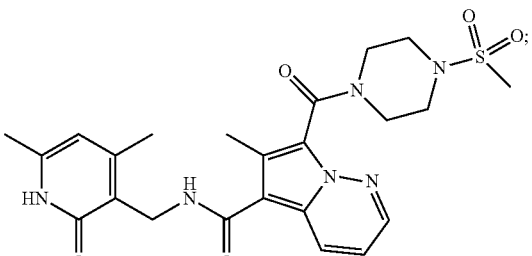
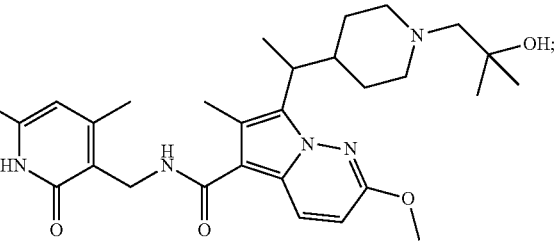
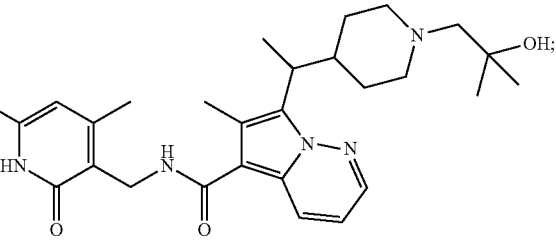
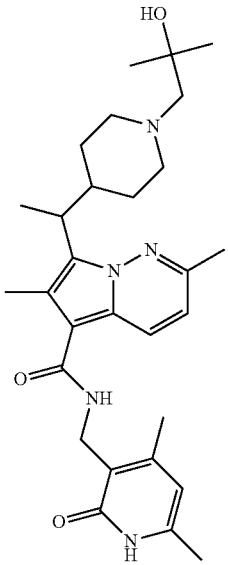

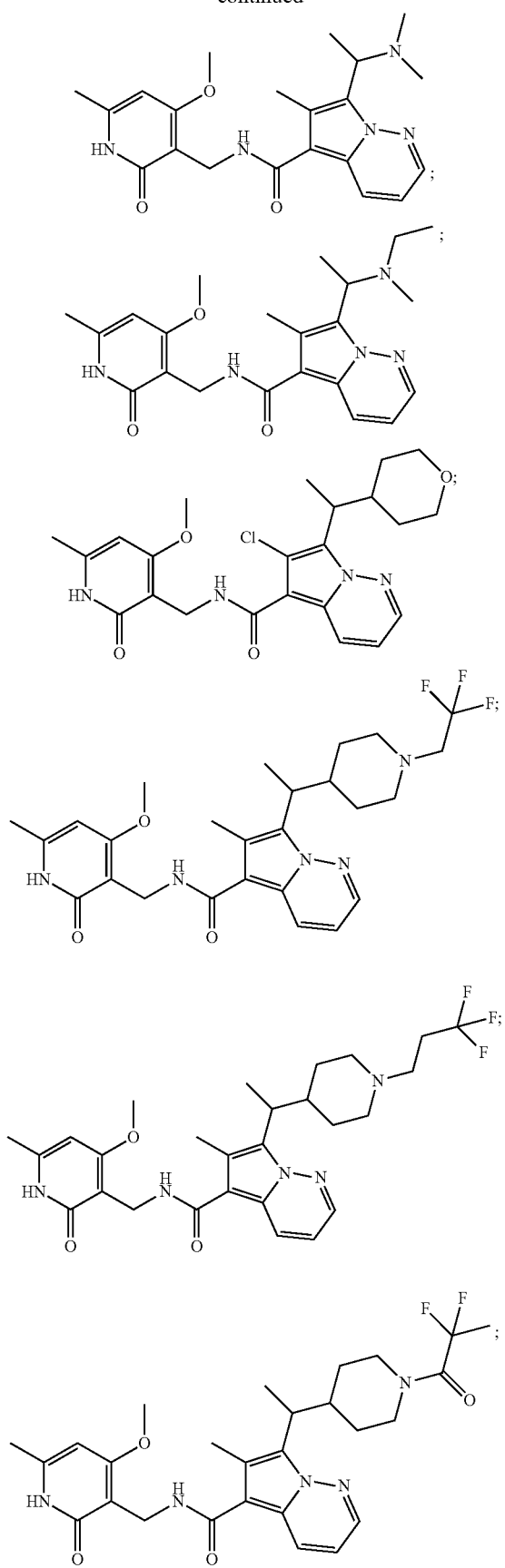
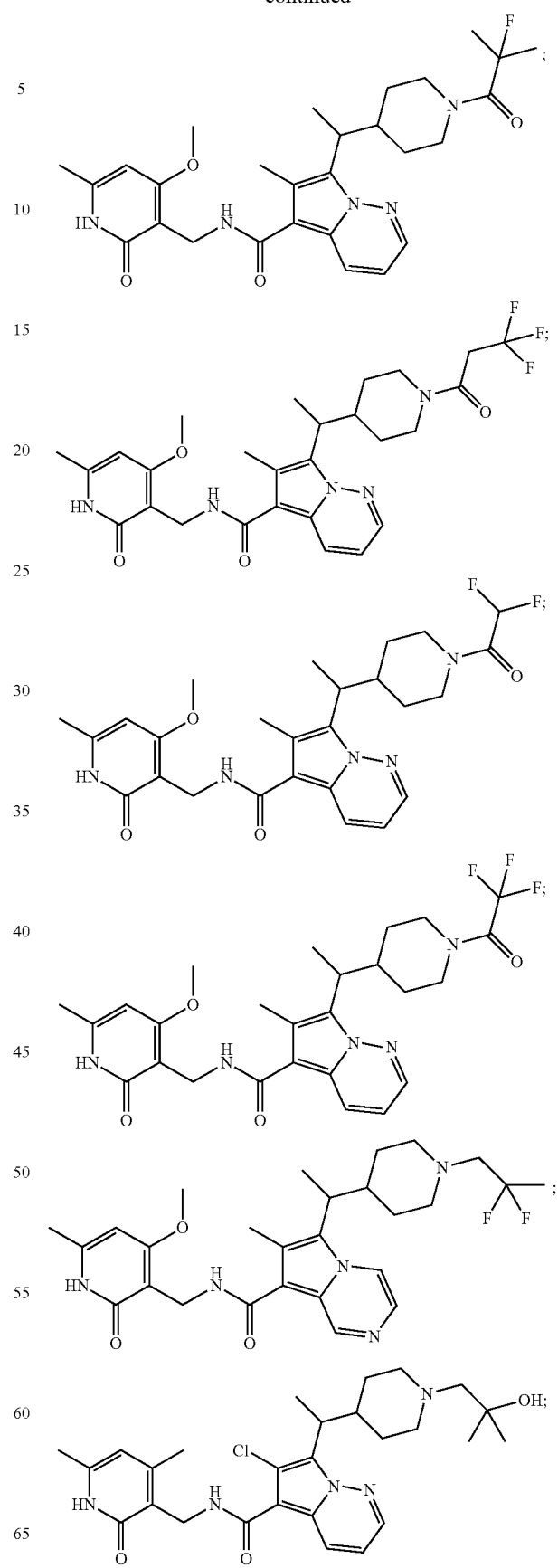

-continued
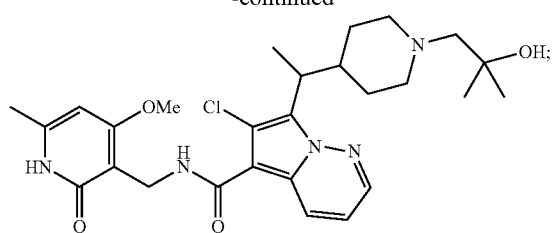
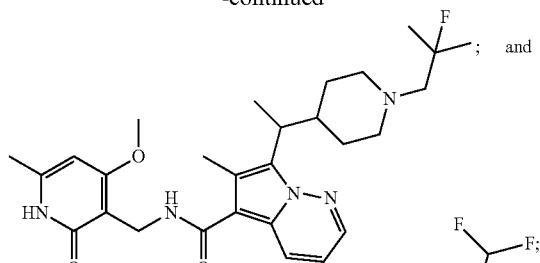
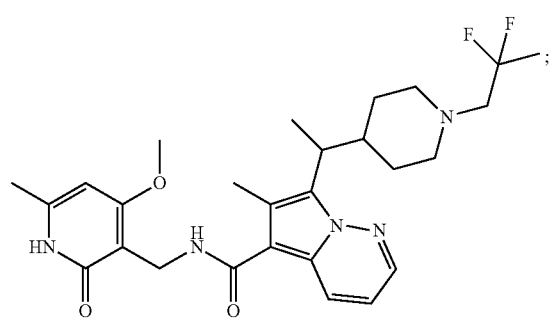
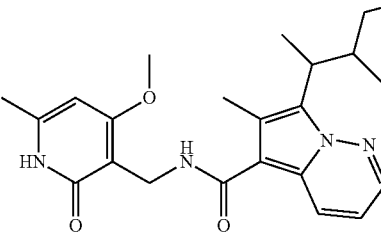
or a pharmaceutically acceptable salt thereof.
17. A composition comprising a compound of claim 1; and a pharmaceutically acceptable carrier.
* * * * *

UNITED STATES PATENT AND TRADEMARK OFFICE
CERTIFICATE OF CORRECTION

PATENT NO. : 9,745,305 B2
APPLICATION NO. : 14/769471
DATED : August 29, 2017
INVENTOR(S) : Brian K. Albrecht et al.

It is certified that error appears in the above-identified patent and that said Letters Patent is hereby corrected as shown below:

In the Claims

Column 134, Claim 16, Lines 35-40, please replace " 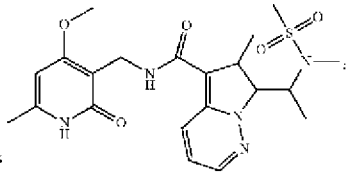 " with

-- 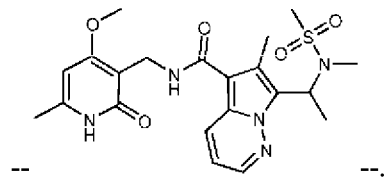 --.

Signed and Sealed this
Twenty-first Day of November, 2017

Joseph Matal
*Performing the Functions and Duties of the
Under Secretary of Commerce for Intellectual Property and
Director of the United States Patent and Trademark Office*